US010383924B2

(12) United States Patent
Hodge et al.

(10) Patent No.: US 10,383,924 B2
(45) Date of Patent: Aug. 20, 2019

(54) COMBINATION IMMUNOTHERAPY COMPOSITIONS AGAINST CANCER AND METHODS

(75) Inventors: James Hodge, Kensington, MD (US); Jeffrey Schlom, Potomac, MD (US); Alex Franzusoff, Nahant, MA (US)

(73) Assignees: GlobeImmune, Inc., Louisville, CO (US); The USA, as represented by the Secretary, Dept. of Health and Human Services, Bethesda, MD (US)

( * ) Notice: Subject to any disclaimer, the term of this patent is extended or adjusted under 35 U.S.C. 154(b) by 0 days.

(21) Appl. No.: 13/264,846

(22) PCT Filed: Apr. 16, 2010

(86) PCT No.: PCT/US2010/031460
§ 371 (c)(1),
(2), (4) Date: Jan. 12, 2012

(87) PCT Pub. No.: WO2010/121180
PCT Pub. Date: Oct. 21, 2010

(65) Prior Publication Data
US 2012/0107347 A1 May 3, 2012

Related U.S. Application Data

(60) Provisional application No. 61/170,530, filed on Apr. 17, 2009.

(51) Int. Cl.
*A61K 39/00* (2006.01)
*A61K 39/395* (2006.01)
*C07K 16/28* (2006.01)
*C07K 14/705* (2006.01)
*C07K 16/30* (2006.01)

(52) U.S. Cl.
CPC .... *A61K 39/0011* (2013.01); *A61K 2039/523* (2013.01); *A61K 2039/55522* (2013.01); *Y02A 50/403* (2018.01); *Y02A 50/41* (2018.01); *Y02A 50/412* (2018.01)

(58) Field of Classification Search
CPC .... C07K 14/4748; A61K 38/00; A61K 39/00; A61K 39/0011; C12Q 1/6886
USPC ................................ 424/204, 199
See application file for complete search history.

(56) References Cited

U.S. PATENT DOCUMENTS

| | | | |
|---|---|---|---|
| 4,775,622 A | 10/1988 | Hitzeman et al. | |
| 5,234,830 A | 8/1993 | Oshima et al. | |
| 5,310,654 A | 5/1994 | Isberg et al. | |
| 5,413,914 A | 5/1995 | Franzusoff | |
| 5,830,463 A | 11/1998 | Duke et al. | |
| 5,833,975 A | 11/1998 | Paoletti et al. | |
| 5,858,378 A | 1/1999 | Bostwick | |
| 5,919,651 A | 7/1999 | Hitzeman et al. | |
| 5,942,235 A | 8/1999 | Paoletti | |
| 7,083,787 B2 | 8/2006 | Duke et al. | |
| 7,439,042 B2 | 10/2008 | Duke et al. | |
| 7,465,454 B2 | 12/2008 | Franzusoff et al. | |
| 7,736,642 B2 | 6/2010 | Duke et al. | |
| 7,745,128 B2 | 6/2010 | Guo et al. | |
| 2002/0044948 A1 | 4/2002 | Khleif | |
| 2003/0035810 A1 | 2/2003 | Caplan | |
| 2005/0238627 A1* | 10/2005 | Ohno et al. | 424/93.21 |
| 2006/0121011 A1* | 6/2006 | Jolly et al. | 424/93.21 |
| 2007/0172503 A1 | 7/2007 | Selitrennikoff et al. | |
| 2010/0034840 A1 | 2/2010 | Apelian et al. | |
| 2010/0111912 A1 | 5/2010 | Apelian et al. | |
| 2010/0189749 A1 | 7/2010 | Franzusoff et al. | |
| 2010/0196411 A1 | 8/2010 | Duke et al. | |
| 2011/0256098 A1 | 10/2011 | Apelian et al. | |

FOREIGN PATENT DOCUMENTS

| | | | |
|---|---|---|---|
| EP | 0414404 | | 2/1991 |
| FR | 2486400 | | 1/1982 |
| JP | H10-506902 | | 7/1998 |
| JP | 2007-105045 | | 4/2007 |
| WO | WO 99/19478 | | 4/1999 |
| WO | WO 00/34494 | | 6/2000 |
| WO | WO2006044923 | * | 4/2006 |
| WO | WO2007092792 | * | 8/2007 |
| WO | WO 2010/065626 | | 6/2010 |
| WO | WO 2011/032119 | | 3/2011 |
| WO | WO 2011/115914 | | 9/2011 |
| WO | WO 2012/019127 | | 2/2012 |

OTHER PUBLICATIONS

Boehm et al., Concurrent vaccination with two distinct vaccine platforms targeting the same antigen generates phenotypically and functionally distinct T-cell populations, 2010, Cancer Immunology Immunotherapy, 59:397-408.*
Wansley et al., Vaccination with a recombinant *Saccharomyces cerevisiae* expressing a tumor antigen breaks immune tolerance and elicits therapeutic antitumor responses, 2008, Clinical Cancer Research, 14(13):4316-4325.*
Bernstein et al. "Recombinant *Saccharomyces cerevisiae* (yeast-CEA) as a potent activator of murine dendritic cells", 2008, Vaccine, 26:509-521.*
Abrams et al., "Mutant ras Epitopes as Targets for Cancer Vaccines", Feb. 1996, vol. 23, abstract only.
Bernstein et al. "Recombinant *Saccharomyces cerevisiae* (yeast-CEA) as a potent activator of murine dendritic cells." Vaccine, Dec. 2007, vol. 26, No. 4, pp. 509-521.
Bizzini et al. "Use of live *Saccharomyces cerebisiae* cells as a biological response modifier in experimental infections," FEMS Microbiology Immunology, Oct. 1990, vol. 64, No. 3, pp. 155-168.
Boehm et al. "Concurrent vaccination with two distinct vaccine platforms targeting the same antigen generates phenotypically and functionally distinct T-cell populations." Cancer Immunology, Immunotherapy, Mar. 2010, vol. 59, No. 3, pp. 397-408.

(Continued)

*Primary Examiner* — Barry A Chestnut
(74) *Attorney, Agent, or Firm* — Sheridan Ross P.C.

(57) ABSTRACT

Disclosed are immunotherapeutic compositions and the concurrent use of combinations of such compositions for the improved induction of therapeutic immune responses and/or for the prevention, amelioration and/or treatment of disease, including, but not limited to, cancer and infectious disease.

25 Claims, 8 Drawing Sheets

Specification includes a Sequence Listing.

(56) References Cited

OTHER PUBLICATIONS

Boehm et al. "Abstract #347: Vaccination with two distinct vaccine vector platforms targeting the same antigen generates phenotypically and functionally distinct T-cell populations." Proc Am Assoc Cancer Res, Apr. 18-22, 2009, 1 page Abstract Only.
Bos et al. "Characterization of Antigen-Specific Immune Responses Induced by Canarypox Virus Vaccines." The Journal of Immunology, Nov. 1, 2007, vol. 179, No. 9, pp. 6115-6122.
Brake et al. "a-Factor-directed synthesis and secretion of mature foreign proteins in *Saccharomyces cerevisiae*." PNAS, Aug. 1984, vol. 81, pp. 4642-4646.
Casimiro et al. "Comparative Immunogenicity in Rhesus Monkeys of DNA Plasmid, recombinant Vaccinia Virus, and Replication-Defective Adenovirus Vectors Expressing a Human Immunodeficiency Virus Type 1 gag Gene." Journal of Virology, Jun. 2003, vol. 77, No. 11, pp. 6305-6313.
Chan et al. "HER-2/neu-gene engineered dendritic cell vaccine stimulates stronger HER-2/neu-specific immune responses compared to DNA vaccination." Gene Therapy, Oct. 2006, vol. 13, No. 19, pp. 1391-1402.
Eto et al. Immunization with Recombinant *Escherichia coli* Expressing Retinal S-Antigen-Induced Experimental Autoimmune Uveitis (EAU) in Lewis Rats, Cellular Immunology, Mar. 1993, vol. 147, No. 1, pp. 203-214.
Franzusoff et al. "Yeasts Encoding Tumour Antigens in Cancer Immunotherapy," Expert Opinion on Biological Therapy, Apr. 1, 2005, vol. 5, No. 4, pp. 565-575.
Franzusoff et al. "Biochemical and Genetic Definition of the Cellular Protease Required for HIV-1 gp160 Processing," The Journal of Biological Chemistry, Feb. 17, 1995, vol. 270, No. 7, pp. 3154-3159.
Fujita et al. "Studies in the development of Japanese encephalitis vaccine: expression of virus envelope glycoprotein V3 (E) gene in yeast." Bulletin of the World Health Organization, Feb. 1987, vol. 65, No. 3, pp. 303-308.
Gulley et al. "A Piliot Study to Evaluate the Safety and Clinical Outcomes of Vaccination with Recombinant CEA-MUC-1-TRICOM (PANVAC) Poxviral-based Vaccines in Patients with Metastatic Carcinoma." Clinical Cancer Research, May 15, 2008, vol. 14, No. 10, pp. 3060-3069.
Hodge et al. "Modified Vaccinia Virus Ankara Recombinants Are as Potent as Vaccinia Recombinants in Diversified Prime and Boost Vaccine Regimens to Elicit Therapeutic Antitumor Responses." Cancer Research, Nov. 15, 2003, vol. 63, No. 22, pp. 7942-7949.
Klepfer et al. "Characterization of rabies glycoprotein expressed in yeast." Archives of Virology, 1993, vol. 128, No. 3-4, pp. 269-286.
Lu et al., "Mutation-Selective Tumor Remission with Ras-Targeted, Whole Yeast-Based Immunotherapy", Cancer Research, Aug. 1, 2004, vol. 64, pp. 5084-5088.
Marshall et al. "Phase I Study in Cancer Patients of a Replication-Defective Avipox Recombinant Vaccine That Expresses Human Carcinoembryonic Antigen," Journal of Clinical Oncology, Jan. 1999, vol. 17, No. 1, pp. 332-337.
Marshall et al. "Phase I Study of Sequential Vaccinations With Fowlpox-CEA(6D)-Tricom Alone and Sequentially With Vaccinia-CEA(6D)Tricom, With and Without Granulocyte-Macrophage Colony-Stimulating Factor, in Patients With Carcinoembryonic Antigen-Expressing Carcinomas." Journal of Clinical Oncology, Feb. 2005, vol. 23, No. 4, pp. 720-731.
Millar et al. "The magnitude of the CD8+ T cell response produced by recombinant virus vectors is a function of both the antigen and the vector." Cellular Immunology, Nov.-Dec. 2007, vol. 250, No. 1-2, pp. 55-67.
Moore et al. "Novel yeast-based vaccine against HIV-SF2 gp160 promotes a cytotoxic 43-62 cell response." FASEB Journal 1996, vol. 10, No. 6, p. A1473 ZP002186594.
Mylin et al. "Quantitation of CD8+ T-Lymphocyte Responses to Multiple Epitopes from Simian Virus 40 (SV40) Large T Antigen in C57BL/6 Mice Immunized with SV40, SV40 T-Antigen-Transformed Cells, or Vaccinia Virus Recombinants Expressing Full-Lengtch T Antigen or Epitope Minigenes." Journal of Virology, Aug. 2000, vol. 74, No. 15, pp. 6922-6934.
Näslund et al. "Comparative Prime-Boost Vaccinations Using Semliki Forest Virus, Adenovirus, and ALVAC Vectors Demonstrate Differences in the Generation of Protective Central Memory CTL Response against the P815 Tumor." The Journal of Immunology, Jun. 1, 2007, vol. 178, No. 11, pp. 6761-6769.
Riezebos-Brilman et al. "A comparative study on the immunotherapeutic efficacy of recombinant Semliki Forest virus and adenovirus vector systems in a murine model for cervical cancer." Gene Therapy, Dec. 2007, vol. 14, No. 24, pp. 1695-1704.
Schreuder et al. "Yeast expressing hepatitis B virus surface antigen determinants on its surface: implications for a possible oral vaccine." Vaccine, Apr. 1996, vol. 14, No. 5, pp. 383-388.
Sinai et al. "Enhancement of Resistance to Infectious Diseases by Oral Administration of Brewer's Yeast," Infection and Immunity, May 1974, vol. 9, No. 5, pp. 781-787.
Stubbs et al. "Whole recombinant yeast vaccine activates dendric cells and elicits protective cell-mediated immunity." Nature Medicine, May 2001, vol. 7, No. 5, pp. 1-5.
Valenzuela et al. "Antigen engineering in yeast: Synthesis and assembly of hybrid hepatitis B surface antigen-Herpes simplex 1 gD particles," Bio/Technology, Apr. 1985, vol. 3, pp. 323-326.
Wansley et al. "Vaccination with a Recombinant *Saccharomyces cerevisiae* Expressing a Tumor Antigen Breaks Immune Tolerance and Elicits Therapeutic Antitumor Responses." Clinical Cancer Research, Jul. 2008, vol. 14, No. 13, pp. 4316-4325.
Weide et al. "Plasmid DNA- and messenger RNA-based anti-cancer vaccination." Immunology Letters, Jan. 15, 2008, vol. 115, No. 1, pp. 33-42.
Wu et al. "Enhanced Breadth of CD4 T-Cell Immunity by DNA Prime and Adenovirus Boost Immunization to Human Immunodeficiency Virus Env and Gag Immunogens." Journal of Virology, Jul. 2005, vol. 79, No. 13, pp. 8024-8031.
Yang et al. "Antigen-presenting cells containing multiple costimulatory molecules promote activation and expansion of human antigen-specific memory CD8+ T cells." Cancer Immunology, Immunotherapy, Apr. 2009, vol. 58, No. 4, pp. 503-515.
International Search Report for International (PCT) Patent Application No. PCT/US2010/031460, dated Jul. 22, 2010 3 pages.
Written Opinion for International (PCT) Patent Application No. PCT/US2010/031460, dated Jul. 22, 2010 7 pages.
International Preliminary Report on Patentability for International (PCT) Patent Application No. PCT/US2010/031460, dated Oct. 27, 2011 7 pages.
English Translation of Official Action for China Patent Application No. 201080026166.0, dated Mar. 5, 2013 7 pages.
Official Action for European Patent Application No. 10715632.5, dated Jun. 26, 2013 4 pages.
Nam et al. "Different Contribution of Co-Stimulatory Molecules B7.1 and B7.2 to the Immune Response to Recombinant Modified Vaccinia Virus Ankara Vaccine Expressing Prm/E Proteins of Japanese Encephalitis Virus and Two Hepatitis B Virus Vaccines," Acta Virologica, 2007, vol. 51, No. 2, pp. 125-130, (Abstract), 1 page.
English Translation of Official Action for China Patent Application No. 201080026166.0, dated Jan. 21, 2014 7 pages.
Official Action with English Translation for Japan Patent Application No. 2012-505977, dated May 27, 2014 6 pages.
Official Action for European Patent Application No. 10715632.5, dated Feb. 25, 2015 5 pages.
Notice of Allowance with English Translation for Japan Patent Application No. 2012-505977, dated May 19, 2015 2 pages.
Official Action for Australian Patent Application No. 2010236206 dated Oct. 8, 2015, 6 pages.
English Translation of Official Action for China Patent Application No. 201080026166.0, dated Jun. 30, 2015 5 pages.
Grosenbach et al., "Synergy of Vaccine Strategies to Amplify Antigen-specific Immune Responses and Antitumor Effects," Cancer Research, 2001, vol. 61, Iss. 11, pp. 4497-4505.
Official Action for Australian Patent Application No. 2010236206 dated Sep. 23, 2016, 3 pages.
Notice of Acceptance for Australian Patent Application No. 2010236206 dated Oct. 11, 2016, 1 page.

(56) References Cited

OTHER PUBLICATIONS

Official Action (no English translation available) for Korean Patent Application No. 10-2011-7027319 dated Aug. 20, 2016, 10 pages.
Garnett et al., "TRICOM Vector Based Cancer Vaccines," Current Pharmaceutical Design, 2006, vol. 12, Iss. 3, pp. 351-361.
Official Action for European Patent Application No. 10715632.5, dated Jun. 8, 2016, 5 pages.
Official Action (with English translation) for Korean Patent Application No. 10-2017-7026393 dated Sep. 19, 2018, 6 pages.
Official Action (with English translation) for Korean Patent Application No. 10-2017-7026393 dated Nov. 1, 2018, 11 pages.
English Translation of Official Action for China Patent Application No. 201080026166.0, dated Oct. 11, 2014 10 pages.
Official Action for Canadian Patent Application No. 2,759,013 dated Mar. 18, 2016, 5 pages.
Official Action for Canadian Patent Application No. 2,759,013 dated Apr. 5, 2018, 5 pages.
English Translation of Official Action for China Patent Application No. 201080026166.0, dated Mar. 10, 2016, 3 pages.
Notice of Allowance (with English translation) for China Patent Application No. 201080026166.0, dated Aug. 17, 2016, 5 pages.
Notice of Intention to Grant for European Patent Application No. 10715632.5, dated Jul. 28, 2017, 7 pages.
Extended European Search Report for European Patent Application No. 17203871.3 dated Feb. 15, 2018, 8 pages.
Official Action (English translation) for Korean Patent Application No. 10-2011-7027319 dated Aug. 20, 2016, 6 pages.
Notice of Allowance (English translation) for Korean Patent Application No. 10-2011-7027319 dated Jun. 19, 2017, 3 pages.
Official Action (with English translation) for Korean Patent Application No. 10-2017-7026393 dated Jan. 2, 2018, 15 pages.
Official Action for Canadian Patent Application No. 2,759,013 dated Mar. 27, 2019, 4 pages.
Notice of Allowance (with English translation) for Korean Patent Application No. 10-2017-7026393 dated May 31, 2019, 3 pages.

\* cited by examiner

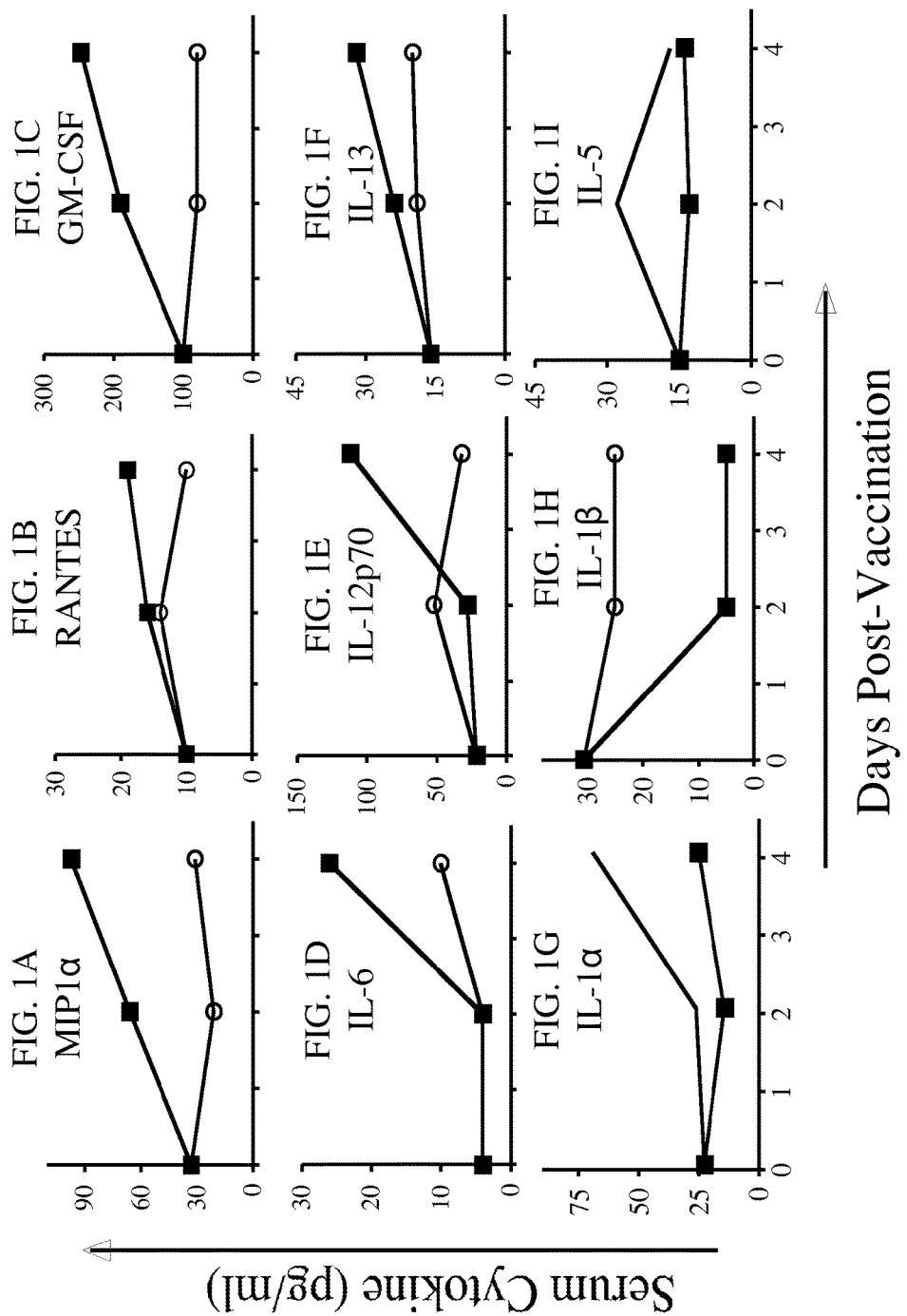

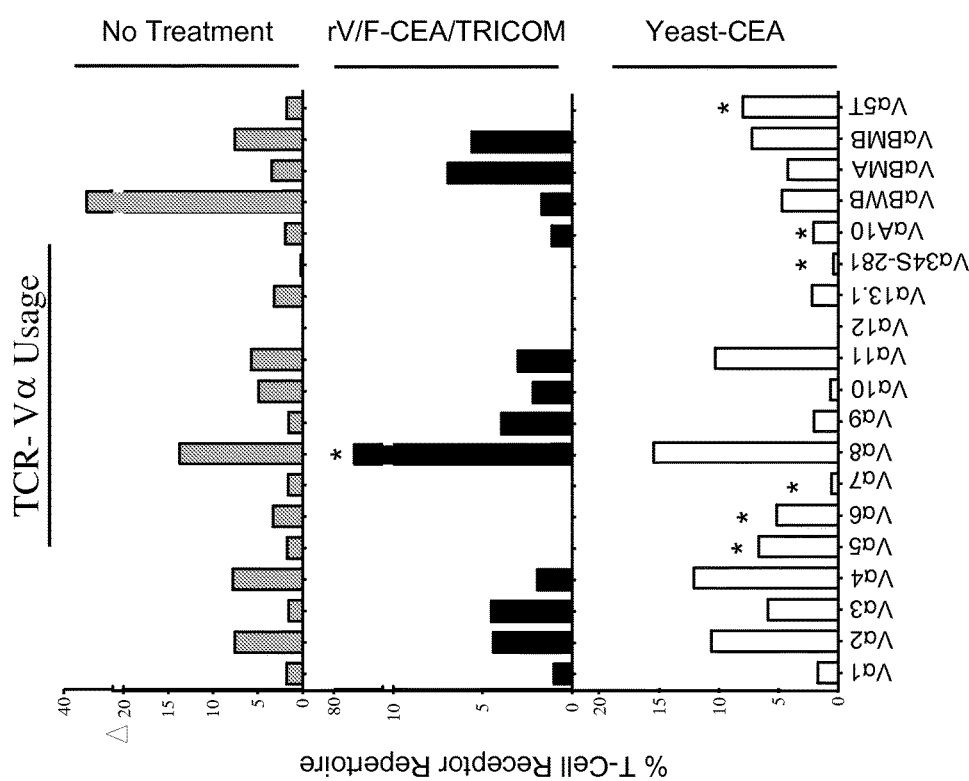

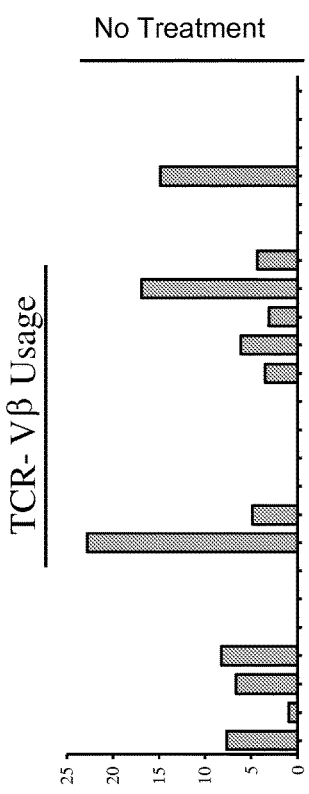
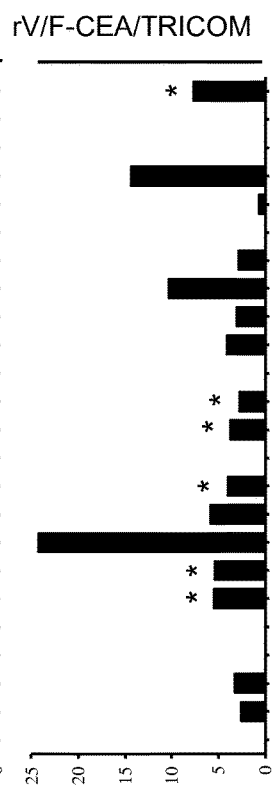
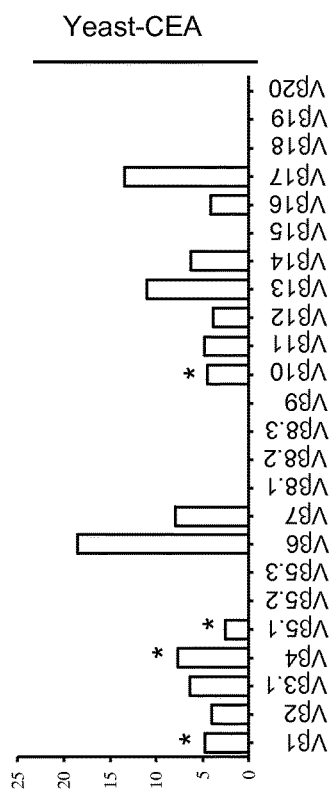

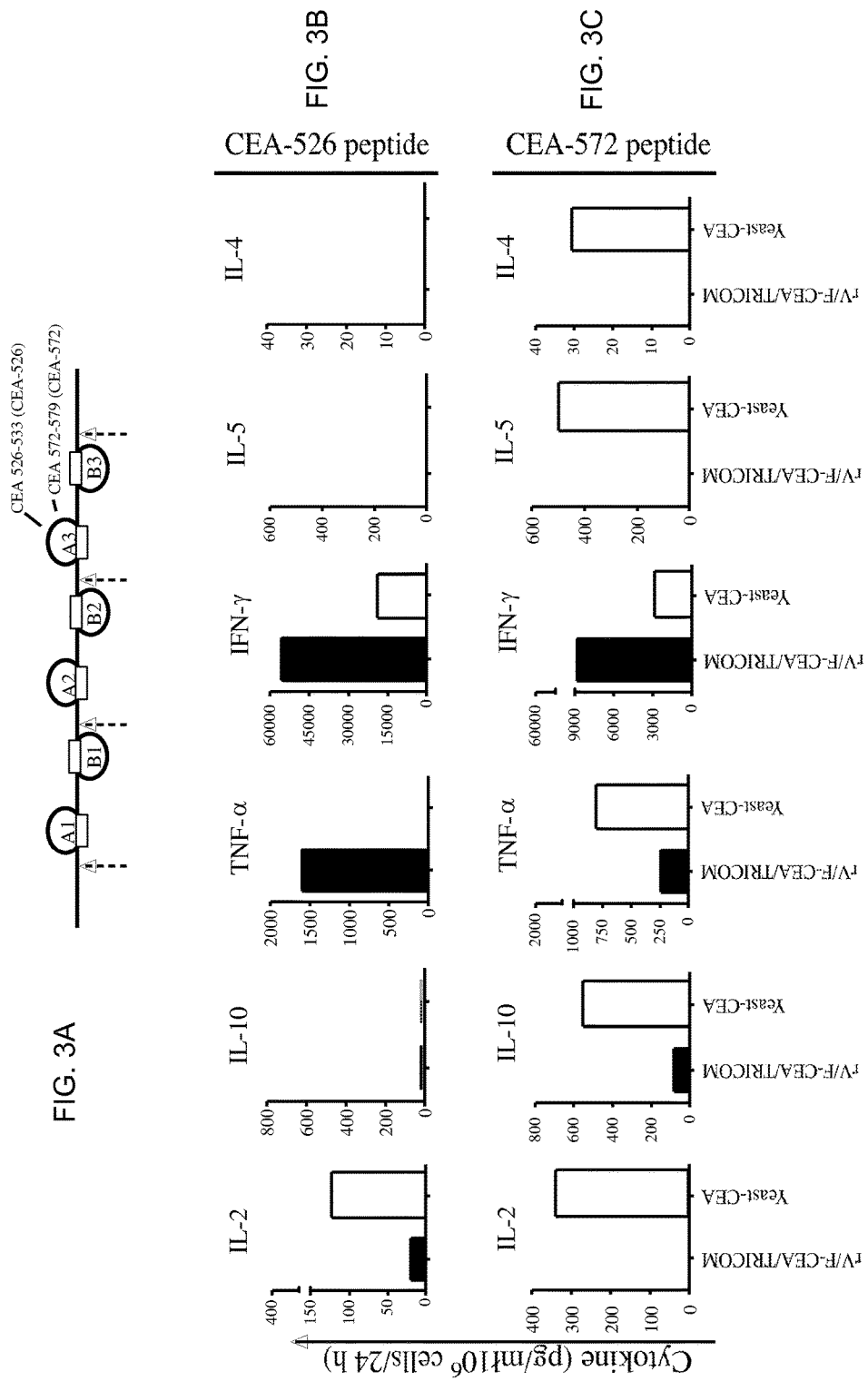

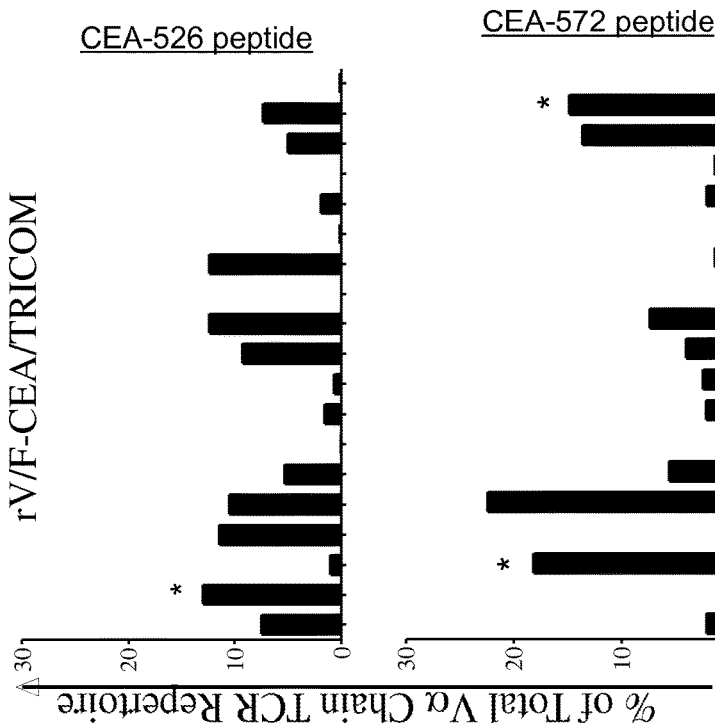
FIG. 4A
FIG. 4B

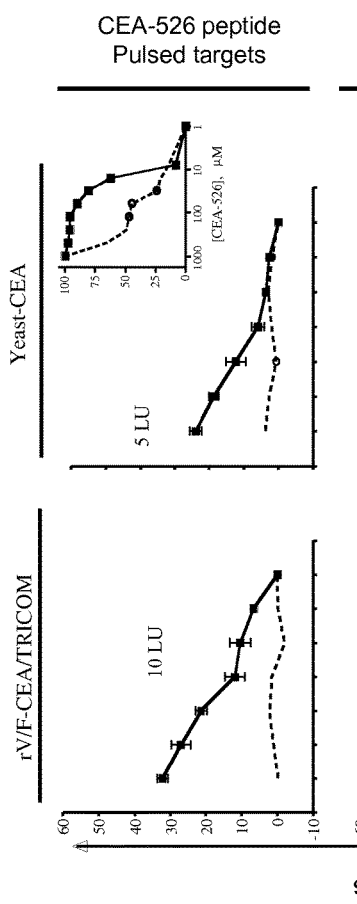
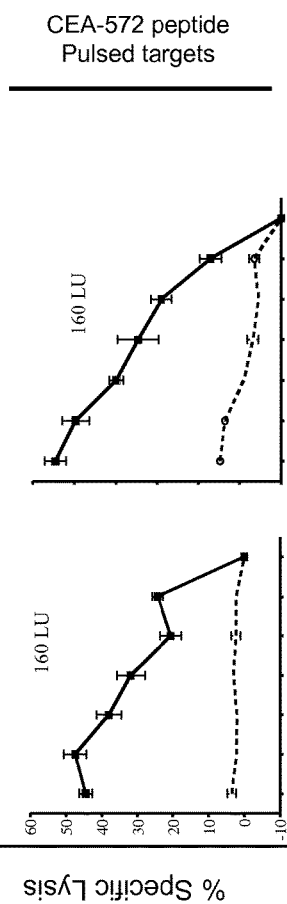
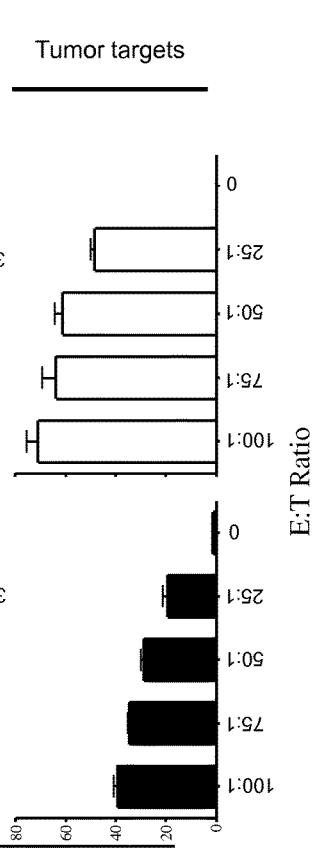
FIG. 5A  FIG. 5B  FIG. 5C  FIG. 5D  FIG. 5E  FIG. 5F

COMBINATION IMMUNOTHERAPY COMPOSITIONS AGAINST CANCER AND METHODS

CROSS-REFERENCE TO RELATED APPLICATIONS

This application is a national stage application under 35 U.S.C. 371 of PCT Application No. PCT/US2010/031460, filed Apr. 16, 2010, which claims the benefit of priority under 35 U.S.C. § 119(e) from U.S. Provisional Patent Application No. 61/170,530, filed Apr. 17, 2009.

GOVERNMENT RIGHTS

This invention was created in the performance of a Cooperative Research and Development Agreement with the National Institutes of Health, an Agency of the Department of Health and Human Services. The Government of the United States has certain rights in this invention.

REFERENCE TO SEQUENCE LISTING

This application contains a Sequence Listing submitted as an electronic text file named "3923-24-PCT_ST25.txt", having a size in bytes of 47 KB, and created on Apr. 16, 2010. The information contained in this electronic file is hereby incorporated by reference in its entirety pursuant to 37 CFR § 1.52(e)(5).

STATEMENT REGARDING JOINT RESEARCH AGREEMENT

This invention was made by or on behalf of parties to a Cooperative Research and Development Agreement, executed May 8, 2008. The parties to the Cooperative Research and Development Agreement are: GlobeImmune, Inc. and the U.S. Department of Health and Human Services, as represented by National Cancer Institute, an Institute, Center or Division of the National Institutes of Health.

REFERENCE TO A SEQUENCE LISTING

This application contains a Sequence Listing submitted electronically as a text file by EFS-Web. The text file, named "3923-24-PCT_ST25", has a size in bytes of 47 KB, and was recorded on 16 Apr. 2010. The information contained in the text file is incorporated herein by reference in its entirety pursuant to 37 CFR § 1.52(e)(5).

FIELD OF THE INVENTION

The present invention generally relates to the concurrent use of two different immunotherapeutic compositions for the improved induction of therapeutic immune responses and/or for the prevention, amelioration and/or treatment of disease, including, but not limited to, cancer and infectious disease.

BACKGROUND OF THE INVENTION

Immunotherapeutic compositions, including vaccines, are one of the most cost-effective measures available to the health care industry for the prevention and treatment of disease. There remains, however, an urgent need to develop safe and effective immunotherapy strategies and adjuvants for a variety of diseases, including those caused by or associated with infection by pathogenic agents, cancers, genetic defects and other disorders of the immune system. For the treatment of cancer and many infectious diseases, including viral diseases and diseases caused by intracellular pathogens, it is desirable to provide immunotherapy that elicits a cell-mediated (cellular) immune response, although many vaccines are directed primarily or entirely to elicitation of humoral immunity. Indeed, a disadvantage of many subunit vaccines, as well as many killed or attenuated pathogen vaccines, is that while they appear to stimulate a strong humoral immune response, they fail to elicit protective cell-mediated immunity.

Cancer is a leading cause of death worldwide, and the development of effective therapies for cancer continues to be one of the most active areas of research. Although a variety of innovative approaches to treat and prevent cancers have been proposed, many cancers continue to have a high rate of mortality and may be difficult to treat or relatively unresponsive to conventional therapies. Novel discoveries in cancer biology have provided the opportunity to design target-specific anti-cancer agents and have fostered advances in drug and immunotherapy development. These discoveries make it possible to design molecules and therapeutic compositions with high selectivity against specific targets in cancer cells.

Numerous immunotherapy studies have been reported comparing vaccine platforms that target the same antigen, in terms of their ability to induce immune cell activity and antitumor effects (e.g., see Weide et al., Immunol Lett 2008 Jan. 15; 115(1):33-42; Riezebos-Brilman et al., Gene Ther 2007 December; 14(24):1695-704; Naslund et al., J Immunol 2007 Jun. 1; 178(11):6761-9; Mylin et al., J Virol 2000 August; 74(15):6922-34; Millar et al., Cell Immunol 2007 November-December; 250(1-2):55-67; Hodge et al., Cancer Res 2003 Nov. 15; 63(22):7942-9; Chan et al., Gene Ther 2006 October; 13(19):1391-402; Casimiro et al., J Virol 2003 June; 77(11):6305-13; and Bos et al., J Immunol 2007 Nov. 1; 179(9):6115-22). Millar et al. showed that the functionality of T-cell populations induced by two different vectors (rV and recombinant adenovirus) targeting the same antigen did not differ (Millar et al., Cell Immunol 2007 November-December; 250(1-2):55-67).

The antitumor efficacy of the diversified prime and boost vaccine regimen of recombinant vaccinia (rV) and recombinant fowlpox (rF) viruses containing murine B7-1, ICAM-1, and LFA-3 genes as well as the human carcinoembryonic antigen (CEA) gene (rV/F-CEA/TRICOM) has previously been reported in preclinical models (Hodge et al., Cancer Res 2003 Nov. 15; 63(22):7942-9; Hodge et al., Cancer Res 1999 Nov. 15; 59(22):5800-7; Hodge et al., Clin Cancer Res 2003 May; 9(5):1837-49; Grosenbach et al., Cancer Res 2001 Jun. 1; 61(11):4497-505; Greiner et al., Cancer Res 2002 Dec. 1; 62(23):6944-51; Arlen et al., Crit Rev Immunol 2007; 27(5):451-62). Recently, the antitumor effects of a recombinant *Saccharomyces cerevisiae* (yeast-CEA) vaccine were also documented in preclinical models (Bernstein et al., Vaccine 2008 Jan. 24; 26(4):509-21; Wansley et al., Clin Cancer Res 2008 July 1; 14(13):4316-25). The induction of immune response after vaccination with either rV/FCEA/TRICOM or yeast-CEA has been documented, and the antitumor effects elicited by either vaccine are mainly attributed to the induction of CEA-specific T-cell populations.

Several studies have documented that the induction of a more diverse T-cell population is advantageous in mounting an immune response in various models of disease, including cancer (Dudley et al., Cancer J 2000 March-April; 6(2):69-77; Dutoit et al., Cancer Res 2001 Aug. 1; 61(15):5850-6;

Echchakir et al., *Int Immunol* 2000 April; 12(4):537-46; Ferradini et al., *Cancer Res* 1992 Sep. 1; 52(17):4649-54; Messaoudi et al., *Science* 2002 Nov. 29; 298(5599):1797-800; Nikolich-Zugich et al., *Nat Rev Immunol* 2004 February; 4(2):123-32; Sportes et al., *J Exp Med* 2008 Jul. 7; 205(7):1701-14; Zhou et al., *Cancer Res* 2005 Feb. 1; 65(3):1079-88). However, there are no reports of concurrent use of vaccines that target the same antigen. Following studies targeting the same antigen, such as those described above, investigators historically either choose the most efficacious vaccine for further study, or employ a diversified prime and boost strategy to amplify the T-cell response. For example, a diversified prime-boost vaccination strategy with recombinant vaccinia and fowlpox vectors targeting CEA (Hodge et al., *Vaccine* 1997 April-May; 15(6-7):759-68; Marshall et al., *J Clin Oncol* 2000 Dec. 1; 18(23):3964-73), was employed because the immune response to the first vaccine has been shown to reduce the effects of subsequent vaccinations with the same vector (Naslund et al., 2007, supra; Grosenbach et al., 2001, supra, Hodge et al., 1997, supra, and Wu et al., *J Virol* 2005 July; 79(13):8024-31.). Similar results demonstrating the clear advantages of a diversified prime-boost strategy have been described in a variety of cancer and other disease models, including HIV and malaria (Wu et al, 2005, supra; Pancholi et al., *J Infect Dis* 2000 July; 182(1):18-27; Barnett et al., AIDS Res Hum Retroviruses 1998 October; 14 Suppl 3:S299-309; Dunachie et al., *J Exp Biol* 2003 November; 206(Pt 21):3771-9; McMichael, *Annu Rev Immunol* 2006; 24:227-55; Moore et al., *Immunol Rev* 2004 June; 199:126-43). The enhanced responses observed in these studies have been attributed to amplification of the relevant population of antigen-specific T-cells, but again, a diversified prime-boost approach was used to achieve these results.

Accordingly, despite advances in cancer therapy and infectious disease immunotherapy/vaccine technology, there remains an urgent need to improve safe and effective immunotherapy approaches to the treatment such diseases.

SUMMARY OF THE INVENTION

One embodiment of the invention relates to a method to prevent, ameliorate or treat at least one symptom of a cancer in an individual, to increase survival of an individual with cancer, and/or to induce a therapeutic immune response against one or more cancer antigens in the individual. The method includes the step of administering to the individual: (a) a first immunotherapy composition comprising a recombinant vaccinia virus comprising nucleic acid sequences encoding at least one costimulatory molecule and nucleic acid sequences encoding at least one cancer antigen or immunogenic domain thereof; and (b) a second immunotherapy composition comprising a yeast vehicle comprising at least one cancer antigen or immunogenic domain thereof. The first and second immunotherapy compositions are administered concurrently to the individual. In one aspect, the recombinant vaccinia virus comprises nucleic acid sequences encoding costimulatory molecules B7-1, ICAM-1 and LFA-3.

Another embodiment of the invention relates to a method to prevent, ameliorate or treat at least one symptom of a cancer in an individual, to increase survival of an individual with cancer, and/or to induce a therapeutic immune response against one or more cancer antigens in the individual. The method includes a step of administering to the individual: (a) a first immunotherapy composition comprising: (i) a recombinant vaccinia virus comprising nucleic acid sequences encoding B7-1, ICAM-1 and LFA-3 or biologically active portions thereof, and a nucleic acid sequence encoding at least one cancer antigen or immunogenic domain thereof; and (ii) a recombinant fowlpox virus comprising a nucleic acid sequence encoding GM-CSF or a biologically active portion thereof; and (b) a second immunotherapy composition comprising a yeast vehicle comprising at least one cancer antigen or immunogenic domain thereof. The first and second immunotherapy compositions are administered concurrently to the individual. In one aspect of this embodiment, at least one week after the first administration, the method additionally includes the step of administering to the individual: (a) a third immunotherapy composition comprising: (i) a recombinant fowlpox virus comprising nucleic acid sequences encoding B7-1, ICAM-1 and LFA-1 or biologically active portions thereof, and a nucleic acid sequence encoding the at least one cancer antigen or immunogenic domain thereof; and (ii) a recombinant fowlpox virus comprising a nucleic acid sequence encoding GM-CSF or a biologically active portion thereof; and (b) the second immunotherapy composition comprising a yeast vehicle comprising the at least one cancer antigen or immunogenic domain thereof. The second and third immunotherapy compositions are administered concurrently to the individual.

Yet another embodiment of the invention relates to the use of a combination of immunotherapy compositions in the preparation of medicaments for concurrent administration to an individual to prevent, ameliorate or treat at least one symptom of cancer in the individual, or to increase survival of an individual who has cancer, and/or to induce a therapeutic immune response against one or more antigens in the individual. The immunotherapy compositions comprise: (a) a first immunotherapy composition comprising: (i) a recombinant vaccinia virus comprising nucleic acid sequences encoding B7-1, ICAM-1 and LFA-3 or biologically active portions thereof, and nucleic acid sequences encoding at least one cancer antigen or immunogenic domain thereof; and (ii) a recombinant fowlpox virus comprising a nucleic acid sequence encoding GM-CSF or a biologically active portion thereof; and (b) a second immunotherapy composition comprising a yeast vehicle comprising at least one cancer antigen or immunogenic domain thereof. In one aspect, the immunotherapy compositions further comprise a third immunotherapy composition comprising: (i) a recombinant fowlpox virus comprising nucleic acid sequences encoding B7-1, ICAM-1 and LFA-3 or biologically active portions thereof, and nucleic acid sequences encoding the at least one cancer antigen or immunogenic domain thereof; and (ii) a recombinant fowlpox virus comprising a nucleic acid sequence encoding GM-CSF or a biologically active portion thereof.

One embodiment of the invention relates to a method to prevent, ameliorate or treat at least one symptom of a disease or condition in an individual. The method includes a step of administering to the individual: (a) a first immunotherapy composition comprising a recombinant virus comprising the virus genome or portions thereof; and (b) a second immunotherapy composition comprising a yeast vehicle. The first and second immunotherapy compositions are administered concurrently to the individual.

Another embodiment of the invention relates to a method to induce a therapeutic immune response against one or more antigens in an individual. The method includes the step of administering to the individual: (a) a first immunotherapy composition comprising a recombinant virus comprising the virus genome or portions thereof; and (b) a second immunotherapy composition comprising a yeast vehicle. The first and second immunotherapy compositions are administered concurrently to the individual.

Another embodiment of the invention relates to a method to increase survival of an individual who has a disease or condition. The method includes a step of administering to the individual: (a) a first immunotherapy composition comprising a recombinant virus comprising the virus genome or portions thereof; and (b) a second immunotherapy composition comprising a yeast vehicle. The first and second immunotherapy compositions are administered concurrently to the individual.

Yet another embodiment of the invention relates to the use of a combination of immunotherapy compositions in the preparation of medicaments for concurrent administration to an individual to prevent, ameliorate or treat at least one symptom of a disease or condition in the individual. The immunotherapy compositions include: (a) a first immunotherapy composition comprising a recombinant virus comprising the virus genome or portions thereof; and (b) a second immunotherapy composition comprising a yeast vehicle. The compositions are formulated for concurrent administration.

Another embodiment of the invention relates to the use of a combination of immunotherapy compositions in the preparation of medicaments for concurrent administration to an individual to induce a therapeutic immune response against one or more antigens in the individual. The immunotherapy compositions comprise: (a) a first immunotherapy composition comprising a recombinant virus comprising the virus genome or portions thereof; and (b) a second immunotherapy composition comprising a yeast vehicle. One or both of the first and second immunotherapy compositions comprises at least one antigen or immunogenic domain thereof. The compositions are formulated for concurrent administration.

Yet another embodiment of the invention relates to the use of a combination of immunotherapy compositions in the preparation of medicaments for concurrent administration to an individual who has a disease or condition to increase survival of the individual. The immunotherapy compositions comprise: (a) a first immunotherapy composition comprising a recombinant virus comprising the virus genome or portions thereof; and (b) a second immunotherapy composition comprising a yeast vehicle. One or both of the first and second immunotherapy compositions comprises at least one antigen or immunogenic domain thereof. The compositions are formulated for concurrent administration.

Yet another embodiment of the invention relates to a composition comprising: (a) a first immunotherapy composition comprising a recombinant virus comprising the virus genome or portions thereof; and (b) a second immunotherapy composition comprising a yeast vehicle. One or both of the first and second immunotherapy compositions comprises at least one antigen or immunogenic domain thereof. The first and second immunotherapy compositions are provided in admixture.

Another embodiment of the invention relates to a kit comprising the following immunotherapy compositions: (a) a first immunotherapy composition comprising a recombinant vaccinia virus comprising nucleic acid sequences encoding at least one costimulatory molecule and nucleic acid sequences encoding at least one antigen or immunogenic domain thereof; and (b) a second immunotherapy composition comprising a yeast vehicle comprising at least one antigen or immunogenic domain thereof. In one aspect, the recombinant vaccinia virus comprises nucleic acid sequences encoding costimulatory molecules B7-1, ICAM-1 and LFA-3. In one aspect, the antigen is a cancer antigen. In one aspect, the antigen is a modified CEA comprising a CAP-1-6D epitope. Other aspects of the kit of the invention are described below.

Another embodiment of the invention relates to a kit comprising the following immunotherapy compositions: (a) a first immunotherapy composition comprising: (i) a recombinant vaccinia virus comprising nucleic acid sequences encoding B7-1, ICAM-1 and LFA-3 or biologically active portions thereof, and a nucleic acid sequence encoding at least one antigen or immunogenic domain thereof; and (ii) a recombinant fowlpox virus comprising a nucleic acid sequence encoding GM-CSF or a biologically active portion thereof; and (b) a second immunotherapy composition comprising a yeast vehicle comprising at least one antigen or immunogenic domain thereof. In one aspect, the kit further comprises a third immunotherapy composition comprising: (i) a recombinant fowlpox virus comprising nucleic acid sequences encoding B7-1, ICAM-1 and LFA-3 or biologically active portions thereof, and a nucleic acid sequence encoding the at least one antigen or immunogenic domain thereof; and (ii) a recombinant fowlpox virus comprising a nucleic acid sequence encoding GM-CSF or a biologically active portion thereof. In one aspect, the antigen is a cancer antigen. In one aspect, the antigen is a modified CEA comprising a CAP-1-6D epitope. Other aspects of the kit of the invention are described below.

In any of the embodiments described herein (above or below), including any of the embodiments related to a method, use, composition or kit of the invention, one or both of the first and second immunotherapy compositions (and/or third immunotherapy composition, in particular embodiments) comprises at least one antigen or immunogenic domain thereof. In one aspect, both the first and second immunotherapy compositions (and/or third immunotherapy composition, in particular embodiments) comprise at least one antigen or immunogenic domain thereof. In one aspect, the first immunotherapy composition comprises at least one antigen or immunogenic domain thereof, and the second does not. In one aspect, the second immunotherapy composition comprises at least one antigen or immunogenic domain thereof, and the first does not. In one aspect, each of the first and second immunotherapy compositions comprises the same antigen or immunogenic domain thereof. In one aspect, the first and second immunotherapy compositions (and/or third immunotherapy composition, in particular embodiments) comprise different antigens or immunogenic domains thereof.

In one aspect of any of the embodiments or aspects of the invention described herein (above or below), including any of the embodiments related to a method, use, composition or kit of the invention, the first and/or third immunotherapy composition comprises a recombinant virus comprising one or more nucleic acid sequences encoding one or more immunostimulatory molecules. In one aspect, the first and/or third immunotherapy composition comprises a recombinant virus comprising the virus genome or portions thereof and a nucleic acid sequence encoding at least one antigen or immunogenic domain thereof, and a recombinant virus comprising one or more nucleic acid sequences encoding one or more immunostimulatory molecules. In one aspect, the first and/or third immunotherapy composition comprises a recombinant virus comprising a nucleic acid sequence encoding the at least one antigen or immunogenic domain thereof and one or more nucleic acid sequences encoding one or more immunostimulatory molecules.

In one aspect of any of the embodiments or aspects of the invention described herein (above or below), including any of the embodiments related to a method, use, composition or kit of the invention, the recombinant virus or viruses in the first and/or third immunotherapy composition is a poxvirus. In one aspect, the recombinant virus or viruses in the first and/or third immunotherapy composition is a recombinant vaccinia virus. In one aspect, the vaccinia virus is modified vaccinia Ankara (MVA). In one aspect, the recombinant virus or viruses in the first and/or third immunotherapy composition is a fowlpox virus.

In one aspect of any of the embodiments or aspects of the invention described herein (above or below), including any of the embodiments related to a method, use, composition or kit of the invention, the immunostimulatory molecules comprise one or more costimulatory molecules. In one aspect, the immunostimulatory molecules include, but are not limited to, B7.1 (B7-1), B7.2 (B7-2), ICAM-1, LFA-3, 4-1BBL, CD59, CD40, CD40L and/or CD70. In one aspect, the immunostimulatory molecules comprise one, two or all three of B7-1, ICAM-1, and LFA-3. In one aspect, the immunostimulatory molecules comprise one or more cytokines, including, but not limited to, tumor necrosis factor-α (TNF-α), interleukin-6 (IL-6), granulocyte-macrophage-colony stimulating factor (GM-CSF), interferon-γ (IFN-γ), IFN-α, IFN-λ, interleukin-12 (IL-12), RANTES, and interleukin-2 (IL-2). In one aspect, the cytokine is granulocyte-macrophage colony-stimulating factor (GM-CSF).

In one aspect of any of the embodiments or aspects of the invention described herein (above or below), including any of the embodiments related to a method, use, composition or kit of the invention, the second immunotherapy composition comprises a yeast vehicle that expresses at least one antigen or immunogenic domain thereof. In one aspect, the yeast vehicle in the second immunotherapy composition is a whole yeast. In one aspect, the yeast vehicle in the second immunotherapy composition is a whole, heat-killed yeast. In one aspect, the yeast vehicle in the second immunotherapy composition is from *Saccharomyces*.

In one aspect of any of the method or use embodiments or aspects of the invention described herein (above or below), the first and second immunotherapy compositions (and/or third immunotherapy composition in certain embodiments) are administered to different sites in the individual. In another aspect, the first and second (and/or third) immunotherapy compositions are administered to the same site or to adjacent sites in the individual.

In another aspect of any of the method or use embodiments or aspects of the invention described herein (above or below), the method or use further comprises a step of boosting the individual with one or both (or all three, in certain embodiments) of the immunotherapy compositions. In one aspect, the individual is boosted with the second immunotherapy composition more frequently than with the first immunotherapy composition.

In another aspect of any of the method or use embodiments or aspects of the invention described herein (above or below), wherein there is a first and second immunotherapy composition, the method or use further comprises a step of boosting the individual with a third immunotherapy composition comprising a recombinant virus comprising the virus genome or portions thereof that is different from the first immunotherapy composition. For example, in one aspect, the first immunotherapy composition comprises a recombinant vaccinia virus, and the third immunotherapy composition comprises a fowlpox virus.

In one aspect of any of the embodiments or aspects of the invention described herein, including any of the embodiments related to a method, use, composition or kit of the invention, either the first or the second immunotherapy composition is administered more frequently than the other. For example, in one aspect, when the first immunotherapy composition is a virus-based immunotherapy composition, and the second immunotherapy composition is a yeast-based immunotherapy composition, the second immunotherapy composition may be administered more frequently than the first immunotherapy composition. For example, in one aspect, in between concurrent administrations of the first and second immunotherapy composition, the second immunotherapy composition may be administered one, two, three or more additional times.

In another aspect of any of the method or use embodiments or aspects of the invention described herein (above or below), the method further comprises a step of boosting the individual with another source of the antigen or immunogenic domain thereof.

In another aspect of any of the method or use embodiments or aspects of the invention described herein (above or below), the method further comprises a step of administering at least one biological response modifier to the individual.

In one aspect of any of the embodiments or aspects of the invention described herein (above or below), including any of the embodiments related to a method, use, composition or kit of the invention, the individual has cancer. In one aspect, the method or use reduces tumor burden or inhibits tumor growth in the individual. In one aspect of any embodiment of the invention, including any of the embodiments related to a method, use, composition or kit of the invention, the antigen is from a cancer selected from the group of: melanomas, squamous cell carcinoma, breast cancers, head and neck carcinomas, thyroid carcinomas, soft tissue sarcomas, bone sarcomas, testicular cancers, prostatic cancers, ovarian cancers, bladder cancers, skin cancers, brain cancers, angiosarcomas, hemangiosarcomas, mast cell tumors, leukemias, lymphomas, primary hepatic cancers, lung cancers, pancreatic cancers, gastrointestinal cancers, renal cell carcinomas, hematopoietic neoplasias or metastatic cancers thereof. In one aspect, the antigen is selected from the group of: carcinoembryonic antigen (CEA), point mutated Ras oncoprotein, Brachyury, MUC-1, EGFR, BCR-Ab1, MART-1, MAGE-1, MAGE-3, GAGE, GP-100, MUC-2, normal and point mutated p53 oncoproteins, PSMA, tyrosinase, TRP-1 (gp75), NY-ESO-1, TRP-2, TAG72, KSA, CA-125, PSA, HER-2/neu/c-erb/B2, hTERT, p'73, B-RAF, adenomatous polyposis coli (APC), Myc, von Hippel-Lindau protein (VHL), Rb-1, Rb-2, androgen receptor (AR), Smad4, MDR1, Flt-3, BRCA-1, BRCA-2, pax3-fkhr, ews-fli-1, HERV-H, HERV-K, TWIST, Mesothelin, NGEP, modifications of such antigens, splice variants of such antigens, and epitope agonists of such antigens, as well as combinations of such antigens, and/or immunogenic domains thereof, modifications thereof, variants thereof, and/or epitope agonists thereof. In one aspect, the antigen is carcinoembryonic antigen (CEA), which in one embodiment, comprises a CAP1-6D epitope. In one aspect, the antigen is a modified CEA comprising a CAP-1-6D epitope. In one aspect, the CEA comprises an amino acid sequence of SEQ ID NO:2 (encoded by a nucleic acid sequence represented herein as SEQ ID NO:1). In another aspect, the antigen is mutated Ras. In one aspect, the antigen is a multi-domain fusion protein, comprising one or more fragments of Ras, each fragment comprising one or more mutations at position 12, 13, 59, 61 and/or 76 of Ras. In one aspect, the Ras fusion protein has an amino acid sequence of SEQ ID NO:4 (encoded by a nucleic acid sequence represented herein as SEQ ID NO:3), SEQ ID NO:6 (encoded by a nucleic acid sequence represented herein as SEQ ID NO:5), SEQ ID NO:8 (encoded by a nucleic acid sequence represented herein as SEQ ID NO:7), and/or SEQ ID NO:10 (encoded by a nucleic acid sequence represented herein as SEQ ID NO:9). In one aspect, the antigen is Brachyury. In one aspect, the antigen is MUC-1. In one aspect, the antigen is EGFR. In one aspect, the antigen is BCR-Ab1.

In one aspect of any of the method or use embodiments or aspects of the invention described herein (above or below), the method or use further includes a step of treating the individual with chemotherapy, and/or treating the individual with radiation therapy.

In another aspect of any of the embodiments or aspects of the invention described herein (above or below), including any of the embodiments related to a method, use, composition or kit of the invention, the individual has a disease caused by or associated with a pathogen. In one aspect, the method or use reduces or prevents infection of the individual by the pathogen. In one aspect, the method or use reduces pathogen titer in the individual.

In one aspect of any embodiment of the invention, including any of the embodiments related to a method, use, composition or kit of the invention, the antigen is selected from the group of: viral antigens, fungal antigens, bacterial antigens, helminth antigens, parasitic antigens, ectoparasite antigens, and protozoan antigens. In one aspect, the antigen is from a virus selected from: adenoviruses, arena viruses, bunyaviruses, coronaviruses, coxsackie viruses, cytomegaloviruses, Epstein-Barr viruses, flaviviruses, hepadnaviruses, hepatitis viruses, herpes viruses, influenza viruses, lentiviruses, measles viruses, mumps viruses, myxoviruses, oncogenic viruses, orthomyxoviruses, papilloma viruses, papovaviruses, parainfluenza viruses, paramyxoviruses, parvoviruses, picornaviruses, pox viruses, rabies viruses, respiratory syncytial viruses, reoviruses, rhabdoviruses, rubella viruses, togaviruses, varicella viruses, and T-lymphotrophic viruses. In one aspect, the antigen is from an infectious agent from a genus selected from the group consisting of: *Aspergillus, Bordatella, Brugia, Candida, Chlamydia, Coccidia, Cryptococcus, Dirofilaria, Escherichia, Francisella, Gonococcus, Histoplasma, Leishmania, Mycobacterium, Mycoplasma, Paramecium, Pertussis, Plasmodium, Pneumococcus, Pneumocystis, Rickettsia, Salmonella, Shigella, Staphylococcus, Streptococcus, Toxoplasma, Vibriocholerae,* and *Yersinia*. In one aspect, the antigen is from a bacterium from a genus selected from: *Pseudomonas, Bordetella, Mycobacterium, Vibrio, Bacillus, Salmonella, Francisella, Staphylococcus, Streptococcus, Escherichia, Enterococcus, Pasteurella,* and *Yersinia*.

BRIEF DESCRIPTION OF THE FIGURES OF THE INVENTION

FIGS. 1A-1I are graphs showing that vaccination with rV-CEA/TRICOM or yeast-CEA induces differential serum cytokine profiles (FIG. 1A=MIP1α, FIG. 1B=RANTES, FIG. 1C=GM-CSF, FIG. 1D=IL-6, FIG. 1E=IL-12p70, FIG. 1F=IL-13, FIG. 1G=IL-1α, FIG. 1H=IL-1β and FIG. 1I=IL-5.

FIGS. 2A-2G show that distinct TCR repertoires are induced from vaccination with rV/F-CEA/TRICOM or yeast-CEA (Vα profiles are shown for no treatment (FIG. 2A), rV/F-CEA/TRICOM (FIG. 2B), and yeast-CEA (FIG. 2C), and Vβ profiles are shown for no treatment (FIG. 2D), rV/F-CEA/TRICOM (FIG. 2E), and yeast-CEA (FIG. 2F).

FIG. 3A shows the discrete, non-overlapping CEA-526 and CEA-572 epitopes on the A3 loop of domain III of CEA.

FIGS. 3B-3C show that vaccination with rV/F-CEA/TRICOM or yeast-CEA induces distinct cytokine profiles in response to in vitro stimulation with two discrete CEA-specific epitopes, CEA-526 (FIG. 3B) and CEA-572 (FIG. 3C).

Figure 4C:
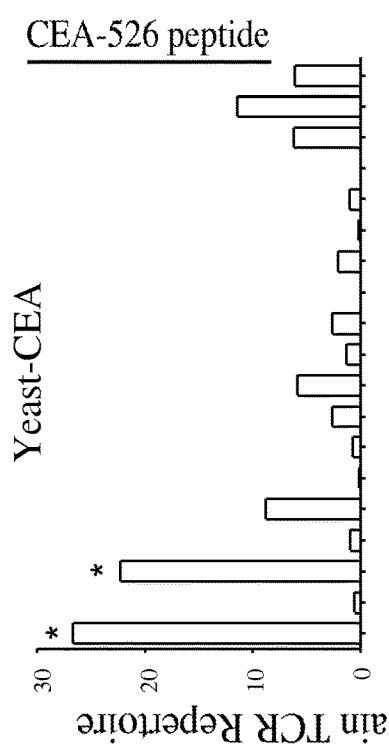

FIGS. 4A-4D show that T-cell lines specific for the CEA-572 epitope from mice vaccinated with rV/F-CEA/TRICOM or yeast-CEA have distinct TCR Vα profiles (Vα TCR repertoires of rV/F-CEA/TRICOM T-cell lines (black bars) maintained in the presence of CEA-526 peptide (FIG. 4A) and CEA-572 peptide (FIG. 4B); Vα TCR repertoires of yeast-CEA T cell lines (white bars) maintained in the presence of CEA-526 peptide (FIG. 4C) and CEA-572 peptide (FIG. 4D)).

FIGS. 5A-5F show that epitope-specific T-cell lines generated from mice vaccinated with rV/F-CEA/TRICOM or yeast-CEA have similar levels of lytic activity but unique avidity (FIGS. 5A and 5C show T cell lines generated from rV/F-CEA/TRICOM vaccination and specific for CEA-526 peptide (FIG. 5A) and CEA-572 peptide (FIG. 5C); FIGS. 5B and 5D show T-cell lines generated from yeast-CEA vaccination and specific for CEA-526 peptide (FIG. 5B) and CEA-572 peptide (FIG. 5D); FIGS. 5E and 5F show T-cell lines specific for CEA-572 epitope, generated from mice vaccinated with rV/F-CEA/TRICOM (FIG. 5E) or yeast-CEA (FIG. 5F)).

Figure 6:
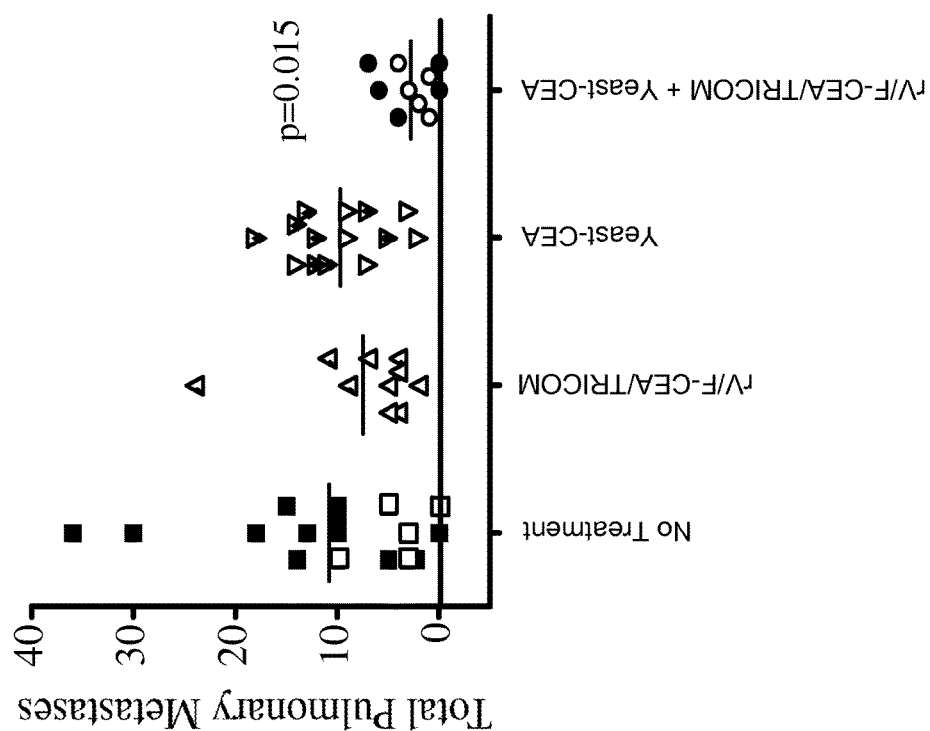

FIG. 6 shows that concurrently administering rV/F-CEA/TRICOM and yeast-CEA vaccines in an orthotopic pulmonary metastasis model increases antitumor efficacy.

DETAILED DESCRIPTION OF THE INVENTION

The present invention relates to the concurrent use of two immunotherapeutic compositions (also referred to herein as vaccines) for the induction of therapeutic immune responses and/or for the prevention, amelioration and/or treatment of disease, including, but not limited to, cancer and infectious disease. More specifically, using recombinant virus immunotherapeutic vaccines and yeast-based immunotherapeutic vaccines, each targeting the same antigen or immunogenic domain thereof, both the vaccine vectors and the antigen are demonstrated herein to have a role in the induction of T-cell populations having both shared and unique cytokine responses, gene expression profiles, and T-cell receptor phenotypes. Accordingly, both the antigen and the vector play a role in the induction of distinct T-cell populations. The studies presented herein indicate that phenotypically and functionally distinct T-cell populations are induced by two vector platforms targeting the same antigen. Finally, the inventors have demonstrated that the two vaccines can be combined concurrently to improve therapeutic efficacy, showing that the concurrent administration of the vaccines improved antitumor efficacy in the experiments described herein. These results indicate a therapeutic benefit from the concurrent administration of two distinct vector platforms targeting a single antigen, due to the induction of a more diverse T-cell population and improved therapeutic efficacy.

This study is believed to be the first to demonstrate effective concurrent administration of two different vaccine vectors targeting the same antigen. While it had been previously shown that each of the vaccines used in the studies described herein individually induce similar levels of CD4+

T-cell proliferation and CD8+ T-cell cytolytic activity (Wansley et al., Clin Cancer Res, 2008 Jul. 1; 14(13):4316-25), the discovery that these vaccines induce phenotypically and functionally distinct T-cell populations, and that the vaccines can be combined concurrently to substantially improve antitumor efficacy, was not known or anticipated.

In contrast to prior studies showing that the functionality of T-cell populations induced by two different vaccine platforms (rV and recombinant adenovirus) targeting the same antigen (OVA) did not differ (Millar et al., 2007, Cell Immunol 250(1-2):55-67), the present invention provides evidence that both the vector and the antigen affect the functionality of the T-cell population induced by two different immunotherapeutic vaccines, one a virus-based immunotherapy composition (referred to herein as rV-CEA/TRICOM) and one a yeast-based immunotherapy composition (referred to herein as yeast-CEA). Comparing the T-cell populations induced by both vaccines in terms of cytokine production, gene expression, and TCR profiling, the studies presented herein found that rV-CEA/TRICOM induces a Th1 response and CD8+ T-cells with a Tc1 phenotype, while yeast-CEA induces a mixed Th1/Th2 response and CD8+ T-cells with a mixed Tc1/Tc2 phenotype (FIGS. 1 and 3). Up-regulation of genes involved in immune cell migration and TCR signaling and T-cell proliferation was observed by both vaccines (Table 1). Interestingly, although these vaccines modulate the expression of genes involved in various cellular pathways in an apparent disadvantageous manner, antigen-specific immune responses or antitumor efficacy is not abrogated (Wansley et al., *Clin Cancer Res* 2008 Jul. 1; 14(13):4316-25). It is also demonstrated herein that the T-cell populations induced by either vaccine have both shared and unique Vα and Vβ TCR gene usage (FIG. 2) and that T-cell lines created from vaccinated CEA-Tg mice, specific for one of two CEA epitopes demonstrate differential avidity and antigen-specific cytolytic activity (FIG. 5). Taken together, these studies demonstrate that the two immunotherapeutic vaccines induce distinct T-cell populations, and the differences in the phenotype and function of these T-cell populations may be attributed to both the vector and the antigen. These findings are applicable to the use of any antigen in the context of the immunotherapy compositions.

The mode of antigen delivery by either vaccine platform may influence the generation of these distinct responses. The mechanism by which yeast-CEA predominantly activates the immune response is through the uptake of the CEA-expressing yeast and subsequent processing and presentation of the CEA antigen by dendritic cells (DCs) (Bernstein et al., *Vaccine* 2008 Jan. 24; 26(4):509-21), while the rV/F-CEA/TRICOM vectors infect cells, inducing intracellular expression that allows the CEA antigen to be processed and presented (Hodge et al., *Cancer Res* 1999 Nov. 15; 59(22):5800-7). Another difference observed is that rV/F-CEA/TRICOM vaccination induces the production of CEA-specific antibody while yeast-CEA does not (data not shown). Such mechanistic differences in the activation of the cellular and humoral arms of the immune system may also influence the vector- and antigen-specific induction of distinct T-cell populations.

Surprisingly, the inventors discovered that administering two vaccines targeting the same antigen induces distinct T-cell populations and results in significantly higher antitumor immunity in a murine orthotopic pulmonary metastasis model (FIG. 6). This study also showed for the first time that two vaccine platforms targeting the same antigen could be concurrently administered due to their induction of distinct T-cell populations. Furthermore, these data show that concurrent administration of the two vaccines results in substantially increased antitumor effects, due to the induction of a more diverse T-cell population targeting the same antigen. These findings indicate that concurrently combining these vaccines can be utilized to increase antigen-specific immunity. The concurrent use of immunotherapeutic vaccines as described herein induces a more diverse T-cell population consisting of T cells generated from both vaccines, making a diversified prime-boost schedule used prior to the invention unnecessary, although combining a diversified prime-boost schedule with the concurrent administration protocol described herein may further enhance an effective immune response. The present invention maximizes the immune response beginning with the initial vaccination by inducing a more diverse T-cell population that is then boosted and expanded in magnitude with each subsequent vaccination. Such a strategy would be efficacious in cancer patients as well as patients suffering from chronic infectious disease, because a more diverse T-cell population would be induced early in their treatment.

Accordingly, the present invention relates to the concurrent use of two or more different immunotherapy compositions to induce therapeutic immune responses against one or more antigens, and/or to prevent, ameliorate and/or treat a disease or condition, including cancer or an infectious disease. In one embodiment, the two or more different immunotherapy compositions target the same antigen(s). In another embodiment, one of the two or more different immunotherapy compositions targets one or more antigens, and the other of the immunotherapy compositions is provided as an adjuvant, without necessarily targeting an antigen, or without necessarily targeting the same antigen as the other composition (i.e., in one embodiment, the second composition targets a different antigen). In one embodiment, which may include any combinations of the embodiments above, the two or more immunotherapy compositions are administered concurrently, but to different physical sites in the patient. In another embodiment, which may include any combination of the embodiments above, the two or more different immunotherapy compositions are administered concurrently and to the same, or substantially adjacent, site in the patient.

The two or more different immunotherapy compositions used in the present invention are each capable, individually, of inducing an immune response, and preferably, at least a cellular immune response, and more preferably, a T cell-mediated cellular immune response. In one aspect, at least one of the compositions is capable of inducing a CD8+ and/or a CD4+ T cell-mediated immune response and more preferably, a CD8+ and a CD4+ T cell-mediated immune response. Preferably, all of the compositions used concurrently according to the invention are capable of inducing a CD8+ and/or a CD4+ T cell-mediated immune response, and more preferably, a CD8+ and a CD4+ immune response. Optionally, at least one of the compositions is capable of eliciting a humoral immune response. Preferably, the T cell-mediated immune response that is elicited by one of the immunotherapy compositions is phenotypically and/or functionally distinct in one or more aspects from the T cell-mediated immune response that is elicited by the other immunotherapy composition. In one aspect, the immunotherapeutic composition has one or more of the following characteristics: (a) stimulates one or more pattern recognition receptors effective to activate an antigen presenting cell; (b) upregulates adhesion molecules, co-stimulatory molecules, and MHC class I and/or class II molecules on antigen presenting cells; (c) induces production of proinflammatory cytokines by antigen presenting cells; (d) induces production of Th1-type cytokines by T cells; (e) induces production of Th17-type cytokines by T cells; (f) inhibits or downregulates Treg; and/or (g) elicits MHC Class I and/or MHC Class II, antigen-specific immune responses. Suitable immunotherapeutic compositions can include yeast-based immunotherapy compositions, viral-based immunotherapy compositions, antibody-based immunotherapy compositions, DNA immunotherapy compositions, subunit vaccines, and any components or adjuvants useful for stimulating or modulating an immune response, such as TLR agonists, cytokines, immune potentiators, and other agents, and any combinations thereof, many of which are described in more detail below. In one aspect, immunotherapy compositions to be used in the present invention include recombinant virus-based compositions and yeast-based compositions (described in detail below).

Virus-Based Immunotherapy Compositions

One aspect of the invention relates to a recombinant virus-based immunotherapy composition (which phrase may be used interchangeably with "virus-based immunotherapy product", "virus-based composition", "virus-based immunotherapeutic", "virus-based vaccine", "immunotherapy composition comprising or including a recombinant virus or recombinant viral vector", or any similar derivation of these phrases). As used herein, the phrase virus-based immunotherapy composition" refers to a composition that includes a viral vector component (e.g., a recombinant virus or portion thereof effective to constitute a viral vector) and that elicits an immune response sufficient to achieve at least one therapeutic benefit in a subject. Virus-based immunotherapy compositions and methods of making and generally using the same, are described in detail, for example, in U.S. Pat. Nos. 6,045,802, 6,893,869, 6,548,068, and 6,969,609, each of which is incorporated herein by reference in its entirety. In one aspect, a virus-based immunotherapy composition useful in the invention is capable of inducing a CD8+ and/or a CD4+ T cell-mediated immune response and in one aspect, a CD8+ and a CD4+ T cell-mediated immune response, and in one aspect, a humoral immune response. A virus-based immunotherapy composition useful in the present invention can, for example, elicit an immune response in an individual such that the individual is treated for the disease or condition, or such that symptoms resulting from the disease or condition are alleviated or treated.

A virus-based immunotherapy composition typically comprises a viral vector comprising a virus genome or portions thereof (e.g., a recombinant virus) and a nucleic acid sequence encoding at least one antigen(s) from a disease causing agent or disease state (e.g., a cancer antigen(s), infectious disease antigen(s), and/or at least one immunogenic domain thereof). In some embodiments, a virus-based immunotherapy composition further includes at least one viral vector comprising one or more nucleic acid sequences encoding one or more immunostimulatory molecule(s). In some embodiments, the genes encoding immunostimulatory molecules and antigens are inserted into the same viral vector (the same recombinant virus).

Viruses that may be used in such immunotherapy compositions of the present invention are any viruses that infect cells, inducing intracellular expression of the antigen carried by the virus that allows the antigen to be processed and presented. Preferred among these viruses are those that induce a Th1 response and CD8+ T-cells with a Tc1 phenotype. Viruses that may be used in a composition of the invention include viruses in which a portion of the genome can be deleted to introduce new genes without destroying infectivity of the virus.

Parental viruses (i.e., viruses from which viral vectors/recombinant viruses are produced, derived, based, etc.) useful in the production of viral vectors of the invention include, but are not limited to, poxvirus, Herpes virus, adenovirus, alphavirus, retrovirus, picornavirus, baculovirus, and iridovirus. Poxviruses (members of the family Poxyiridae) having utility in the present invention include replicating and non-replicating vectors. Such poxviruses include, but are not limited to, orthopox (genus *Orthopoxvirus*) such as vaccinia virus (Perkus et al., *Science* 229: 981-984, 1985; Kaufman et al., *Int. J. Cancer* 48:900-907, 1991, Moss, *Science* 252:1662, 1991), raccoon pox, rabbit pox and the like, avipox (genus *Avipoxvirus*) including fowlpox virus, suipox (genus *Suipoxvirus*), capripox (genus *Capripoxvirus*) and the like. Poxviruses may be selected from the group of vaccinia-Copenhagen, vaccinia-Wyeth strain, highly attenuated vaccinia virus (vaccinia-MVA strain), modified vaccinia Ankara (Sutter and Moss, *Proc. Nat'l Acad. Sci. U.S.A.* 89:10847-10851; Sutter et al., *Virology* 1994), NYVAC, TROVAC, canarypox, ALVAC (Baxby and Paoletti, *Vaccine* 10:8-9, 1992; Rinns, M. M. et al., (Eds) Recombinant Poxviruses CRC Press, Inc., Boca Raton 1992; Paoletti, E., *Proc. Nat'l Acad. Sci. USA* 93:11349-11353, 1996), swinepox, and the like. A derivative of the vaccinia-Wyeth strain includes but is not limited to vTBC33 which lacks a functional K1L gene. In yet another embodiment, the virus is Dry-Vax available as a smallpox vaccine from the Centers for Disease Control, Atlanta, Ga. In one embodiment, the recombinant vector is a vaccinia virus. In another embodiment, the recombinant vector is from fowlpox virus. One strain of fowlpox virus, for example, is PDXVAC-TC (Schering-Plough Corporation).

Recombinant poxviruses having utility in the present invention have a number of attributes, including (i) efficient delivery of genes to multiple cell types, including antigen presenting cells (APC) and tumor cells; (ii) high levels of protein expression; (iii) optimal presentation of antigens to the immune system; (iv) the ability to elicit cell-mediated immune responses as well as antibody responses; (v) transient, rather than permanent, genetic modification of cells, and (vi) the ability to use combinations of poxviruses from different genera, as they are not immunologically cross-reactive.

Recombinant vaccinia (rV, rMVA) and recombinant fowlpox (rF) viruses are two exemplary viruses for use in the virus-based immunotherapy compositions of the invention. Recombinant vaccinia and fowlpox viruses containing murine B7-1, ICAM-1, and LFA-3 genes as well as the human CEA gene (rV/F-CEA/TRICOM) have been described (Hodge et al., *Cancer Res* 1999 Nov. 15; 59(22): 5800-7; Grosenbach et al., *Cancer Res* 2001 Jun. 1; 61(11): 4497-505; and Hodge et al., *Cancer Res* 2003 Nov. 15; 63:7942-7949), each of which is incorporated herein by reference in its entirety. The murine GM-CSF-expressing rF virus (rF-GM-CSF) has been previously described (Kass et al., *Cancer Res* 2001 Jan. 1; 61(1):206-14). For purposes of the present invention, a vaccine designated "rV/F-CEA/TRICOM" refers to a complete vaccine protocol that includes a priming with rV-CEA/TRICOM (recombinant vaccinia containing polynucleotides encoding B7-1, ICAM-1, LFA-3 and CEA) admixed with rF-GM-CSF (recombinant fowl pox containing a gene encoding GM-CSF) which is boosted every 7 days with rF-CEA/TRICOM recombinant fowlpox containing polynucleotides encoding B7-1, ICAM- 1, LFA-3 and CEA) admixed with rF-GM-CSF. It is to be understood that CEA is just one example of a suitable antigen (in this case, a tumor-associated or cancer antigen) to be used in connection with one or more immunotherapy compositions of the invention.

The viral vector of the present invention comprises at least one expression control element operably linked to the nucleic acid sequence. The expression control elements are inserted in the vector to control and regulate the expression of the nucleic acid sequence (Ausubel et al, 1987, in "Current Protocols in Molecular Biology, John Wiley and Sons, New York, N.Y.). Expression control elements are known in the art and include promoters. Promoters useful in the present invention are poxyiral promoters as are known in the art which include, but are not limited to, 30K, 13, sE/L, 7.5K, 40K, and C1. The nucleic acid sequence of the 30K promoter is disclosed in GenBank Accession No. M35027 at base numbers 28,012 through 28,423 (antisense). The nucleic acid sequence of 13 is disclosed in GenBank Accession No. J03399 at base numbers 1100 through 1301 (antisense). The nucleic acid sequence of the 7.5K promoter is disclosed in GenBank Accession No. M35027 at base numbers 186550 through 186680. The nucleic acid sequence of the 40K promoter is disclosed in GenBank Accession No. M13209 at base numbers 9700 through 9858 (antisense). The nucleic acid sequence of the C1 promoter is disclosed in GenBank Accession No. M59027 at base numbers 1 through 242 and in U.S. Pat. No. 5,093,258. The sequence of the sE/L promoter is known in the art. Other poxvirus promoters may be used, such as, those described by Davison and Moss (*J. Mol. Biol.* 210:749-769. (1989). Any of these promoters can be synthesized by using standard methods in the art. The selection of an appropriate promoter is based on its timing and level of expression. Early or early/late promoters are used in one aspect. In one embodiment, the promoter or combination of promoters utilized allow for optimal expression of each antigen and/or costimulatory molecule in an infected host to provide a synergistic immune response. In one embodiment, each nucleic acid molecule encoding an antigen or costimulatory molecule is controlled by a separate and distinct promoter.

As used herein with any immunotherapy composition described for use in the present invention, immunostimulatory molecules include, but are not limited to, cytokines and costimulatory molecules. For example, cytokines can include, but are not limited to, tumor necrosis factor-α (TNF-α), interleukin-6 (IL-6), granulocyte-macrophage-colony stimulating factor (GM-CSF), interferon-γ (IFN-γ), IFN-α, IFN-λ, interleukin-12 (IL-12), RANTES, and interleukin-2 (IL-2). Costimulatory molecules include, but are not limited to, B7.1 (also referred to herein as B7-1), B7.2 (also referred to herein as B7-2), ICAM-1, LFA-3, 4-1BBL, CD59, CD40, CD40L and CD70. Immunostimulatory molecules can be provided in an immunotherapy composition of the invention alone and/or in a variety of combinations, and can be expressed by one or more viral vectors or other vaccine vectors. In one aspect, the recombinant vector of the present invention comprises genes encoding at least three costimulatory molecules for synergistic enhancement of immune responses which is not obtainable by the use of a single or a double costimulatory molecule. Genes encoding various combinations of costimulatory molecules are an element of the invention for use in the recombinant vector and may include such combinations as: B7.1, B7.2, ICAM-1, and LFA-3; B7.1, ICAM-1, and LFA-3; B7.1, B7.2, ICAM-1, and 4-1BBL; B7.1, B7.2, ICAM-1, LFA-3, and 4-1BBL; CD59 and VCAM-1; and B7.1 and B7.2; CD59, CD40, 4-BBL, CD70 and VCAM-1, B7.1, B7.2; OX-40L, 4-1BBL; depending on the desired immune response and the disease or condition to be treated.

B7.1 (CD80) is a natural ligand for the T-cell antigen, CD28, mediating T- and B-cell adhesion. B7.1 is expressed on activated B-cells and gamma-interferon-stimulated monocytes. The binding of CD80 to CD28 and CTLA-4 provides a co-stimulatory signal to T-cells and leads to upregulated lymphokine production. B7.2 (CD86) is an alternative ligand for CD28 and CTLA-4.

ICAM-1 (Inter-Cellular Adhesion Molecule 1), also known as CD54, is a leukocyte- and endothelial-associated intercellular adhesion molecule and is a ligand for LFA-1 (integrin), a leukocyte receptor. ICAM-1 is upregulated upon cytokine stimulation and is involved in cellular interactions, leukocyte endothelial transmigration, and signaling related to recruitment of proinflammatory immune cells.

LFA-3 (lymphocyte function associated antigen-3), or CD58, is an adhesion molecule expressed by antigen presenting cells (APCs), mediating a costimulatory signal through CD2, an adhesion molecule found on T cells and natural killer (NK) cells. This interaction promotes intercellular adhesion and the activation of T cells.

4-1BBL is expressed on activated antigen presenting cells (APCs) and is the ligand for 4-1BB, a costimulatory member of the tumor necrosis factor receptor family expressed on activated CD4 and CD8 T cells. The interaction of these molecules can enhance T cell proliferation and survival, and expand and activate CD8+ T cell memory (Bukczynski et al., *Proc. Natl. Acad. Sci. U.S.A.* 2004, 101(5):1291-6).

CD59 is a complement regulatory protein. Viruses, including vaccinia virus, vaccinia incorporate host cell CD59 into their own viral envelope to prevent lysis by complement (Bohana-Kashtan et al., 2004, *Mol. Immunol.* 41 (6-7): 583-97).

VCAM-1 (vascular cell adhesion molecule-1), or CD106, is an adhesion molecule expressed by endothelial cells and mediates the adhesion of lymphocytes, monocytes, eosinophils, and basophils to vascular endothelium. It also functions in leukocyte-endothelial cell signal transduction.

CD40 is a costimulatory protein expressed by antigen presenting cells (APCs). Binding of CD40 to its natural ligand, CD40L, on T cells, activates the APC and initiates a signaling cascade that mediates a variety of immune and inflammatory responses.

CD70 is a ligand for CD27, which is a receptor required for the generation and maintenance of long-term T cell immunity.

OX40-L is expressed on expressed on the surface of activated B cells, T cells, dendritic cells and endothelial cells and binds to its natural receptor, OX40, which is primarily expressed by activated CD4+ T cells, and therefore, this interaction is related to T cell activation.

GM-CSF (granulocyte macrophage colony stimulating factor) is a cytokine that functions as a white blood cell growth factor produced by T cells, macrophages, and other cells. GM-CSF stimulates stem cells to produce granulocytes (neutrophils, eosinophils, and basophils) and monocytes, and is thus part of the immune system activation and development process.

Simultaneous production of an immunostimulatory molecule and the antigen(s) at the site of virus replication/infection (in any case, the site of antigen production) enhances the generation of specific effectors. Dependent upon the specific immunostimulatory molecules, different mechanisms might be responsible for the enhanced immunogenicity: augmentation of help signal (IL-2), recruitment of professional APC (GM-CSF), increase in CTL frequency (IL-2), and/or effect on antigen processing pathway and MHC expression (IFN-γ and TNFα). In some cases, it may be beneficial to produce a recombinant virus comprising more than one antigen of interest for the purpose of having a multivalent vaccine.

In one embodiment, a pharmaceutical composition comprises a recombinant virus (e.g., a poxvirus) containing nucleic acid molecules encoding multiple costimulatory molecules in a pharmaceutically acceptable carrier. The recombinant virus may further comprise a nucleic acid sequence encoding at least one antigen or immunogenic domain thereof or alternatively, a second recombinant virus (e.g., a poxvirus) may be provided encoding at least one antigen or immunogenic domain thereof.

In one embodiment, a virus-based immunotherapy composition useful in the present invention includes a pharmaceutical composition comprising a recombinant virus (e.g., a recombinant poxvirus) comprising a nucleic acid sequence encoding B7.1 or B7.2, a nucleic acid sequence encoding ICAM-1, and a nucleic acid sequence encoding LFA-3 and a pharmaceutically acceptable carrier. In addition to the B7, ICAM-1, LFA-3 construct, the recombinant virus of the pharmaceutical composition may additionally comprise a nucleic acid sequence encoding at least one antigen or immunogenic domain thereof, or alternatively, the nucleic acid sequence encoding at least one antigen or immunogenic domain thereof may be provided in the composition by a second recombinant virus.

In one embodiment, the composition may also comprise exogenously added immunostimulatory molecules as are known in the art including, but not limited to, the costimulatory molecules B7, ICAM-1, LFA-3, 4-1BBL, CD59, CD40, CD70, VCAM-1, OX-40L and/or antibodies that bind to such immunostimulatory molecules, and/or agonists or antagonists of such immunostimulatory molecules, and/or cytokines and chemokines including but not limited to IL-2, GM-CSF, TNF-α, IFN-γ, IFN-α, IFN-λ, IL-12, RANTES, MIP-1α, Flt-3L (U.S. Pat. Nos. 5,554,512; 5,843,423) and the like, for additional synergy or enhancement of an immune response. The cytokines and chemokines themselves may be provided in the composition or, alternatively, the cytokines and chemokines may be provided by a recombinant viral vector encoding the cytokine or chemokine.

In one embodiment of the present invention, a recombinant poxvirus is provided comprising a nucleic acid sequence encoding LFA-3 or functional portion thereof under control of a 30K poxyiral promoter, a nucleic acid sequence encoding ICAM-1 or portion thereof under control of an I3 poxyiral promoter, and a nucleic acid sequence encoding B7.1 or portion thereof under control of an sE/L poxyiral promoter. The recombinant poxvirus may further provide a nucleic acid sequence encoding at least one antigen or immunogenic domain thereof.

In another embodiment of the present invention, a recombinant poxvirus is provided comprising a nucleic acid sequence encoding B7.1 under control of a sE/L poxyiral promoter, a nucleic acid sequence encoding LFA-3 or portion thereof under control of the 13 poxyiral promoter, and a nucleic acid sequence encoding ICAM-1 or portion thereof under control of the 7.5K poxvirus promoter. Optionally the construct further comprises a nucleic acid sequence encoding at least antigen or immunogenic domain thereof.

In an embodiment of the invention, a recombinant fowlpox virus comprises a nucleic acid sequence encoding B7.1 or portion thereof under control of the sE/L poxyiral promoter, a nucleic acid sequence encoding LFA-3 or portion thereof under control of the I3 poxyiral promoter, and a nucleic acid sequence encoding ICAM-1 or portion thereof under control of the 7.5K poxyiral promoter. A recombinant fowlpox virus may further comprise a nucleic acid sequence encoding a target antigen under control of a poxyiral promoter such as the 40K poxyiral promoter.

In some embodiments of the invention, the recombinant virus-based immunotherapy compositions do not express an antigen, although in such a case, the recombinant viral vector(s) of such compositions preferably still express one or more immunostimulatory molecules as described elsewhere herein. In this embodiment of the invention, the antigen is provided by one or more different immunotherapy compositions as described herein, such as the yeast-based immunotherapy composition of the invention. Because each of the immunotherapy compositions used in the invention may provide some unique "danger signals" or costimulatory signals to the immune system, it may be sufficient to provide the contributions of the vectors while only one of the compositions comprises an antigen.

The present invention further provides methods of generating recombinant viruses comprising nucleic acid sequences encoding antigens and/or multiple costimulatory molecules. One method of generation of recombinant poxviruses is accomplished via homologous recombination in vivo between parental poxvirus genomic DNA and a plasmid vector that carries the heterologous sequences to be inserted, as disclosed in U.S. Pat. No. 5,093,258. Plasmid vectors for the insertion of foreign sequences into poxviruses are constructed by standard methods of recombinant DNA technology. The plasmid vectors contain one or more chimeric foreign genes, each comprising a poxvirus promoter linked to a protein coding sequence, flanked by viral sequences from a non-essential region of the poxvirus genome. The plasmid is transfected into cells infected with the parental poxvirus using art accepted transfection methods, and recombination between poxvirus sequences on the plasmid and the corresponding DNA in the parental viral genome results in the insertion into the viral genome of the chimeric foreign genes from the plasmid. Recombinant viruses are selected and purified using any of a variety of selection or screening systems as are known in the art. Insertion of the foreign genes into the vaccinia genome is confirmed by polymerase chain reaction (PCR) analysis. Expression of the foreign genes is demonstrated by Western blot analysis. An alternative method of generation of recombinant poxviruses is accomplished by direct ligation (Pleiderer et al., *J. Gen. Virol.* 76:2957-2962, 1995; Merchlinsky et al., *Virol.* 238:444-451, 1997).

Yeast-Based Immunotherapy Compositions

In one embodiment of the invention, the invention includes the use of at least one "yeast-based immunotherapeutic composition" (which phrase may be used interchangeably with "yeast-based immunotherapy product", "yeast-based composition", "yeast-based immunotherapeutic", "yeast-based vaccine", "immunotherapy composition comprising a yeast vehicle", or any similar derivation of these phrases). As used herein, the phrase "yeast-based immunotherapy composition" refers to a composition that includes a yeast vehicle component and that elicits an immune response sufficient to achieve at least one therapeutic benefit in a subject. More particularly, a yeast-based immunotherapeutic composition is a composition that includes a yeast vehicle component and can elicit or induce an immune response, such as a cellular immune response, including without limitation a T cell-mediated cellular immune response. In one aspect, a yeast-based immunotherapy composition useful in the invention is capable of inducing a CD8+ and/or a CD4+ T cell-mediated immune response and in one aspect, a CD8+ and a CD4+ T cell-mediated immune response. Optionally, a yeast-based immunotherapy composition is capable of eliciting a humoral immune response. A yeast-based immunotherapy composition useful in the present invention can, for example, elicit an immune response in an individual such that the individual is treated for the disease or condition, or such that symptoms resulting from the disease or condition are alleviated or treated.

Typically, a yeast-based immunotherapy composition includes a yeast vehicle and at least one antigen or immunogenic domain thereof expressed by, attached to, or mixed with the yeast vehicle. In some embodiments, the antigen or immunogenic domain thereof is provided as a fusion protein. In one aspect of the invention, fusion protein can include two or more antigens. In one aspect, the fusion protein can include two or more immunogenic domains of one or more antigens, or two or more epitopes of one or more antigens. A TARMOGEN® is one non-limiting example of a yeast-based immunotherapy composition that is useful in the present invention. A TARMOGEN® (TARgeted MOlecular immunoGEN, GlobeImmune, Inc., Louisville, Colo.) generally refers to a yeast vehicle expressing one or more heterologous antigens extracellularly (on its surface), intracellularly (internally or cytosolically) or both extracellularly and intracellularly.

Yeast-based immunotherapy compositions, and methods of making and generally using the same, are described in detail, for example, in U.S. Pat. Nos. 5,830,463, 7,083,787, 7,465,454, U.S. Patent Publication 2007-0224208, U.S. Patent Publication No. US 2008-0003239, and in Stubbs et al., *Nat. Med.* 7:625-629 (2001), Lu et al., *Cancer Research* 64:5084-5088 (2004), and in Bernstein et al., *Vaccine* 2008 Jan. 24; 26(4):509-21, each of which is incorporated herein by reference in its entirety. These yeast-based immunotherapeutic products have been shown to elicit immune responses, including cellular and humoral immune responses. Yeast-based immunotherapeutic products are capable of killing target cells expressing a variety of antigens in vivo, in a variety of animal species, and do so via antigen-specific, CD8+ and/or CD4+ mediated immune responses. Additional studies have shown that yeast are avidly phagocytosed by and directly activate dendritic cells which then present yeast-associated proteins to CD4+ and CD8+ T cells in a highly efficient manner. See, e.g., Stubbs et al. *Nature Med.* 5:625-629 (2001) and U.S. Pat. No. 7,083,787.

In any of the yeast-based immunotherapy compositions used in the present invention, the following aspects related to the yeast vehicle are included in the invention. According to the present invention, a yeast vehicle is any yeast cell (e.g., a whole or intact cell) or a derivative thereof (see below) that can be used in conjunction with one or more antigens, immunogenic domains thereof or epitopes thereof in a therapeutic composition of the invention, or in one aspect, the yeast vehicle can be used alone or as an adjuvant. The yeast vehicle can therefore include, but is not limited to, a live intact yeast microorganism (i.e., a yeast cell having all its components including a cell wall), a killed (dead) or inactivated intact yeast microorganism, or derivatives thereof including: a yeast spheroplast (i.e., a yeast cell lacking a cell wall), a yeast cytoplast (i.e., a yeast cell lacking a cell wall and nucleus), a yeast ghost (i.e., a yeast cell lacking a cell wall, nucleus and cytoplasm), a subcellular yeast membrane extract or fraction thereof (also referred to as a yeast membrane particle and previously as a subcellular yeast particle), any other yeast particle, or a yeast cell wall preparation.

Yeast spheroplasts are typically produced by enzymatic digestion of the yeast cell wall. Such a method is described, for example, in Franzusoff et al., 1991, *Meth. Enzymol.* 194, 662-674., incorporated herein by reference in its entirety.

Yeast cytoplasts are typically produced by enucleation of yeast cells. Such a method is described, for example, in Coon, 1978, *Natl. Cancer Inst. Monogr.* 48, 45-55 incorporated herein by reference in its entirety.

Yeast ghosts are typically produced by resealing a permeabilized or lysed cell and can, but need not, contain at least some of the organelles of that cell. Such a method is described, for example, in Franzusoff et al., 1983, *J. Biol. Chem.* 258, 3608-3614 and Bussey et al., 1979, *Biochim. Biophys. Acta* 553, 185-196, each of which is incorporated herein by reference in its entirety.

A yeast membrane particle (subcellular yeast membrane extract or fraction thereof) refers to a yeast membrane that lacks a natural nucleus or cytoplasm. The particle can be of any size, including sizes ranging from the size of a natural yeast membrane to microparticles produced by sonication or other membrane disruption methods known to those skilled in the art, followed by resealing. A method for producing subcellular yeast membrane extracts is described, for example, in Franzusoff et al., 1991, *Meth. Enzymol.* 194, 662-674. One may also use fractions of yeast membrane particles that contain yeast membrane portions and, when the antigen or other protein was expressed recombinantly by the yeast prior to preparation of the yeast membrane particles, the antigen or other protein of interest. Antigens or other proteins of interest can be carried inside the membrane, on either surface of the membrane, or combinations thereof (i.e., the protein can be both inside and outside the membrane and/or spanning the membrane of the yeast membrane particle). In one embodiment, a yeast membrane particle is a recombinant yeast membrane particle that can be an intact, disrupted, or disrupted and resealed yeast membrane that includes at least one desired antigen or other protein of interest on the surface of the membrane or at least partially embedded within the membrane.

An example of a yeast cell wall preparation is isolated yeast cell walls carrying an antigen on its surface or at least partially embedded within the cell wall such that the yeast cell wall preparation, when administered to an animal, stimulates a desired immune response against a disease target.

Any yeast strain can be used to produce a yeast vehicle of the present invention. Yeast are unicellular microorganisms that belong to one of three classes: Ascomycetes, Basidiomycetes and Fungi Imperfecti. One consideration for the selection of a type of yeast for use as an immune modulator is the pathogenicity of the yeast. In one embodiment, the yeast is a non-pathogenic strain such as *Saccharomyces cerevisiae*. The selection of a non-pathogenic yeast strain minimizes any adverse effects to the individual to whom the yeast vehicle is administered. However, pathogenic yeast may be used if the pathogenicity of the yeast can be negated by any means known to one of skill in the art (e.g., mutant strains). In accordance with one aspect of the present invention, nonpathogenic yeast strains are used.

Genera of yeast strains that may be used in the invention include but are not limited to *Saccharomyces, Candida* (which can be pathogenic), *Cryptococcus, Hansenula, Kluyveromyces, Pichia, Rhodotorula, Schizosaccharomyces* and *Yarrowia*. In one aspect, yeast genera are selected from

*Saccharomyces, Candida, Hansenula, Pichia* or *Schizosaccharomyces*, and in one aspect, *Saccharomyces* is used. Species of yeast strains that may be used in the invention include but are not limited to *Saccharomyces cerevisiae, Saccharomyces carlsbergensis, Candida albicans, Candida kefyr, Candida tropicalis, Cryptococcus laurentii, Cryptococcus neoformans, Hansenula anomala, Hansenula polymorpha, Kluyveromyces fragilis, Kluyveromyces lactis, Kluyveromyces marxianus* var. *lactis, Pichia pastoris, Rhodotorula rubra, Schizosaccharomyces pombe*, and *Yarrowia lipolytica*. It is to be appreciated that a number of these species include a variety of subspecies, types, subtypes, etc. that are intended to be included within the aforementioned species. In one aspect, yeast species used in the invention include *S. cerevisiae, C. albicans, H. polymorpha, P. pastoris* and *S. pombe. S. cerevisiae* is useful due to it being relatively easy to manipulate and being "Generally Recognized As Safe" or "GRAS" for use as food additives (GRAS, FDA proposed Rule 62FR18938, Apr. 17, 1997). One embodiment of the present invention is a yeast strain that is capable of replicating plasmids to a particularly high copy number, such as a *S. cerevisiae* cir$^o$ strain. The *S. cerevisiae* strain is one such strain that is capable of supporting expression vectors that allow one or more target antigen(s) and/or antigen fusion protein(s) and/or other proteins to be expressed at high levels. In addition, any mutant yeast strains can be used in the present invention, including those that exhibit reduced post-translational modifications of expressed target antigens or other proteins, such as mutations in the enzymes that extend N-linked glycosylation.

In one embodiment, a yeast vehicle of the present invention is capable of fusing with the cell type to which the yeast vehicle and antigen/agent is being delivered, such as a dendritic cell or macrophage, thereby effecting particularly efficient delivery of the yeast vehicle, and in many embodiments, the antigen(s) or other agent, to the cell type. As used herein, fusion of a yeast vehicle with a targeted cell type refers to the ability of the yeast cell membrane, or particle thereof, to fuse with the membrane of the targeted cell type (e.g., dendritic cell or macrophage), leading to syncytia formation. As used herein, a syncytium is a multinucleate mass of protoplasm produced by the merging of cells. A number of viral surface proteins (including those of immunodeficiency viruses such as HIV, influenza virus, poliovirus and adenovirus) and other fusogens (such as those involved in fusions between eggs and sperm) have been shown to be able to effect fusion between two membranes (i.e., between viral and mammalian cell membranes or between mammalian cell membranes). For example, a yeast vehicle that produces an HIV gp120/gp41 heterologous antigen on its surface is capable of fusing with a CD4+ T-lymphocyte. It is noted, however, that incorporation of a targeting moiety into the yeast vehicle, while it may be desirable under some circumstances, is not necessary. In the case of yeast vehicles that express antigens extracellularly, this can be a further advantage of the yeast vehicles of the present invention. In general, yeast vehicles useful in the present invention are readily taken up by dendritic cells (as well as other cells, such as macrophages).

In some embodiments of the invention, the yeast-based immunotherapy composition includes at least one antigen, immunogenic domain thereof, or epitope thereof. The antigens contemplated for use in this invention include any antigen against which it is desired to elicit an immune response (described in more detail below).

In some embodiments of the invention, the yeast-based immunotherapy compositions do not express or otherwise contain or display an antigen, although in this case, the yeast vehicle may optionally express one or more immunostimulatory molecules. In this embodiment of the invention, the antigen is provided by one or more different immunotherapy compositions as described herein, such as a virus-based immunotherapy composition. Because each of the immunotherapy compositions used in the invention may provide some unique "danger signals" or costimulatory signals to the immune system, it may be sufficient to provide the contributions of the vectors while only one of the compositions comprises an antigen.

According to the present invention, the term "yeast vehicle-antigen complex" or "yeast-antigen complex" is used generally to describe any association of a yeast vehicle with an antigen, and can be used interchangeably with "yeast-based immunotherapy composition" when such composition is used to elicit an immune response as described above. Such association includes expression of the antigen by the yeast (a recombinant yeast), introduction of an antigen into a yeast, physical attachment of the antigen to the yeast, and mixing of the yeast and antigen together, such as in a buffer or other solution or formulation. These types of complexes are described in detail below.

In one embodiment, a yeast cell (e.g., a whole yeast) used to prepare the yeast vehicle or that is the yeast vehicle is transfected with a heterologous nucleic acid molecule encoding a protein (e.g., the antigen or agent) such that the protein is expressed by the yeast cell. Such a yeast is also referred to herein as a recombinant yeast or a recombinant yeast vehicle. The yeast cell can then be administered, or the yeast cell can be killed, or it can be derivatized such as by formation of yeast spheroplasts, cytoplasts, ghosts, or subcellular particles. Yeast spheroplasts can also be directly transfected with a recombinant nucleic acid molecule (e.g., the spheroplast is produced from a whole yeast, and then transfected) in order to produce a recombinant spheroplast that expresses an antigen or other protein.

In one aspect, a yeast cell or yeast spheroplast used to prepare the yeast vehicle is transfected with a recombinant nucleic acid molecule encoding the antigen(s) or other protein such that the antigen or other protein is recombinantly expressed by the yeast cell or yeast spheroplast. In this aspect, the yeast cell or yeast spheroplast that recombinantly expresses the antigen(s) or other protein is used to produce a yeast vehicle comprising a yeast cytoplast, a yeast ghost, or a yeast membrane particle or yeast cell wall particle, or fraction thereof.

A number of antigens and/or other proteins to be produced by a yeast vehicle of the present invention is any number of antigens and/or other proteins that can be reasonably produced by a yeast vehicle, and typically ranges from at least one to at least about 6 or more, including from about 2 to about 6 heterologous antigens and or other proteins.

Expression of an antigen or other protein in a yeast vehicle of the present invention can be accomplished using techniques known to those skilled in the art. Briefly, in one aspect, a nucleic acid molecule encoding at least one desired antigen or other protein is inserted into an expression vector in such a manner that the nucleic acid molecule is operatively linked to a transcription control sequence in order to be capable of effecting either constitutive or regulated expression of the nucleic acid molecule when transformed into a host yeast cell. Nucleic acid molecules encoding one or more antigens and/or other proteins can be on one or more expression vectors operatively linked to one or more expression control sequences. Particularly important expression control sequences are those which control transcription initiation, such as promoter and upstream activation sequences. Any suitable yeast promoter can be used in the present invention and a variety of such promoters are known to those skilled in the art. Promoters for expression in *Saccharomyces cerevisiae* include, but are not limited to, promoters of genes encoding the following yeast proteins: alcohol dehydrogenase I (ADH1) or II (ADH2), CUP1, phosphoglycerate kinase (PGK), triose phosphate isomerase (TPI), translational elongation factor EF-1 alpha (TEF2), glyceraldehyde-3-phosphate dehydrogenase (GAPDH; also referred to as TDH3, for triose phosphate dehydrogenase), galactokinase (GAL1), galactose-1-phosphate uridyl-transferase (GAL7), UDP-galactose epimerase (GAL10), cytochrome c1 (CYC1), Sec7 protein (SEC7) and acid phosphatase (PHO5), including hybrid promoters such as ADH2/GAPDH and CYC1/GAL10 promoters, and including the ADH2/GAPDH promoter, which is induced when glucose concentrations in the cell are low (e.g., about 0.1 to about 0.2 percent), as well as the CUP1 promoter and the TEF2 promoter. Likewise, a number of upstream activation sequences (UASs), also referred to as enhancers, are known. Upstream activation sequences for expression in *Saccharomyces cerevisiae* include, but are not limited to, the UASs of genes encoding the following proteins: PCK1, TPI, TDH3, CYC1, ADH1, ADH2, SUC2, GAL1, GAL7 and GAL10, as well as other UASs activated by the GAL4 gene product, with the ADH2 UAS being used in one aspect. Since the ADH2 UAS is activated by the ADR1 gene product, it may be preferable to overexpress the ADR1 gene when a heterologous gene is operatively linked to the ADH2 UAS. Transcription termination sequences for expression in *Saccharomyces cerevisiae* include the termination sequences of the α-factor, GAPDH, and CYC1 genes.

Transcription control sequences to express genes in methyltrophic yeast include the transcription control regions of the genes encoding alcohol oxidase and formate dehydrogenase.

Transfection of a nucleic acid molecule into a yeast cell according to the present invention can be accomplished by any method by which a nucleic acid molecule administered into the cell and includes, but is not limited to, diffusion, active transport, bath sonication, electroporation, microinjection, lipofection, adsorption, and protoplast fusion. Transfected nucleic acid molecules can be integrated into a yeast chromosome or maintained on extrachromosomal vectors using techniques known to those skilled in the art. Examples of yeast vehicles carrying such nucleic acid molecules are disclosed in detail herein. As discussed above, yeast cytoplast, yeast ghost, and yeast membrane particles or cell wall preparations can also be produced recombinantly by transfecting intact yeast microorganisms or yeast spheroplasts with desired nucleic acid molecules, producing the antigen therein, and then further manipulating the microorganisms or spheroplasts using techniques known to those skilled in the art to produce cytoplast, ghost or subcellular yeast membrane extract or fractions thereof containing desired antigens or other proteins.

In one aspect of the invention, the yeast vehicle is manipulated such that the antigen is expressed or provided by delivery or translocation of an expressed protein product, partially or wholly, on the surface of the yeast vehicle (extracellular expression). One method for accomplishing this aspect of the invention is to use a spacer arm for positioning one or more protein(s) on the surface of the yeast vehicle. For example, one can use a spacer arm to create a fusion protein of the antigen(s) or other protein of interest with a protein that targets the antigen(s) or other protein of interest to the yeast cell wall. For example, one such protein that can be used to target other proteins is a yeast protein (e.g., cell wall protein 2 (cwp2), Aga2, Pir4 or Flo1 protein) that enables the antigen(s) or other protein to be targeted to the yeast cell wall such that the antigen or other protein is located on the surface of the yeast. Proteins other than yeast proteins may be used for the spacer arm; however, for any spacer arm protein, it is most desirable to have the immunogenic response be directed against the target antigen rather than the spacer arm protein. As such, if other proteins are used for the spacer arm, then the spacer arm protein that is used should not generate such a large immune response to the spacer arm protein itself such that the immune response to the target antigen(s) is overwhelmed. One of skill in the art should aim for a small immune response to the spacer arm protein relative to the immune response for the target antigen(s). Spacer arms can be constructed to have cleavage sites (e.g., protease cleavage sites) that allow the antigen to be readily removed or processed away from the yeast, if desired. Any known method of determining the magnitude of immune responses can be used (e.g., antibody production, lytic assays, etc.) and are readily known to one of skill in the art.

Another method for positioning the target antigen(s) or other proteins to be exposed on the yeast surface is to use signal sequences such as glycosylphosphatidyl inositol (GPI) to anchor the target to the yeast cell wall. Alternatively, positioning can be accomplished by appending signal sequences that target the antigen(s) or other proteins of interest into the secretory pathway via translocation into the endoplasmic reticulum (ER) such that the antigen binds to a protein which is bound to the cell wall (e.g., cwp).

In one aspect, the spacer arm protein is a yeast protein. The yeast protein can consist of between about two and about 800 amino acids of a yeast protein. In one embodiment, the yeast protein is about 10 to 700 amino acids. In another embodiment, the yeast protein is about 40 to 600 amino acids. Other embodiments of the invention include the yeast protein being at least 250 amino acids, at least 300 amino acids, at least 350 amino acids, at least 400 amino acids, at least 450 amino acids, at least 500 amino acids, at least 550 amino acids, at least 600 amino acids, or at least 650 amino acids. In one embodiment, the yeast protein is at least 450 amino acids in length.

Use of yeast proteins can stabilize the expression of fusion proteins in the yeast vehicle, prevents posttranslational modification of the expressed fusion protein, and/or targets the fusion protein to a particular compartment in the yeast (e.g., to be expressed on the yeast cell surface). For delivery into the yeast secretory pathway, exemplary yeast proteins to use include, but are not limited to: Aga (including, but not limited to, Aga1 and/or Aga2); SUC2 (yeast invertase); alpha factor signal leader sequence; CPY; Cwp2p for its localization and retention in the cell wall; BUD genes for localization at the yeast cell bud during the initial phase of daughter cell formation; Flo1p; Pir2p; and Pir4p.

Other sequences can be used to target, retain and/or stabilize the protein to other parts of the yeast vehicle, for example, in the cytosol or the mitochondria. Examples of suitable yeast protein that can be used for any of the embodiments above include, but are not limited to, SEC7; phosphoenolpyruvate carboxykinase PCK1, phosphoglycerokinase PGK and triose phosphate isomerase TPI gene products for their repressible expression in glucose and cytosolic localization; the heat shock proteins SSA1, SSA3, SSA4, SSC1, whose expression is induced and whose proteins are more thermostable upon exposure of cells to heat treatment; the mitochondrial protein CYC1 for import into mitochondria; ACT1.

In one embodiment, control of the amount of yeast glycosylation is used to control the expression of antigens by the yeast, particularly on the surface. The amount of yeast glycosylation can affect the immunogenicity and antigenicity of the antigen expressed on the surface, since sugar moieties tend to be bulky. As such, the existence of sugar moieties on the surface of yeast and its impact on the three-dimensional space around the target antigen(s) should be considered in the modulation of yeast according to the invention. Any method can be used to reduce the amount of glycosylation of the yeast (or increase it, if desired). For example, one could use a yeast mutant strain that has been selected to have low glycosylation (e.g. mnn1, och1 and mnn9 mutants), or one could eliminate by mutation the glycosylation acceptor sequences on the target antigen. Alternatively, one could use a yeast with abbreviated glycosylation patterns, e.g. *Pichia*. One can also treat the yeast using methods that reduce or alter the glycosylation.

In one embodiment of the present invention, as an alternative to expression of an antigen or other protein recombinantly in the yeast vehicle, a yeast vehicle is loaded intracellularly with the protein or peptide, or with carbohydrates or other molecules that serve as an antigen and/or are useful as immunomodulatory agents or biological response modifiers according to the invention. Subsequently, the yeast vehicle, which now contains the antigen and/or other proteins intracellularly, can be administered to the patient or loaded into a carrier such as a dendritic cell. Peptides and proteins can be inserted directly into yeast vehicles of the present invention by techniques known to those skilled in the art, such as by diffusion, active transport, liposome fusion, electroporation, phagocytosis, freeze-thaw cycles and bath sonication. Yeast vehicles that can be directly loaded with peptides, proteins, carbohydrates, or other molecules include intact yeast, as well as spheroplasts, ghosts or cytoplasts, which can be loaded with antigens and other agents after production. Alternatively, intact yeast can be loaded with the antigen and/or agent, and then spheroplasts, ghosts, cytoplasts, or subcellular particles can be prepared therefrom. Any number of antigens and/or other agents can be loaded into a yeast vehicle in this embodiment, from at least 1, 2, 3, 4 or any whole integer up to hundreds or thousands of antigens and/or other agents, such as would be provided by the loading of a microorganism or portions thereof, for example.

In another embodiment of the present invention, an antigen and/or other agent is physically attached to the yeast vehicle. Physical attachment of the antigen and/or other agent to the yeast vehicle can be accomplished by any method suitable in the art, including covalent and non-covalent association methods which include, but are not limited to, chemically crosslinking the antigen and/or other agent to the outer surface of the yeast vehicle or biologically linking the antigen and/or other agent to the outer surface of the yeast vehicle, such as by using an antibody or other binding partner. Chemical cross-linking can be achieved, for example, by methods including glutaraldehyde linkage, photoaffinity labeling, treatment with carbodiimides, treatment with chemicals capable of linking di-sulfide bonds, and treatment with other cross-linking chemicals standard in the art. Alternatively, a chemical can be contacted with the yeast vehicle that alters the charge of the lipid bilayer of yeast membrane or the composition of the cell wall so that the outer surface of the yeast is more likely to fuse or bind to antigens and/or other agent having particular charge characteristics. Targeting agents such as antibodies, binding peptides, soluble receptors, and other ligands may also be incorporated into an antigen as a fusion protein or otherwise associated with an antigen for binding of the antigen to the yeast vehicle.

In yet another embodiment, the yeast vehicle and the antigen or other protein are associated with each other by a more passive, non-specific or non-covalent binding mechanism, such as by gently mixing the yeast vehicle and the antigen or other protein together in a buffer or other suitable formulation (e.g., admixture).

In one embodiment of the invention, the yeast vehicle and the antigen or other protein are both loaded intracellularly into a carrier such as a dendritic cell or macrophage to form the therapeutic composition or vaccine of the present invention.

In one embodiment, intact yeast (with or without expression of heterologous antigens or other proteins) can be ground up or processed in a manner to produce yeast cell wall preparations, yeast membrane particles or yeast fragments (i.e., not intact) and the yeast fragments can, in some embodiments, be provided with or administered with other compositions that include antigens (e.g., DNA vaccines, protein subunit vaccines, killed or inactivated pathogens) to enhance immune response. For example, enzymatic treatment, chemical treatment or physical force (e.g., mechanical shearing or sonication) can be used to break up the yeast into parts that are used as an adjuvant.

In one embodiment of the invention, yeast vehicles useful in the invention include yeast vehicles that have been killed or inactivated. Killing or inactivating of yeast can be accomplished by any of a variety of suitable methods known in the art. For example, heat inactivation of yeast is a standard way of inactivating yeast, and one of skill in the art can monitor the structural changes of the target antigen, if desired, by standard methods known in the art. Alternatively, other methods of inactivating the yeast can be used, such as chemical, electrical, radioactive or UV methods. See, for example, the methodology disclosed in standard yeast culturing textbooks such as Methods of Enzymology, Vol. 194, Cold Spring Harbor Publishing (1990). Any of the inactivation strategies used should take the secondary, tertiary or quaternary structure of the target antigen into consideration and preserve such structure as to optimize its immunogenicity.

Effective conditions for the production of recombinant yeast vehicles and expression of the antigen and/or other protein (e.g., an agent as described herein) by the yeast vehicle include an effective medium in which a yeast strain can be cultured. An effective medium is typically an aqueous medium comprising assimilable carbohydrate, nitrogen and phosphate sources, as well as appropriate salts, minerals, metals and other nutrients, such as vitamins and growth factors. The medium may comprise complex nutrients or may be a defined minimal medium. Yeast strains of the present invention can be cultured in a variety of containers, including, but not limited to, bioreactors, Erlenmeyer flasks, test tubes, microtiter dishes, and Petri plates. Culturing is carried out at a temperature, pH and oxygen content appropriate for the yeast strain. Such culturing conditions are well within the expertise of one of ordinary skill in the art (see, for example, Guthrie et al. (eds.), 1991, Methods in Enzymology, vol. 194, Academic Press, San Diego).

In some aspects of the invention, the yeast are grown under neutral pH conditions, and particularly, in a media maintained at a pH level of at least 5.5, namely the pH of the culture media is not allowed to drop below pH 5.5. In other aspects, the yeast is grown at a pH level maintained at about 5.5. One of skill in the art will appreciate that the culturing process includes not only the start of the yeast culture but the maintenance of the culture as well. As yeast culturing is known to turn acidic (i.e., lowering the pH) over time, care must be taken to monitor the pH level during the culturing process. This process is described in detail in WO 2008/097863, published 14 Aug. 2008.

Yeast vehicles can be formulated into yeast-based immunotherapy compositions or products of the present invention, including preparations to be administered to a subject directly or first loaded into a carrier, using a number of techniques known to those skilled in the art. For example, yeast vehicles can be dried by lyophilization. Formulations comprising yeast vehicles can also be prepared by packing yeast in a cake or a tablet, such as is done for yeast used in baking or brewing operations. In addition, yeast vehicles can be mixed with a pharmaceutically acceptable excipient, such as an isotonic buffer that is tolerated by a host or host cell. Examples of such excipients include water, saline, Ringer's solution, dextrose solution, Hank's solution, and other aqueous physiologically balanced salt solutions. Nonaqueous vehicles, such as fixed oils, sesame oil, ethyl oleate, or triglycerides may also be used. Other useful formulations include suspensions containing viscosity-enhancing agents, such as sodium carboxymethylcellulose, sorbitol, glycerol or dextran. Excipients can also contain minor amounts of additives, such as substances that enhance isotonicity and chemical stability. Examples of buffers include phosphate buffer, bicarbonate buffer and Tris buffer, while examples of preservatives include thimerosal, m- or o-cresol, formalin and benzyl alcohol. Standard formulations can either be liquid injectables or solids which can be taken up in a suitable liquid as a suspension or solution for injection. Thus, in a non-liquid formulation, the excipient can comprise, for example, dextrose, human serum albumin, and/or preservatives to which sterile water or saline can be added prior to administration.

Antigens Useful in the Immunotherapy Compositions of the Invention

According to the present invention, the general use herein of the term "antigen" refers: to any portion of a protein (peptide, partial protein, full-length protein), wherein the protein is naturally occurring or synthetically derived, to a cellular composition (whole cell, cell lysate or disrupted cells), to an organism (whole organism, lysate or disrupted cells) or to a carbohydrate, or other molecule, or a portion thereof. An antigen may, in some embodiments, elicit an antigen-specific immune response (e.g., a humoral and/or a cell-mediated immune response) against the same or similar antigens that are encountered by an element of the immune system (e.g., T cells, antibodies). The term "cancer antigen" can be used interchangeably herein with the terms "tumor-specific antigen", "tumor-associated antigen", "cancer-associated target" or "tumor-associated target".

An antigen can be as small as a single epitope, or larger, and can include multiple epitopes. As such, the size of an antigen can be as small as about 5-12 amino acids (e.g., a peptide) and as large as: a partial protein, a full length protein, including a multimer and fusion protein, chimeric protein, or agonist protein or peptide. In addition, antigens can include carbohydrates.

When referring to stimulation of an immune response, the term "immunogen" is a subset of the term "antigen", and therefore, in some instances, can be used interchangeably with the term "antigen". An immunogen, as used herein, describes an antigen which elicits a humoral and/or cell-mediated immune response (i.e., is immunogenic), such that administration of the immunogen to an individual mounts an antigen-specific immune response against the same or similar antigens that are encountered by the immune system of the individual.

An "immunogenic domain" of a given antigen can be any portion, fragment or epitope of an antigen (e.g., a peptide fragment or subunit or an antibody epitope or other conformational epitope) that contains at least one epitope that acts as an immunogen when administered to an animal. For example, a single protein can contain multiple different immunogenic domains. Immunogenic domains need not be linear sequences within a protein, such as in the case of a humoral immune response.

An "epitope" is defined herein as a single immunogenic site within a given antigen that is sufficient to elicit an immune response. Those of skill in the art will recognize that T cell epitopes are different in size and composition from B cell epitopes, and that epitopes presented through the Class I MHC pathway differ from epitopes presented through the Class II MHC pathway. Epitopes can be linear sequence or conformational epitopes (conserved binding regions).

Antigens useful in any of the immunotherapy compositions described herein can include any antigen(s) or immunogenic domain(s) thereof against which it is desirable to elicit an immune response, and in particular, include any antigen(s) or immunogenic domain(s) thereof for which a therapeutic immune response against such antigen would be beneficial to an individual. The antigen can include, but is not limited to: a cancer antigen, a viral antigen, an overexpressed mammalian cell surface molecule, a bacterial antigen, a fungal antigen, a protozoan antigen, a helminth antigen, an ectoparasite antigen, a mammalian cell molecule harboring one or more mutated amino acids, a protein normally expressed pre- or neo-natally by mammalian cells, a protein whose expression is induced by insertion of an epidemiologic agent (e.g. virus), a protein whose expression is induced by gene translocation, and a protein whose expression is induced by mutation of regulatory sequences.

In one aspect of the invention, antigens useful in one or more immunotherapy compositions of the invention include any cancer or tumor-associated antigen. In one aspect, the antigen includes an antigen associated with a preneoplastic or hyperplastic state. The antigen may also be associated with, or causative of cancer. Such an antigen may be a tumor-specific antigen, a tumor-associated antigen (TAA) or tissue-specific antigen, an epitope thereof, or an epitope agonist thereof. Cancer antigens include, but are not limited to, antigens from any tumor or cancer, including, but not limited to, melanomas, squamous cell carcinoma, breast cancers, head and neck carcinomas, thyroid carcinomas, soft tissue sarcomas, bone sarcomas, testicular cancers, prostatic cancers, ovarian cancers, bladder cancers, skin cancers, brain cancers, angiosarcomas, hemangiosarcomas, mast cell tumors, leukemias, lymphomas, primary hepatic cancers, lung cancers, pancreatic cancers, gastrointestinal cancers (including colorectal cancers), renal cell carcinomas, hematopoietic neoplasias and metastatic cancers thereof.

Suitable cancer antigens include but are not limited to carcinoembryonic antigen (CEA) and epitopes thereof such as CAP-1, CAP-1-6D (GenBank Accession No. M29540 or Zaremba et al., 1997, *Cancer Research* 57:4570-4577), MART-1 (Kawakami et al, *J. Exp. Med.* 180:347-352, 1994), MAGE-1 (U.S. Pat. No. 5,750,395), MAGE-3, GAGE (U.S. Pat. No. 5,648,226), GP-100 (Kawakami et al., *Proc. Nat'l Acad. Sci. USA* 91:6458-6462, 1992), MUC-1 (e.g., Jerome et al., *J. Immunol.,* 151:1654-1662 (1993)), MUC-2, mutated Ras oncoprotein (see, e.g., U.S. Pat. Nos. 7,465,454 and 7,563,447), normal and mutated p53 oncoproteins (Hollstein et al *Nucleic Acids Res.* 22:3551-3555, 1994), PSMA (prostate specific membrane antigen; Israeli et al., *Cancer Res.* 53:227-230, 1993), tyrosinase (Kwon et al *PNAS* 84:7473-7477, 1987), TRP-1 (gp75) (Cohen et al *Nucleic Acid Res.* 18:2807-2808, 1990; U.S. Pat. No. 5,840, 839), NY-ESO-1 (Chen et al *PNAS* 94: 1914-1918, 1997), TRP-2 (Jackson et al., *EMBOJ,* 11:527-535, 1992), TAG72, KSA, CA-125, PSA (prostate specific antigen; Xue et al., *The Prostate,* 30:73-78 (1997)), HER-2/neu/c-erb/B2, (U.S. Pat. No. 5,550,214), EGFR (epidermal growth factor receptor; Harris et al., *Breast Cancer Res. Treat,* 29:1-2 (1994)), hTERT, p73, B-RAF (B-Raf proto-oncogene serine/threonine-protein kinase; Sithanandam et al., (1990), *Oncogene* 5(12):1775-80), adenomatous polyposis coli (APC), Myc, von Hippel-Lindau protein (VHL), Rb-1, Rb-2, androgen receptor (AR), Smad4, MDR1 (also known as P-glycoprotein), Flt-3, BRCA-1 (breast cancer 1; U.S. Pat. No. 5,747, 282), BRCA-2 (breast cancer 2; U.S. Pat. No. 5,747,282)), Bcr-Abl, pax3-fkhr, ews-fli-1, Brachyury (GenBank Accession Nos. NP_003172.1 or $NM_{13}$ 003181.2; Edwards et al., 1996, *Genome Res.* 6:226-233), HERV-H (human endogenous retrovirus H), HERV-K (human endogenous retrovirus K), TWIST (GenBank Accession Nos. NM_000474 and NP_000465), Mesothelin (Kojima et al., 1995, *J. Biol. Chem.* 270(37):21984-90; Chang and Pastan, 1996, *Proc. Natl. Acad. Sci. U.S.A.* 93(1):136-40), NGEP (New Gene Expressed in Prostate; Bera et al., 2004, *Proc. Natl. Acad. Sci. U.S.A.* 101(9):3059-3064; Cereda et al., 2010, *Cancer Immunol. Immunother.* 59(1):63-71; GenBank Accession Nos. AAT40139 or AAT40140), modifications of such antigens and tissue specific antigens, splice variants of such antigens, and/or epitope agonists of such antigens. Other cancer antigens are known in the art. Other cancer antigens may also be identified, isolated and cloned by methods known in the art such as those disclosed in U.S. Pat. No. 4,514,506. Cancer antigens may also include one or more growth factors and splice variants of each.

In one aspect of the invention, the cancer antigen is carcinoembryonic antigen (CEA), a polypeptide comprising or consisting of epitopes thereof such as CAP-1, CAP-1-6D (GenBank Accession No. M29540 or Zaremba et al., 1997, *Cancer Research* 57:4570-4577), a modified CEA, a splice variant of CEA, an epitope agonist of such CEA proteins, and/or a fusion protein comprising at least one immunogenic domain of CEA or an agonist epitope thereof. In one aspect, the CEA is a modified CEA corresponding to the modified CEA having an amino acid sequence represented by SEQ ID NO:46 in U.S. Patent Publication No. US 2007_0048860, published Mar. 1, 2007, which is encoded by a nucleic acid sequence of SEQ ID NO:45. In one aspect, the antigen is a modified CEA having an amino acid sequence represented by SEQ ID NO:2 herein, which is encoded by a nucleic acid sequence represented by SEQ ID NO:1.

In one aspect of the invention, the antigen is a mutated Ras oncoprotein. Exemplary Ras oncoproteins have been described, for example, in U.S. Pat. Nos. 7,465,454 and 7,563,447. Ras is one example of an oncoprotein in which several mutations are known to occur at particular positions and be associated with the development of one or more types of cancer. Therefore, one can construct fusion proteins that consist of peptides containing a particular residue that is known to be mutated in certain cancers, wherein each domain contains a different mutation at that site in order to cover several or all known mutations at that site. A fusion protein useful in the present invention may have one, two, or multiple domains, wherein each domain consists of a peptide from a particular protein (the same or different proteins), each peptide consisting of at least 4 amino acid residues flanking either side of and including an epitope or mutated amino acid, such as a mutated amino acid that is found in the protein, wherein the mutation is associated with a particular disease (e.g., cancer). For example, with regard to Ras, one may provide one, two, three, or more immunogenic domains comprising at least 4 amino acids on either side of and including position 12, wherein each domain has a different substitution for the glycine that normally occurs in the non-mutated Ras protein (e.g., a substitution of a valine, a cysteine, an arginine, an aspartate, a serine, or an alanine, for the glycine). As another example, one may provide one, two, three, or more immunogenic domains comprising at least 4 amino acids on either side of and including position 13, wherein each domain has a different substitution for the glycine that normally occurs in the non-mutated Ras protein (e.g., a substitution of an aspartate for the glycine). As yet another example, one may provide one, two, three, or more immunogenic domains comprising at least 4 amino acids on either side of and including position 61, wherein each domain has a different substitution for the glutamine that normally occurs in the non-mutated Ras protein (e.g., a substitution of a leucine, an arginine, or a histidine, for the glutamine). In one example, the cancer antigen comprises fragments of at least 5-9 contiguous amino acid residues of a wild-type Ras protein containing amino acid positions 12, 13, 59, 61 or 76 relative to the wild-type Ras protein, wherein the amino acid residues at positions 12, 13, 59, 61 or 76 are mutated with respect to the wild-type Ras protein. In one aspect, the fusion protein construct consists of at least one peptide that is fused in frame with another mutated tumor antigen (e.g., a Ras protein comprising at least one mutation relative to a wild-type Ras protein sequence), wherein the peptide is selected from the group consisting of: (a) a peptide comprising at least from positions 8-16 of wild-type Ras (human or murine K-Ras, N-Ras or H-Ras), wherein the amino acid residue at position 12 with respect to wild-type Ras is mutated as compared to wild-type Ras; (b) a peptide comprising at least from positions 9-17 of wild-type Ras, wherein the amino acid residue at position 13 with respect to wild-type Ras is mutated as compared to wild-type Ras; (c) a peptide comprising at least from positions 55-63 of wild-type Ras, wherein the amino acid residue at position 59 with respect to SEQ ID NO:3 is mutated as compared to wild-type Ras; (d) a peptide comprising at least from positions 57-65 of wild-type Ras, wherein the amino acid residue at position 61 with respect to wild-type Ras is mutated as compared to wild-type Ras; or (e) a peptide comprising at least from positions 72-80 of wild-type Ras, wherein the amino acid residue at position 76 with respect to wild-type Ras is mutated as compared to wild-type Ras. It is noted that these positions are identical among human and mouse K-Ras, N-Ras and H-Ras, since human and mouse sequences are identical in this region of the protein and since K-Ras, H-Ras and N-Ras are identical in this region. In one aspect, the a Ras fusion protein suitable for use as an antigen in the present invention is selected from: SEQ ID NO:4 (encoded by a nucleic acid sequence represented herein as SEQ ID NO:3), SEQ ID NO:6 (encoded by a nucleic acid sequence represented herein as SEQ ID NO:5), SEQ ID NO:8 (encoded by a nucleic acid sequence represented herein as SEQ ID NO:7), and/or SEQ ID NO:10 (encoded by a nucleic acid sequence represented herein as SEQ ID NO:9).

In one aspect of the invention, the antigen is human Brachyury. The amino acid sequence for human Brachyury is represented herein by SEQ ID NO:15, which is encoded by a nucleic acid sequence represented by SEQ ID NO:14.

In another aspect of the invention, antigens useful in one or more immunotherapy compositions of the invention include any antigens associated with a pathogen or a disease or condition caused by or associated with a pathogen. Such antigens include, but are not limited to, viral antigens, fungal antigens, bacterial antigens, helminth antigens, parasitic antigens, ectoparasite antigens, protozoan antigens, or antigens from any other infectious agent.

In one aspect, the antigen is from virus, including, but not limited to, adenoviruses, arena viruses, bunyaviruses, coronaviruses, coxsackie viruses, cytomegaloviruses, Epstein-Barr viruses, flaviviruses, hepadnaviruses, hepatitis viruses, herpes viruses, influenza viruses, lentiviruses, measles viruses, mumps viruses, myxoviruses, orthomyxoviruses, papilloma viruses, papovaviruses, parainfluenza viruses, paramyxoviruses, parvoviruses, picornaviruses, poxviruses, rabies viruses, respiratory syncytial viruses, reoviruses, rhabdoviruses, rubella viruses, togaviruses, and varicella viruses. Other viruses include T-lymphotrophic viruses, such as human T-cell lymphotrophic viruses (HTLVs, such as HTLV-I and HTLV-II), bovine leukemia viruses (BLVS) and feline leukemia viruses (FLVs). The lentiviruses include, but are not limited to, human (HIV, including HIV-1 or HIV-2), simian (SIV), feline (FIV) and canine (CIV) immunodeficiency viruses. In one embodiment, viral antigens include those from non-oncogenic viruses.

In another aspect, the antigen is from an infectious agent from a genus selected from: *Aspergillus, Bordatella, Brugia, Candida, Chlamydia, Coccidia, Cryptococcus, Dirofilaria, Escherichia, Francisella, Gonococcus, Histoplasma, Leishmania, Mycobacterium, Mycoplasma, Paramecium, Pertussis, Plasmodium, Pneumococcus, Pneumocystis, Rickettsia, Salmonella, Shigella, Staphylococcus, Streptococcus, Toxoplasma, Vibriocholerae*, and *Yersinia*. In one aspect, the infectious agent is selected from *Plasmodium falciparum* or *Plasmodium vivax*.

In one aspect, the antigen is from a bacterium from a family selected from: Enterobacteriaceae, Micrococcaceae, Vibrionaceae, Pasteurellaceae, Mycoplasmataceae, and Rickettsiaceae. In one aspect, the bacterium is of a genus selected from: *Pseudomonas, Bordetella, Mycobacterium, Vibrio, Bacillus, Salmonella, Francisella, Staphylococcus, Streptococcus, Escherichia, Enterococcus, Pasteurella*, and *Yersinia*. In one aspect, the bacterium is from a species selected from: *Pseudomonas aeruginosa, Pseudomonas mallei, Pseudomonas pseudomallei, Bordetella pertussis, Mycobacterium tuberculosis, Mycobacterium leprae, Francisella tularensis, Vibrio cholerae, Bacillus anthracis, Salmonella enteric, Yersinia pestis, Escherichia coli* and *Bordetella bronchiseptica*.

In one aspect, the antigen is from a fungus, such a fungus including, but not limited to, a fungus from *Saccharomyces* spp., *Aspergillus* spp., *Cryptococcus* spp., *Coccidioides* spp., *Neurospora* spp., *Histoplasma* spp., or *Blastomyces* spp. In one aspect, the fungus is from a species selected from: *Aspergillus fumigatus, A. flavus, A. niger, A. terreus, A. nidulans, Coccidioides immitis, Coccidioides posadasii* or *Cryptococcus neoformans*. The most common species of *Aspergillus* causing invasive disease include *A. fumigatus, A. flavus, A. niger, A. terreus* and *A. nidulans*, and may be found, for example, in patients who have immunosuppression or T-cell or phagocytic impairment. *A. fumigatus* has been implicated in asthma, aspergillomas and invasive aspergillosis. Coccidioidomycosis, also known as San Joaquin Valley Fever, is a fungal disease caused by *Coccidioides immitis*, and can lead to acute respiratory infections and chronic pulmonary conditions or dissemination to the meninges, bones, and joints. Cryptococcosis-associated conditions are also targeted by methods of the invention, for example, in a non-immunosuppressed or immunosuppressed subject, such as a subject who is infected with HIV.

In some embodiments, the antigen is a fusion protein. In one aspect of the invention, a fusion protein can include two or more antigens. In one aspect, the fusion protein can include two or more immunogenic domains and/or two or more epitopes of one or more antigens. Any combination of antigens, immunogenic domains thereof, and/or epitopes thereof are contemplated for use in the compositions of the invention. An immunotherapeutic composition containing such antigens, immunogenic domains thereof, and/or epitopes thereof may provide antigen-specific immunization in a broad range of patients. For example, a fusion protein useful in the present invention may have multiple domains (two or more domains), wherein each domain consists of a peptide or polypeptide from a particular protein, the peptide or polypeptide consisting of at least 4 amino acid residues flanking either side of and including a mutated amino acid that is found in the protein, wherein the mutation is associated with a particular disease or condition.

In one embodiment, fusion proteins that are used as a component of the yeast-based immunotherapeutic composition useful in the invention are produced using constructs that are particularly useful for the expression of heterologous antigens in yeast. Typically, the desired antigenic protein(s) or peptide(s) are fused at their amino-terminal end to: (a) a specific synthetic peptide that stabilizes the expression of the fusion protein in the yeast vehicle or prevents posttranslational modification of the expressed fusion protein (such peptides are described in detail, for example, in U.S. Patent Publication No. 2004-0156858 A1, published Aug. 12, 2004, incorporated herein by reference in its entirety); (b) at least a portion of an endogenous yeast protein, wherein either fusion partner provides significantly enhanced stability of expression of the protein in the yeast and/or a prevents post-translational modification of the proteins by the yeast cells (such proteins are also described in detail, for example, in U.S. Patent Publication No. 2004-0156858 A1, supra); and/or (c) at least a portion of a yeast protein that causes the fusion protein to be expressed on the surface of the yeast (e.g., an Aga protein, as described in detail in WO 2008/019366). In addition, the present invention includes the use of peptides that are fused to the C-terminus of the antigen-encoding construct, particularly for use in the selection and identification of the protein. Such peptides include, but are not limited to, any synthetic or natural peptide, such as a peptide tag (e.g., 6×His) or any other short epitope tag. Peptides attached to the C-terminus of an antigen according to the invention can be used with or without the addition of the N-terminal peptides discussed above.

According to the invention, in one embodiment, the two or more different immunotherapy compositions preferably target the same antigen(s). In this embodiment, the same antigen(s) or immunogenic domain(s) thereof are typically expressed by each of the immunotherapy composition vectors, although the antigen(s) and/or immunogenic domain(s) thereof may be admixed with one or both of the compositions, and/or in the case of the yeast-based immunotherapy composition, the antigen may be attached to the yeast vehicle and/or carried inside the yeast vehicle. In one embodiment, both compositions may target the same antigen(s), although each composition may target a different epitope(s) or immunogenic domain(s) within the same antigen. In one embodiment, each immunotherapy compositions targets a different antigen(s) and/or immunogenic domain and/or epitope thereof. For example, it may be advantageous to target one antigen, such as Ras, using one composition and another cancer antigen that is also expressed in the same or a subset of the same cancers, such as CEA, using the other immunotherapy composition. In another embodiment, a combination of one type of immunotherapy composition is provided, wherein there are at least two different antigen compositions within the same type (e.g., a combination of a yeast-based immunotherapy composition expressing mutated Ras or a fusion protein comprising multiple immunogenic domains of mutated Ras, and a yeast-based immunotherapy composition expressing CEA or a modified CEA as described herein). This combination is administered concurrently with the other type of immunotherapy composition (e.g., a virus-based composition) that expresses the same or different antigen(s). In one aspect of such an embodiment, the various combinations can be mixed or in another aspect, need not be physically mixed, but can rather be administered concurrently such as to the same site or different sites, or within the same administration period. In yet another embodiment, one of the two or more different immunotherapy compositions targets one or more antigens, and the other of the immunotherapy compositions is provided as an adjuvant, without necessarily targeting any antigen (i.e., the composition is used for its non-antigen-specific immunotherapy benefits), or without necessarily targeting the same cancer antigen as the other composition. More particularly, because each of the immunotherapy vectors described herein has been show to contribute vector-specific effects to the efficacy of the composition, in some embodiments, only one vector may be associated with or express the antigen, and the other vector is used concurrently to contribute non-antigen-specific immunotherapy effects.

Methods of Use of the Compositions of the Invention

In the methods of the present invention, two or more immunotherapy compositions as described herein are first administered concurrently to an individual. As used herein with respect to administration of a composition, the term "concurrently" means to administer each of the compositions, and particularly, the first dose of such compositions, essentially at the same time or within the same dosing period, or within a time period during which the initial effects of priming of the immune system by the immunotherapy compositions occur (e.g., within 1-2 days and preferably less). For clarity, concurrent administration does not require administration of all of the compositions at precisely the same moment, but rather, the administration of all compositions should occur within one scheduled dosing of the patient in order to prime the immune system with each of the compositions concurrently (e.g., one composition may be administered first, followed immediately or closely by the administration of the second composition, and so on). In some circumstances, such as when the compositions are administered to the same site, the compositions may be provided in admixture, although even when administered at the same site, sequential administration of each composition during the same dosing period may be preferred. In one aspect, the compositions are administered within the same 1-2 days, and in one aspect, on the same day, and in one aspect, within the same 12 hour period, and in one aspect, within the same 8 hour period, and in one aspect, within the same 4 hour period, and in one aspect, within the same 1, 2 or 3 hour period, and in one aspect, within the same 1, 2, 3, 4, 6, 7, 8, 9, or 10 minutes.

In some circumstances, either the first or the second immunotherapy composition is administered more frequently than the other. For example, in one aspect, when the first immunotherapy composition is a virus-based immunotherapy composition, and the second immunotherapy composition is a yeast-based immunotherapy composition, the second immunotherapy composition may be administered more frequently than the first immunotherapy composition. For example, in one aspect, in between concurrent administrations of the first and second immunotherapy composition, the second immunotherapy composition may be administered one, two, three or more additional times. For instance, because the immunization with the virus-based immunotherapy composition results in extended presentation of antigen, it may not be necessary or beneficial to administer this composition on shorter frequencies, whereas yeast-based immunotherapy compositions present discrete bolus' of antigen, and so they can be administered more frequently without fears of inhibiting the immune response. For example, in one aspect, the virus-based immunotherapy composition is administered every 2, 3 or 4 or more weeks, while yeast-based immunotherapy compositions are administered at 1 week intervals, which may be extended to longer intervals (2, 3 or 4 weeks or more) as the total period of therapy increases.

In one embodiment of the invention, the two or more immunotherapy compositions are administered concurrently, but to different physical sites in the patient. For example, one composition can be administered to a site on one side of the individual's body and the other composition can be administered to a site on the other side of the individual's body. As another example, one composition can be administered at a site near a particular draining lymph node, and the other composition can be administered at a site near a different draining lymph node. In another embodiment, the two or more different immunotherapy compositions are administered concurrently and to the same or substantially adjacent sites in the patient. A substantially adjacent site is a site that is not precisely the same injection site to which the first composition is administered, but that is in close proximity (is next to or near to) the first injection site. In one embodiment, the two or more different immunotherapy compositions are administered in admixture. In one aspect of the invention, a virus-based immunotherapy composition is administered subcutaneously, intramuscularly, or intratumorally, and a yeast-based composition of the invention is administered subcutaneously.

Some embodiments may include combinations of administration approaches. For example, using the exemplary case of concurrent administration of a yeast-based immunotherapy composition (a first composition) and a virus-based immunotherapy composition (a second composition), one portion of the dose of the yeast-based composition (e.g., one fraction of the total dose of yeast-based composition) may be administered in admixture with or to the same or adjacent site as a portion of or all of the dose of the virus-based immunotherapy composition, and then the remaining portion(s) of the dose of the yeast-based immunotherapy composition are administered to other site(s) in the individual. Similarly, a portion of the dose of the virus-based composition can be administered in admixture with or to the same or adjacent site as a portion of or all of the dose of the yeast-based composition, and then the remaining portion(s) of the virus-based immunotherapy composition are administered to other site(s) in the individual. In one embodiment, within a single dose amount of virus-based and/or yeast-based immunotherapy composition that is to be administered in portions to different sites on the individual, some portions may contain or express the target antigen and others may not (i.e., the others may be empty vectors or encode a costimulatory molecule, cytokine, or other non-antigen agent).

Administration of a vaccine or composition can be systemic, mucosal and/or proximal to the location of the target site (e.g., near a tumor). The preferred routes of administration will be apparent to those of skill in the art, depending on the type of condition to be prevented or treated, the antigen used, and/or the target cell population or tissue. Various acceptable methods of administration include, but are not limited to, intravenous administration, intraperitoneal administration, intramuscular administration, intranodal administration, intracoronary administration, intraarterial administration (e.g., into a carotid artery), subcutaneous administration, transdermal delivery, intratracheal administration, subcutaneous administration, intraarticular administration, intraventricular administration, inhalation (e.g., aerosol), intracranial, intraspinal, intraocular, aural, intranasal, oral, pulmonary administration, impregnation of a catheter, and direct injection into a tissue. In one aspect, routes of administration include: intravenous, intraperitoneal, subcutaneous, intradermal, intranodal, intramuscular, transdermal, inhaled, intranasal, oral, intraocular, intraarticular, intracranial, and intraspinal. Parenteral delivery can include intradermal, intramuscular, intraperitoneal, intrapleural, intrapulmonary, intravenous, subcutaneous, atrial catheter and venal catheter routes. Aural delivery can include ear drops, intranasal delivery can include nose drops or intranasal injection, and intraocular delivery can include eye drops. Aerosol (inhalation) delivery can also be performed using methods standard in the art (see, for example, Stribling et al., Proc. Natl. Acad. Sci. USA 189:11277-11281, 1992, which is incorporated herein by reference in its entirety). Other routes of administration that modulate mucosal immunity are useful in the treatment of viral infections. Such routes include bronchial, intradermal, intramuscular, intranasal, other inhalatory, rectal, subcutaneous, topical, transdermal, vaginal and urethral routes. In one aspect, an immunotherapeutic composition of the invention is administered subcutaneously. Preferred methods of administration include, but are not limited to, intravenous, intraperitoneal, subcutaneous, intradermal, intranodal, intramuscular, transdermal or intratumoral. The dose is administered at least once. Subsequent doses may be administered as indicated, and are typically utilized.

More particularly, in one embodiment, the initial concurrent administration of the two or more different immunotherapy compositions of the invention may be followed by subsequent booster doses of one and in one embodiment, both or all, immunotherapy compositions. Booster doses (boosts) may be administered any suitable period apart, and are typically administered 1, 2, 3, 4, 5, 6, 7, or 8 weeks apart. The booster doses of the two or more immunotherapy compositions may be administered concurrently or separately, as desired, but are most typically administered concurrently, as with the priming dose. As with the priming dose, the method of administration can use any combination of sites and administration strategies as described above for the priming dose, but is not limited to the same administration protocol as for the priming dose. For example, if the priming doses were administered to two different sites (one immunotherapy composition at each site), the boosting doses can be administered to the same two sites, to a single site or adjacent sites, or to two different sites, or using the portioning strategy described above.

In addition, the booster doses need not be formulated in exactly the same way as the priming doses. For example, if the each of the immunotherapy compositions in the priming dose provided an antigen(s) and/or immunogenic domain(s) thereof, in the booster dose, both immunotherapy compositions may again provide the antigen(s) and/or immunogenic domain(s) thereof, or only one of the immunotherapy compositions may provide the antigen(s) and/or immunogenic domain(s) thereof, and the other immunotherapy composition may be an empty vector or provide non-antigen agents (e.g., immunostimulatory molecules or other agents). Other possible modification of the compositions as described herein is also contemplated during the boosting stage, including modifications or changes of the viral vector used (e.g., using vaccinia virus in a priming composition and fowlpox virus in a boosting composition, or vice versa), modifications or changes in a yeast vehicle (e.g., change in yeast strain, change in yeast production method, change in how the yeast provides the antigen, such as expressed versus in admixture), dose amounts, antigens or domains provided by one or more of the compositions, and inclusion or elimination or substitution of immunostimulatory molecules or other agents.

The term "unit dose" as it pertains to the inoculum of a composition of the invention refers to physically discrete units suitable as unitary dosages for mammals, each unit containing a predetermined quantity of immunotherapy composition calculated to produce the desired immunogenic effect in association with the required diluent. The specifications for the novel unit dose of an inoculum of this invention are dictated by and are dependent upon the unique characteristics of the particular immunotherapy composition and the particular immunologic effect to be achieved. In providing an individual with an immunotherapy composition of the present invention, preferably a human, the dosage of administered recombinant vector will vary depending upon such factors as the individual's age, weight, height, sex, general medical condition, previous medical history, disease progression, tumor burden, pathogen burden and the like.

The inoculum is typically prepared as a solution in tolerable (acceptable) diluent such as saline, phosphate-buffered saline or other physiologically tolerable diluent and the like to form an aqueous pharmaceutical composition.

With respect to the recombinant virus-based immunotherapy compositions of the invention, in general, it is desirable to provide the recipient with a dosage of recombinant virus in the range of about $10^5$ to about $10^{10}$ plaque forming units, although a lower or higher dose may be administered, including, but not limited to, $10^2$, $10^3$, $10^4$, $10^5$, $10^6$, $10^7$, $10^8$, $10^9$ $10^{10}$, $10^{11}$ or more plaque forming units. Examples of methods for administering the recombinant viral vector into individuals include, but are not limited to, exposure of tumor cells to the recombinant virus ex vivo, or injection of the recombinant vector into the affected host by intravenous, subcutaneous (S.C.), intradermal (I.D.) or intramuscular (I.M.) administration of the virus. Alternatively the recombinant viral vector or combination of recombinant viral vectors may be administered locally by direct injection into a cancerous lesion or tumor or topical application in a pharmaceutically acceptable carrier. The quantity of recombinant vector carrying the nucleic acid sequence of one or more antigens in combination with nucleic acid sequences encoding multiple costimulatory molecules to be administered is based on the titer of virus particles. A preferred range of the antigen to be administered is $10^5$ to $10^{10}$ virus particles per mammal, preferably a human, although a lower or higher dose may be administered, including, but not limited to, $10^2$, $10^3$, $10^4$, $10^5$, $10^6$, $10^7$, $10^8$, $10^9$ $10^{10}$, $10^{11}$ or more plaque forming units.

With respect to the yeast-based immunotherapy compositions of the invention, in general, a suitable single dose is a dose that is capable of effectively providing a yeast vehicle and an antigen (if included) to a given cell type, tissue, or region of the patient body in an amount effective to elicit an antigen-specific immune response, when administered one or more times over a suitable time period. For example, in one embodiment, a single dose of a yeast vehicle of the present invention is from about $1 \times 10^5$ to about $5 \times 10^7$ yeast cell equivalents per kilogram body weight of the organism being administered the composition. More preferably, a single dose of a yeast vehicle of the present invention is from about 0.1 Y.U. ($1 \times 10^6$ cells) to about 100 Y.U. ($1 \times 10^9$ cells) per dose (i.e., per organism), including any interim dose, in increments of $0.1 \times 10^6$ cells (i.e., $1.1 \times 10^6$, $1.2 \times 10^6$, $1.3 \times 10^6$ . . . ). Preferred doses include doses between 1 Y.U and 40 Y.U. and more preferably, between 10 Y.U. and 40 Y.U. In one embodiment, the doses are administered at different sites on the individual but during the same dosing period. For example, a 40 Y.U. dose may be administered via by injecting 10 Y.U. doses to four different sites on the individual during one dosing period.

If the mammal to be immunized is already afflicted with a disease (e.g., cancer or metastatic cancer or a chronic pathogen infection), the vaccine can be administered in conjunction with other therapeutic treatments used to treat the disease (e.g., chemotherapy, radiation therapy, small molecule therapy, cytokine therapy, anti-viral therapy, biological response modifier therapy, surgery, etc.), in addition to the concurrent administration of the different immunotherapy compositions described herein.

The method of use of the immunotherapy compositions of the present invention elicits an immune response in an individual such that the individual is protected from the disease or condition, or from symptoms resulting from the disease or condition. As used herein, the phrase "protected from a disease" refers to preventing a disease, preventing at least one symptom of the disease, delaying onset of a disease, reducing one or more symptoms of the disease, reducing the occurrence of the disease, and/or reducing the severity of the disease. With respect to cancer, concurrent administration of the immunotherapy compositions of the invention preferably results in one or more of: prevention of tumor growth, delay to onset of disease, reduction of tumor burden, reduction of tumor growth, increased survival, improved organ function, and/or improved general health of the individual. With respect to infectious disease and other diseases, concurrent administration of the immunotherapy compositions preferably results in one or more of: prevention of the disease or condition, prevention of infection, delay to onset of disease, increased survival, reduction of pathogen burden (e.g., reduction of viral titer), reduction in at least one symptom resulting from the infection in the individual, reduction of organ or system damage resulting from the infection or disease, and improvement in organ or system function.

In the method of treatment of the present invention, the administration of the immunotherapy compositions of the invention may be either "prophylactic" or "therapeutic". When provided prophylactically, the immunotherapy compositions of the present invention are provided in advance of any symptom of a disease or condition. The prophylactic administration of the immunotherapy compositions serves to prevent or ameliorate or delay time to onset of any subsequent disease. When provided therapeutically, the immunotherapy compositions are provided at or after the onset of a symptom of disease. The term, "disease" refers to any deviation from the normal health of an animal and includes a state when disease symptoms are present, as well as conditions in which a deviation (e.g., tumor growth, infection, etc.) has occurred, but symptoms are not yet manifested.

In any embodiment of the invention, in addition to administration of the immunotherapy compositions of the invention to an individual, additional exogenous immunomodulators or immunostimulatory molecules, chemotherapeutic drugs, antibiotics, antifungal drugs, antiviral drugs, cancer therapies, cytokines, and other therapeutic agents, therapeutic compositions, or therapeutic protocols, alone or in combination, may be administered, depending on the condition to be treated. Suitable biological response modifiers that may be used in conjunction with the immunotherapy compositions of the invention include, but are not limited to, cytokines, chemokines, hormones, lipidic derivatives, peptides, proteins, polysaccharides, small molecule drugs, antibodies and antigen binding fragments thereof (including, but not limited to, anti-cytokine antibodies, anti-cytokine receptor antibodies, anti-chemokine antibodies), vitamins, polynucleotides, nucleic acid binding moieties, aptamers, and growth modulators. Examples of exogenously added agents and biological response modifiers include, but are not limited to, Flt-3L, cyclophosphamide, cisplatinum, gancyclovir, amphotericin B, 5 fluorouracil, interleukin 2 (IL-2), interleukin 4 (IL-4), IL-6, interleukin 10 (IL-10), interleukin 12 (IL-12), type I interferon (including IFN-α) or agonists or antagonists of type I interferon or a receptor thereof; type II interferon (including IFN-γ) or agonists or antagonists of type II interferon or a receptor thereof; type III interferon (including IFN-λ) or agonists or antagonists of type III interferon or a receptor thereof; tumor necrosis factor-α (TNF-α); transforming growth factor-β (TGF-β); anti-CD40; CD40L; anti-CTLA-4 antibody (e.g., to release anergic T cells); T cell co-stimulators (e.g., anti-CD137, anti-CD28, anti-CD40); alemtuzumab (e.g., CAMPATH®), denileukin diftitox (e.g., ONTAK®); anti-CD4; anti-CD25; anti-PD-1, anti-PD-L1, anti-PD-L2; agents that block FOXP3 (e.g., to abrogate the activity/kill CD4+/CD25+ T regulatory cells); Flt3 ligand, imiquimod (ALDARA™), granulocyte-macrophage colony stimulating factor (GM-CSF); granulocyte-colony stimulating factor (G-CSF), sargramostim (LEUKINE®); hormones including without limitation prolactin and growth hormone; Toll-like receptor (TLR) agonists, including but not limited to TLR-2 agonists, TLR-4 agonists, TLR-7 agonists, and TLR-9 agonists; TLR antagonists, including but not limited to TLR-2 antagonists, TLR-4 antagonists, TLR-7 antagonists, and TLR-9 antagonists; anti-inflammatory agents and immunomodulators, including but not limited to, COX-2 inhibitors (e.g., Celecoxib, NSAIDS), glucocorticoids, statins, and thalidomide and analogues thereof including IMID™s (which are structural and functional analogues of thalidomide (e.g., REVLIMID® (lenalidomide), ACTIMID® (pomalidomide)); proinflammatory agents, such as fungal or bacterial components or any proinflammatory cytokine or chemokine; immunotherapeutic vaccines including, but not limited to, virus-based vaccines, bacteria-based vaccines, or antibody-based vaccines; and any other immunomodulators, immunopotentiators, anti-inflammatory agents, and/or pro-inflammatory agents.

These exogenous agents and therapies may be administered concurrently with the immunotherapy compositions of the invention, or at different time points. For example, when given to an individual in conjunction with chemotherapy, it may be desirable to administer the immunotherapy compositions during the "holiday" between chemotherapeutic doses, in order to maximize the efficacy of the immunotherapy compositions.

Compositions and therapeutic vaccines of the invention can further include any other compounds that are useful for protecting a subject from a particular disease or condition, including an infection by a pathogen, any compounds that treat or ameliorate any symptom of such an infection, and any compounds or treatments for cancer.

In the method of the present invention, compositions and therapeutic compositions can be administered to animal, including any vertebrate, and particularly to any member of the Vertebrate class, Mammalia, including, without limitation, primates, rodents, livestock and domestic pets. Livestock include mammals to be consumed or that produce useful products (e.g., sheep for wool production). Mammals to protect include humans, dogs, cats, mice, rats, goats, sheep, cattle, horses and pigs.

General Techniques Useful in the Invention

The practice of the present invention will employ, unless otherwise indicated, conventional techniques of molecular biology (including recombinant techniques), microbiology, cell biology, biochemistry, nucleic acid chemistry, and immunology, which are well known to those skilled in the art. Such techniques are explained fully in the literature, such as, Methods of Enzymology, Vol. 194, Guthrie et al., eds., Cold Spring Harbor Laboratory Press (1990); Biology and activities of yeasts, Skinner, et al., eds., Academic Press (1980); Methods in yeast genetics: a laboratory course manual, Rose et al., Cold Spring Harbor Laboratory Press (1990); The Yeast *Saccharomyces*: Cell Cycle and Cell Biology, Pringle et al., eds., Cold Spring Harbor Laboratory Press (1997); The Yeast *Saccharomyces*: Gene Expression, Jones et al., eds., Cold Spring Harbor Laboratory Press (1993); The Yeast *Saccharomyces*: Genome Dynamics, Protein Synthesis, and Energetics, Broach et al., eds., Cold Spring Harbor Laboratory Press (1992); Molecular Cloning: A Laboratory Manual, second edition (Sambrook et al., 1989) and Molecular Cloning: A Laboratory Manual, third edition (Sambrook and Russel, 2001), (jointly referred to herein as "Sambrook"); Current Protocols in Molecular Biology (F. M. Ausubel et al., eds., 1987, including supplements through 2001); PCR: The Polymerase Chain Reaction, (Mullis et al., eds., 1994); Harlow and Lane (1988) Antibodies, A Laboratory Manual, Cold Spring Harbor Publications, New York; Harlow and Lane (1999) Using Antibodies: A Laboratory Manual Cold Spring Harbor Laboratory Press, Cold Spring Harbor, N.Y. (jointly referred to herein as "Harlow and Lane"), Beaucage et al. eds., Current Protocols in Nucleic Acid Chemistry John Wiley & Sons, Inc., New York, 2000); Casarett and Doull's Toxicology The Basic Science of Poisons, C. Klaassen, ed., 6th edition (2001), and Vaccines, S. Plotkin and W. Orenstein, eds., 3rd edition (1999).

General Definitions

An "immunotherapeutic composition" is a composition that elicits an immune response sufficient to achieve at least one therapeutic benefit in a subject.

In general, the term "biologically active" indicates that a compound has at least one detectable activity that has an effect on the metabolic or other processes of a cell or organism, as measured or observed in vivo (i.e., in a natural physiological environment) or in vitro (i.e., under laboratory conditions). Accordingly, a biologically active portion or fragment or domain of a protein, for example, refers to a portion, fragment or domain that is of sufficient size to have a biological activity of the full-length protein. Such activity is an activity that is particular to that protein, rather than an activity of all proteins as a class.

An "individual" or a "subject" or a "patient", which terms may be used interchangeably, is a vertebrate, preferably a mammal, more preferably a human. Mammals include, but are not limited to, farm animals, sport animals, pets, primates, mice and rats.

According to the present invention, the term "modulate" can be used interchangeably with "regulate" and refers generally to upregulation or downregulation of a particular activity. As used herein, the term "upregulate" can be used generally to describe any of: elicitation, initiation, increasing, augmenting, boosting, improving, enhancing, amplifying, promoting, or providing, with respect to a particular activity. Similarly, the term "downregulate" can be used generally to describe any of: decreasing, reducing, inhibiting, ameliorating, diminishing, lessening, blocking, or preventing, with respect to a particular activity.

Reference to an isolated protein or polypeptide in the present invention includes full-length proteins, fusion proteins, or any fragment, domain, conformational epitope, or homologue of such proteins. More specifically, an isolated protein, according to the present invention, is a protein (including a polypeptide or peptide) that has been removed from its natural milieu (i.e., that has been subject to human manipulation) and can include purified proteins, partially purified proteins, recombinantly produced proteins, and synthetically produced proteins, for example. As such, "isolated" does not reflect the extent to which the protein has been purified. Preferably, an isolated protein of the present invention is produced recombinantly. According to the present invention, the terms "modification" and "mutation" can be used interchangeably, particularly with regard to the modifications/mutations to the amino acid sequence of proteins or portions thereof (or nucleic acid sequences) described herein.

As used herein, the term "homologue" is used to refer to a protein or peptide which differs from a naturally occurring protein or peptide (i.e., the "prototype" or "wild-type" protein) by minor modifications to the naturally occurring protein or peptide, but which maintains the basic protein and side chain structure of the naturally occurring form. Such changes include, but are not limited to: changes in one or a few amino acid side chains; changes one or a few amino acids, including deletions (e.g., a truncated version of the protein or peptide) insertions and/or substitutions; changes in stereochemistry of one or a few atoms; and/or minor derivatizations, including but not limited to: methylation, glycosylation, phosphorylation, acetylation, myristoylation, prenylation, palmitation, amidation and/or addition of glycosylphosphatidyl inositol. A homologue can have enhanced, decreased, or substantially similar properties as compared to the naturally occurring protein or peptide. A homologue can include an agonist of a protein or an antagonist of a protein. Homologues can be produced using techniques known in the art for the production of proteins including, but not limited to, direct modifications to the isolated, naturally occurring protein, direct protein synthesis, or modifications to the nucleic acid sequence encoding the protein using, for example, classic or recombinant DNA techniques to effect random or targeted mutagenesis.

A homologue of a given protein may comprise, consist essentially of, or consist of, an amino acid sequence that is at least about 45%, or at least about 50%, or at least about 55%, or at least about 60%, or at least about 65%, or at least about 70%, or at least about 75%, or at least about 80%, or at least about 85%, or at least about 90%, or at least about 95% identical, or at least about 95% identical, or at least about 96% identical, or at least about 97% identical, or at least about 98% identical, or at least about 99% identical (or any percent identity between 45% and 99%, in whole integer increments), to the amino acid sequence of the reference protein. In one embodiment, the homologue comprises, consists essentially of, or consists of, an amino acid sequence that is less than 100% identical, less than about 99% identical, less than about 98% identical, less than about 97% identical, less than about 96% identical, less than about 95% identical, and so on, in increments of 1%, to less than about 70% identical to the naturally occurring amino acid sequence of the reference protein.

As used herein, unless otherwise specified, reference to a percent (%) identity refers to an evaluation of homology which is performed using: (1) a BLAST 2.0 Basic BLAST homology search using blastp for amino acid searches and blastn for nucleic acid searches with standard default parameters, wherein the query sequence is filtered for low complexity regions by default (described in Altschul, S. F., Madden, T. L., Schääffer, A. A., Zhang, J., Zhang, Z., Miller, W. & Lipman, D. J. (1997) "Gapped BLAST and PSI-BLAST: a new generation of protein database search programs." Nucleic Acids Res. 25:3389-3402, incorporated herein by reference in its entirety); (2) a BLAST 2 alignment (using the parameters described below); (3) and/or PSI-BLAST with the standard default parameters (Position-Specific Iterated BLAST. It is noted that due to some differences in the standard parameters between BLAST 2.0 Basic BLAST and BLAST 2, two specific sequences might be recognized as having significant homology using the BLAST 2 program, whereas a search performed in BLAST 2.0 Basic BLAST using one of the sequences as the query sequence may not identify the second sequence in the top matches. In addition, PSI-BLAST provides an automated, easy-to-use version of a "profile" search, which is a sensitive way to look for sequence homologues. The program first performs a gapped BLAST database search. The PSI-BLAST program uses the information from any significant alignments returned to construct a position-specific score matrix, which replaces the query sequence for the next round of database searching. Therefore, it is to be understood that percent identity can be determined by using any one of these programs.

Two specific sequences can be aligned to one another using BLAST 2 sequence as described in Tatusova and Madden, (1999), "Blast 2 sequences—a new tool for comparing protein and nucleotide sequences", FEMS Microbiol Lett. 174:247-250, incorporated herein by reference in its entirety. BLAST 2 sequence alignment is performed in blastp or blastn using the BLAST 2.0 algorithm to perform a Gapped BLAST search (BLAST 2.0) between the two sequences allowing for the introduction of gaps (deletions and insertions) in the resulting alignment. For purposes of clarity herein, a BLAST 2 sequence alignment is performed using the standard default parameters as follows.

For blastn, using 0 BLOSUM62 matrix:
Reward for match=1
Penalty for mismatch=-2
Open gap (5) and extension gap (2) penalties
gap x_dropoff (50) expect (10) word size (11) filter (on)
For blastp, using 0 BLOSUM62 matrix:
Open gap (11) and extension gap (1) penalties
gap x_dropoff (50) expect (10) word size (3) filter (on).

As used herein, an "agonist" is any compound or agent, including without limitation small molecules, proteins, peptides, antibodies, nucleic acid binding agents, etc., that binds to a receptor or ligand or interacts with another molecule or within a chemical or biological system and produces or triggers a response, which may include agents that mimic the action of a naturally occurring substance (e.g., an agonist of a protein or peptide). An "antagonist" is any compound or agent, including without limitation small molecules, proteins, peptides, antibodies, nucleic acid binding agents, etc., that blocks or inhibits or reduces the action of an agonist or a naturally occurring substance.

An isolated nucleic acid molecule is a nucleic acid molecule that has been removed from its natural milieu (i.e., that has been subject to human manipulation), its natural milieu being the genome or chromosome in which the nucleic acid molecule is found in nature. As such, "isolated" does not necessarily reflect the extent to which the nucleic acid molecule has been purified, but indicates that the molecule does not include an entire genome or an entire chromosome in which the nucleic acid molecule is found in nature. An isolated nucleic acid molecule can include a gene. An isolated nucleic acid molecule that includes a gene is not a fragment of a chromosome that includes such gene, but rather includes the coding region and regulatory regions associated with the gene, but no additional genes that are naturally found on the same chromosome. An isolated nucleic acid molecule can also include a specified nucleic acid sequence flanked by (i.e., at the 5' and/or the 3' end of the sequence) additional nucleic acids that do not normally flank the specified nucleic acid sequence in nature (i.e., heterologous sequences). Isolated nucleic acid molecule can include DNA, RNA (e.g., mRNA), or derivatives of either DNA or RNA (e.g., cDNA). Although the phrase "nucleic acid molecule" primarily refers to the physical nucleic acid molecule and the phrase "nucleic acid sequence" primarily refers to the sequence of nucleotides on the nucleic acid molecule, the two phrases can be used interchangeably, especially with respect to a nucleic acid molecule, or a nucleic acid sequence, being capable of encoding a protein or domain of a protein. The term "polynucleotide" can also be used interchangeably with the terms "nucleic acid molecule" or "nucleic acid sequence".

A recombinant nucleic acid molecule is a molecule that can include at least one of any nucleic acid sequence encoding any one or more proteins described herein operatively linked to at least one of any transcription control sequence capable of effectively regulating expression of the nucleic acid molecule(s) in the cell to be transfected. Although the phrase "nucleic acid molecule" primarily refers to the physical nucleic acid molecule and the phrase "nucleic acid sequence" primarily refers to the sequence of nucleotides on the nucleic acid molecule, the two phrases can be used interchangeably, especially with respect to a nucleic acid molecule, or a nucleic acid sequence, being capable of encoding a protein. In addition, the phrase "recombinant molecule" primarily refers to a nucleic acid molecule operatively linked to a transcription control sequence, but can be used interchangeably with the phrase "nucleic acid molecule" which is administered to an animal.

A recombinant nucleic acid molecule includes a recombinant vector, which is any nucleic acid sequence, typically a heterologous sequence, which is operatively linked to the isolated nucleic acid molecule encoding a fusion protein of the present invention, which is capable of enabling recombinant production of the fusion protein, and which is capable of delivering the nucleic acid molecule into a host cell according to the present invention. Such a vector can contain nucleic acid sequences that are not naturally found adjacent to the isolated nucleic acid molecules to be inserted into the vector. The vector can be either RNA or DNA, either prokaryotic or eukaryotic, and preferably in the present invention, is a virus or a plasmid. Recombinant vectors can be used in the cloning, sequencing, and/or otherwise manipulating of nucleic acid molecules, and can be used in delivery of such molecules (e.g., as in a DNA composition or a viral vector-based composition). Recombinant vectors are preferably used in the expression of nucleic acid molecules, and can also be referred to as expression vectors. Preferred recombinant vectors are capable of being expressed in a transfected host cell.

In a recombinant molecule of the present invention, nucleic acid molecules are operatively linked to expression vectors containing regulatory sequences such as transcription control sequences, translation control sequences, origins of replication, and other regulatory sequences that are compatible with the host cell and that control the expression of nucleic acid molecules of the present invention. In particular, recombinant molecules of the present invention include nucleic acid molecules that are operatively linked to one or more expression control sequences. The phrase "operatively linked" refers to linking a nucleic acid molecule to an expression control sequence in a manner such that the molecule is expressed when transfected (i.e., transformed, transduced or transfected) into a host cell.

According to the present invention, the term "transfection" is used to refer to any method by which an exogenous nucleic acid molecule (i.e., a recombinant nucleic acid molecule) can be inserted into a cell. The term "transformation" can be used interchangeably with the term "transfection" when such term is used to refer to the introduction of nucleic acid molecules into microbial cells, such as algae, bacteria and yeast. In microbial systems, the term "transformation" is used to describe an inherited change due to the acquisition of exogenous nucleic acids by the microorganism and is essentially synonymous with the term "transfection." Therefore, transfection techniques include, but are not limited to, transformation, chemical treatment of cells, particle bombardment, electroporation, microinjection, lipofection, adsorption, infection and protoplast fusion.

The following experimental results are provided for purposes of illustration and are not intended to limit the scope of the invention.

EXAMPLES

The following Materials and Methods were used in the Examples below.

Mice and Tumor Cell Lines

For in vitro stimulation of lymphocytes, female C57BL/6 (H-2b) mice were obtained from the National Cancer Institute, Frederick Cancer Research and Development Facility (Frederick, Md.). A breeding pair of C57BL/6 mice homozygous for expression of the human CEA gene (CEA-Tg) was generously provided by Dr. John Shively (City of Hope, Duarte, Calif.). Homozygosity for CEA expression was confirmed by PCR analysis of mouse-tail DNA (Greiner et al., *Cancer Res* 2002 Dec. 1; 62(23):6944-51). Six- to 8-week-old female mice were used for all experiments, and were housed in micro-isolator cages under pathogen-free conditions in accordance with AAALAC guidelines. Experimental studies were carried out under approval of the NIH Intramural Animal Care and Use Committee. The target tumor cell line EL-4 (H-2b, thymoma) was obtained from American Type Culture Collection (Manassas, Va.). LL/2 6 murine lung adenocarcinoma tumor cells were the gift of Dr. Chandan Guha (Albert Einstein College of Medicine, New York, N.Y.). LL/2 murine lung carcinoma cells expressing human CEA (LL2-CEA) were generated by retroviral transduction with CEA cDNA, as previously described (Robbins et al., *Cancer Res* 1991 Jul. 15; 51(14):3657-62). Cells were maintained in complete medium (DMEM supplemented with 10% fetal bovine serum, 2 mM glutamine, 100 units/ml penicillin, and 100 µg/ml streptomycin).

Vaccine Constructs

Recombinant vaccinia (rV) and recombinant fowlpox (rF) viruses containing murine B7-1, ICAM-1, and LFA-3 genes as well as the human CEA gene (rV/F-CEA/TRICOM) have been previously described (Hodge et al., *Cancer Res* 1999 Nov. 15; 59(22):5800-7; and Grosenbach et al., *Cancer Res* 2001 Jun. 1; 61(11):4497-505). The murine GM-CSF-expressing rF virus (rFGM-CSF) has been previously described (Kass et al., *Cancer Res* 2001 Jan. 1; 61(1):206-14). A recombinant *Saccharomyces cerevisiae* construct expressing the full-length CEA protein (yeast-CEA) has been previously described (Bernstein et al., *Vaccine* 2008 Jan. 24; 26(4):509-21). Yeast-CEA was produced and heat-killed for these studies as previously described (Haller et al., *Vaccine* 2007 Feb. 9; 25(8):1452-63).

Vaccination Schedules

For serum cytokine analysis, CEA-Tg mice (n=2) were vaccinated with $1\times10^8$ pfu rVCEA/TRICOM or 4 YU/animal (1 YU=$10^7$ yeast particles) of yeast-CEA as previously described (Wansley et al., *Clin Cancer Res* 2008 Jul. 1; 14(13):4316-25). For all other studies, the rV/F-CEA/TRICOM vaccine group, CEA-Tg mice were primed with $1\times10^8$ pfu rV-CEA/TRICOM admixed with $1\times10^7$ pfu rF-GM-CSF on day 0, and boosted every 7 days with $1\times10^8$ pfu rF-CEA/TRICOM admixed with $1\times10^7$ pfu rF-GM-CSF. For the remainder of the Examples and elsewhere according to this invention, this vaccine protocol will be generally designated as "rV/F-CEA/TRICOM". In the yeast-CEA vaccine group, CEA-Tg mice were vaccinated every 7 days with yeast-CEA (4 YU/mouse). Mice receiving the combination of rV/F-CEA/TRICOM and yeast-CEA vaccines were primed with $1\times10^8$ pfu rV-CEA/TRICOM, administered subcutaneously on the dorsal right flank, and with 4 YU/mouse of yeast-CEA, delivered subcutaneously on the inner legs and shoulder blades. The separation of the yeast-CEA dose over multiple sites has previously been described (Wansley, 2008, supra), and has been employed here to separate not only the yeast-CEA vaccine, but also the rV/F-CEA/TRICOM to target multiple draining lymph nodes in the mouse. Mice in the combination group were boosted at 1-week intervals for the remainder of the study with $1\times10^8$ pfu rF-CEA/TRICOM and yeast-CEA (4 YU/mouse).

Cytokine Expression Profiles

For serum cytokine analysis, vaccinated mice (see vaccination schedule above) were bled on days 0, 2, and 4 post-vaccination and serum was isolated. Cytokine expression was analyzed using a Th1/Th2 and proinflammatory cytokine panel by Linco Diagnostic Services (St. Charles, Mo.). To measure cytokines secreted by CD8+ T-cells from mice vaccinated with rV/F-CEA/TRICOM or yeast-CEA (n=5), CD8+ T-cells were bulk cultured and restimulated in the presence of CEA-572-579 peptide (GIQNSVSA, designated CEA-572 and represented herein by SEQ ID NO:11) or CEA-526-533 peptide (EAQNTTYL, designated CEA-526 and represented herein by SEQ ID NO:12) (10 μg/ml) as previously described (Wansley et al., 2008, supra). Cytokine levels were measured using the mouse Inflammatory Cytokine Cytometric Bead Array Kit and the mouse Th1/Th2 Cytokine Cytometric Bead Array kit (BD Biosciences, San Jose, Calif.) according to the manufacturer's instructions.

T-Cell Receptor (TCR) Profiles

RNA was isolated using the RNeasy Mini Kit (Qiagen, Inc., Valencia, Calif.) according to the manufacturer's instructions. RNA was then used in RT-PCR reactions using the Invitrogen SUPERSCRIPT® First-Strand Synthesis System for RT-PCR (Invitrogen, 8 Carlsbad, Calif.) according to the manufacturer's instructions. Vα and Vβ genes were amplified using primers and conditions previously described for 19 Vα and 24 Vβ genes (Pannetier et al., *Proc Natl Acad Sci USA* 1993 May 1; 90(9):4319-23; Arden et al., *Nature* 1985 Aug. 29-Sep. 4; 316(6031):783-7.). PCR products were analyzed using the Agilent 2100 Bioanalyzer and Agilent DNA 1000 Reagent Kit (Agilent Technologies, Santa Clara, Calif.) by on-chip electrophoresis according to the manufacturer's instructions. Agilent 2100 Expert Software (version B.02.0651418 [Patch 01]) was used to identify PCR products by size (bp) and quantity (nmol/L). For each sample, quantities of each gene present were summed, and for each gene, a percent of the total TCR Vα or Vβ repertoire was calculated.

A mouse Vβ TCR screening panel (BD Pharmingen, San Jose, Calif.) consisting of monoclonal antibodies specific for mouse TCR Vβ2, 3, 4, 5.1 and 5.2, 6, 7, 8.1 and 8.2, 8.3, 9, 10, 11, 12, 13, 14, and 17 were used to identify TCR Vβ expression at the protein level by flow cytometry using a FACScan cytometer (Becton Dickinson).

cDNA Oligoarray

CEA-Tg mice were either untreated or vaccinated 3 times at 1-week intervals with rV/F-CEA/TRICOM or yeast-CEA. On day 33, splenocytes were harvested and RNA was isolated. T- and B-cell activation, chemokines and chemokine receptors, and common cytokines cDNA oligoarrays (SABiosciences, Frederick, Md.) were used to investigate changes in gene expression. Genes were considered up-regulated or down-regulated if their normalized intensity ratio was >2 or <0.5 (a 2-fold cutoff), respectively, according to manufacturer's recommendations.

CEA-specific CTL Cell Lines and In Vitro Assays

CEA-526-specific and CEA-572-specific T-cell lines generated from mice vaccinated with rV/F-CEA/TRICOM or yeast-CEA were maintained in culture with CEA-526 or CEA-572 peptide (1 μg/ml) and IL-2 (10 U/ml) with fresh irradiated APCs. To measure the ability of the T-cell lines to lyse $^{111}$In-labeled targets, various ratios of T cells were incubated with labeled targets in triplicate at 37° C. and 5% $CO_2$ in 96-well U-bottom plates. In certain studies, anti-MHC class I blocking antibody (H2D$^b$, BD Pharmingen) was used to distinguish between TCR-mediated and NK-like cytotoxicities. Radioactivity in supernatants was measured using a gammacounter (Corba Autogamma, Packard Instruments, Downers Grove, Ill.). Percentage of tumor lysis was calculated as follows: % tumor lysis=[(experimental cpm−spontaneous cpm)/(maximum cpm−spontaneous cpm)]× 100. To evaluate the avidity of CEA-specific CTL lines, tumor-killing activity was tested as previously described (Hodge et al, 2005, *J Immunol* 174(10):5994-6004). Data were averaged and graphed as Δ% specific lysis. To normalize groups within each experiment, data were also expressed as percentage of maximum lysis versus peptide concentration. Finally, the natural logarithm of the normalized data was plotted against peptide concentration. The avidity of each T-cell population was defined as the negative log of the peptide concentration that resulted in 50% maximal target lysis (Hodge et al., 2005, supra and Derby et al, 2001, *J Immunol* 166(3):1690-1697) and was expressed in nM. The HIV-gag-390-398 peptide (SQVTNPANI, designated HIV-gag peptide and represented herein by SEQ ID NO:13 was used as a negative control in this experiment. MHC class I-peptide tetramers specific for CEA-526 and CEA-572 were obtained from Beckman Coulter (Fullerton, Calif.). Where indicated, CTL activity was converted to lytic units (LU), as described by Wunderlich et al. (1994, "Induction and measurement of cytotoxic T lymphocyte activity." In: Coligan J, Kruisbeek A, Margulies D, Shevach E, Strober W (eds) Current Protocols in Immunology, Wiley, Hoboken, N.J.).

Tumor Therapy Studies

For therapy studies involving LL2-CEA tumors, 6- to 8-week-old female CEA-Tg mice were injected i.v. in the tail with $3\times10^5$ LL2-CEA cells in a volume of 100 μl. Four days post-tumor implantation, mice were primed and then boosted as described above. To enumerate lung metastases, lungs from sacrificed mice were inflated, stained with India ink, and fixed in Fekete's solution (Wexler, *J Natl Cancer Inst* 1966 April; 36(4):641-5).

Statistical Analysis

GraphPad Prism version 4.0a for Macintosh (GraphPad Software, San Diego, Calif.) was used to perform statistical analyses on in vivo data. A 2-tailed, nonparametric Mann-Whitney test was performed for the average number of tumors per mouse at day 45. A log-rank (Mantel-Cox) test was performed for mice bearing >10 pulmonary tumor nodules at day 45 which were deemed to have ≤1 week to live. All values were calculated at a 95% confidence interval and a p value ≤0.05 was considered significant.

Example 1

The following example shows the role of the immunotherapy vector in inducing cytokine and chemokine host innate immune responses that may subsequently influence CEA-specific T-cell responses.

In this experiment, the role of the immunotherapy vector in inducing cytokine and chemokine host innate immune responses that may subsequently influence CEA-specific T-cell responses was investigated. Briefly, CEA-Tg mice (n=2) were vaccinated with rV-CEA/TRICOM or yeast-CEA. Serum was collected at 0, 2, and 4 days, pooled and analyzed for a panel of cytokines using a Th1/Th2 and pro-inflammatory cytokine panel. As shown in FIG. 1, rV-CEA/TRICOM (closed squares) induces a Th1-type cytokine profile, where MIP1α, RANTES, GM-CSF, and IL-12p70 levels are high and IL-5 levels are low (FIGS. 1A, B, C, and E, respectively). In contrast, yeast-CEA vaccination induces a mixed Th1/Th2 cytokine profile with increased levels of IL-6 (FIG. 1D), low levels of MIP1α, RANTES, IL-13, and IL-5 (FIGS. 1A, B, F, and I, respectively). Data are presented as pg/ml of cytokine on each day. These data show that vaccination with rV-CEA/TRICOM vs. yeast-CEA induces expression of different cytokines, indicating that different T-cell populations are induced by each of the vaccine platforms.

Example 2

The following example demonstrates that vaccination with rV/F-CEA/TRICOM vs. yeast-CEA induces distinct TCR repertoires.

This experiment sought to determine whether vaccination with either platform induces CD8+ T-cell populations with distinct TCR repertoires. CEA-Tg mice (n=5 per group) were vaccinated with either rV/F-CEA/TRICOM or yeast-CEA as described in the Materials and Methods section above. Untreated mice served as a negative control (FIGS. 2A and 2D). Spleens from vaccinated mice were harvested 14 days post vaccination and pooled. RT-PCR reactions were performed using 19 Vα-specific and 24 Vβ-specific primers. PCR products were then analyzed and the percentage of the total TCR repertoire was calculated for each gene (FIG. 2; Astericks indicate genes that are uniquely expressed in T-cells from mice vaccinated with one vaccine compared to the other). The TCR Vα profiles of splenocytes from untreated mice and mice vaccinated with rV/F-CEA/TRI-COM or yeast-CEA indicate that each group has a distinct TCR Vα expression profile (FIGS. 2A to C). The expression of 12 of the 19 Vα genes was similar between T-cells induced by both vaccines, while 7 Vα genes are unique to T-cell populations from one vaccine compared to the other (FIGS. 2B and C). Comparison of the Vβ repertoires from these same animals indicated that, with a few exceptions, the Vβ profiles also differ among the two groups of mice (FIGS. 2D to E). The expression of 14 of the 24 Vβ genes was similar between T-cells induced by both vaccines, yet the vaccines induce unique Vβ genes as well. As shown in FIGS. 2E and F, 10 Vβ genes were uniquely expressed by T-cells from either rV/F-CEA/TRICOM or yeast-CEA-vaccinated CEA-Tg mice (Vβ1, Vβ4, Vβ5.1, Vβ5.2, Vβ5.3, Vβ8.1, Vβ8.3, Vβ9, Vβ10, and Vβ20). These data indicate that the Vα and Vβ TCR repertoires of T-cells from untreated mice and mice vaccinated with rV/F-CEA/TRI-COM or yeast-CEA have both shared and unique patterns of TCR gene expression. It is unknown, however, if these differences are due to different processing and presentation of the CEA antigen by the different vector-infected cells, or to the vectors themselves. The TCR repertoires of T-cell lines specific for two different CEA epitopes created from CEA-Tg mice vaccinated with the two vector platforms are described in the examples below.

Example 3

The following example shows that vaccination with rV/F-CEA/TRICOM or yeast-CEA induces both shared and unique gene expression in response to vector and antigen.

To investigate the effects of both vector and antigen on the gene expression of splenocytes, cDNA oligoarrays were used to further characterize the T-cell populations induced by vaccination with rV/F-CEA/TRICOM or yeast-CEA. The expression of 252 genes involved in T- and B-cell activation, chemokines, chemokine receptors, and cytokines by splenocytes of CEA-Tg mice vaccinated with rV/FCEA/TRI-COM or yeast-CEA was investigated. Table 1 shows that for each array, both rV/FCEA/TRICOM and yeast-CEA induce changes in expression of the same genes, including up-regulation of 26 genes by at least 2-fold, the majority of which are involved in cytokine signaling. In addition, both vaccines up-regulated Ltb4r2, a leukotriene receptor involved in chemotaxis of immune cells, genes involved in T-cell proliferation, such as secreted phosphoprotein-1 (Spp1, or osteopontin), and the tumor suppressor Inha. At the same time, each vaccine platform induces unique changes in expression of several genes (Table 1, bold). Yeast-CEA down-regulates genes involved in chemotaxis of immune cells such as Ccl12, Cxcl9, Ccr9, while rV/F-CEA/TRICOM does not alter the expression of any of the these genes. The results from this experiment indicate that the two vaccine platforms induce changes in gene expression that are both shared and unique.

TABLE 1

| Vaccination | Genes Involved in T-cell and B-cell Activation | Chemokines and Chemokine Receptors | Cytokines |
|---|---|---|---|
| rV/F-CEA/TRICOM/No treatment | | | |
| Genes up-regulated >2-fold | H60, Igbp1b, Il11, Il4 | Inha (3.03), Ltb4r2, Bmp10, Bmp5 | Il17c, Il17f, Inhba Fgf10, Gdf2, Gdf5, Gdf8, Ifna2, Ifna4, Ifnbl, Il13, Il17b, Il25, Il19, Ilf10, Ilf5, Ilf6, Ilf8, Il20, Il3, Il9 |
| Genes down-regulated >2-fold | Ms4al, Sppl (4.00) | | Il1rn (4.29) |
| Yeast-CEA/No treatment | | | |
| Genes up-regulated >2-fold | Rag1 (3.48) H60 (3.25), Igbp1b (3.25), Il11 (3.25), Il4 | Bdnf, Ccl20, Cmtm2a, Cmtm5, Cxcl15, Gdf5, Ccl17 Inha (4.92), Ltb4r2 (4.92), Bmp10, Bmp5 | GdX Fgf10, Gdf2, Gdf5, Gdf8, Ifna2, Ifna4, Ifnbl, Il13, Il17b, Il25, Il19, Ilf10, Ilf5, Ilf6, Ilf8, Il20, Il3, Il9 |
| Genes down-regulated >2-fold | Tnfrsf13c (6.06) Ms4al (3.25), Spp1 | Ccl12 (3.03), Cc18 (3.73) Ccr9, Ccrl2, Csf2, Cx3crl, Cxcl10, Cxcl13, Hif1a, Inhbb, Lif (3.48), Gusb, Cxcl9 (4.92) | Gdf3 (4.0), Il10, Csf-2, Fasl, Tnf, Tnfrsf11b, Tnfsf15 |

Genes in bold are up-regulated/down-regulated specifically by splenocytes from mice vaccinated with either rV/F-CEA/TRICOM or yeast-CEA, but not by both.
Fold changes >3-fold are noted in parentheses

Example 4

The following example demonstrates that rV/F-CEA/TRICOM and yeast-CEA induce functionally distinct T-cell populations.

To determine the antigen-specific response of T-cell populations induced by the vaccines, the cytokines produced by T-cells from vaccinated animals after in vitro stimulation with either of two discrete CEA epitopes (CEA-572 and CEA-526) were investigated. FIG. 3A illustrates CEA protein showing the discrete, non-overlapping CEA-526 and CEA-572 epitopes on the A3 loop of domain III.

Referring to FIG. 3, CEA-Tg mice (n=5) were primed with rV-CEA/TRICOM (solid bars) on day 0 and boosted on days 7 and 14 with rFCEA/TRICOM; CEA-Tg mice (n=5) were primed on day 0 and boosted on days 7 and 14 with yeast-CEA (open bars). On day 33, mice were sacrificed and spleens pooled and put into bulk cultures with either (FIG. 3B) CEA-526 or (FIG. 3C) CEA-572 peptide for 7 days. IL-2, IL-10, TNF-α, IFN-γ, IL-5 and IL-4 were measured by cytokine bead array (pg/ml/L×$10^6$ cells) after lymphocytes were restimulated for 24 hours with CEA-specific peptide or VSVN peptide control. All data have been normalized to the VSVN peptide control.

It was observed that the two different CEA epitopes induce different levels of cytokine production from T cells from vaccinated animals. Higher levels of TNF-α are secreted in response to CEA-526 after rV/F-CEA/TRICOM vaccination compared to yeast-CEA (FIG. 3B, closed bar), yet yeast-CEA vaccination produces significantly higher levels of TNF-α when T cells are stimulated with CEA-572 peptide (FIG. 3C, open bar). Also, T cells from yeast-CEA vaccination induce higher levels of IL-2 compared to T cells from rV/F-CEA/TRICOM vaccination, when stimulated with the CEA-526 and CEA-572 peptides (FIGS. 3B and 3C, open bars). Similarly, after vaccination with rV/F-CEA/TRICOM, T cells induce higher levels of IFN-γ compared to yeast-CEA vaccination in response to the CEA-526 and CEA-572 peptides (FIGS. 3B and 3C, closed bars).

The data also show that T-cells from vaccinated animals secrete different levels of various cytokines in response to a single CEA epitope. T-cells from mice vaccinated with yeast-CEA secrete IL-4, IL-10, TNF-α, IFN-γ, IL-5, and IL-2 in response to the CEA-572 epitope (FIG. 3C, open bars). On the other hand, T-cells from mice vaccinated with rV/F-CEA/TRICOM secrete significantly higher levels of IFN-γ compared to yeast-CEA in response to the CEA-572 peptide and lower levels of IL-10 and TNF-α in response to the CEA-572 epitope (FIG. 3C, closed bars). These results indicate that the T-cell populations induced by vaccination with rV/F-CEA/TRICOM or yeast-CEA are antigen-specific and functionally distinct.

Example 5

The following example demonstrates that T-cell lines developed from mice vaccinated with rV/F-CEA/TRICOM versus yeast-CEA have 14 distinct TCR repertoires and functional avidity.

To further explore potential differences in the functionality of T cells from mice vaccinated with either rV/F-CEA/TRICOM or yeast-CEA, T-cell lines specific for either CEA-526 or CEA-572 peptide were created from vaccinated CEA-Tg mice as described in the Materials and Methods. Briefly, CEA-Tg mice (n=5 per group) vaccinated with rV/F-CEA/TRICOM or yeast-CEA as described above. Two weeks after the final vaccination, spleens were harvested and pooled, and splenocytes were bulk cultured with CEA-526 or CEA-572 peptide for 7 days. Lymphocytes were restimulated with fresh peptide, IL-2, and irradiated APCs every 7 days and kept in culture for in vitro experiments. TCR profile analysis was conducted after 18 stimulation cycles.

Figure 4D:
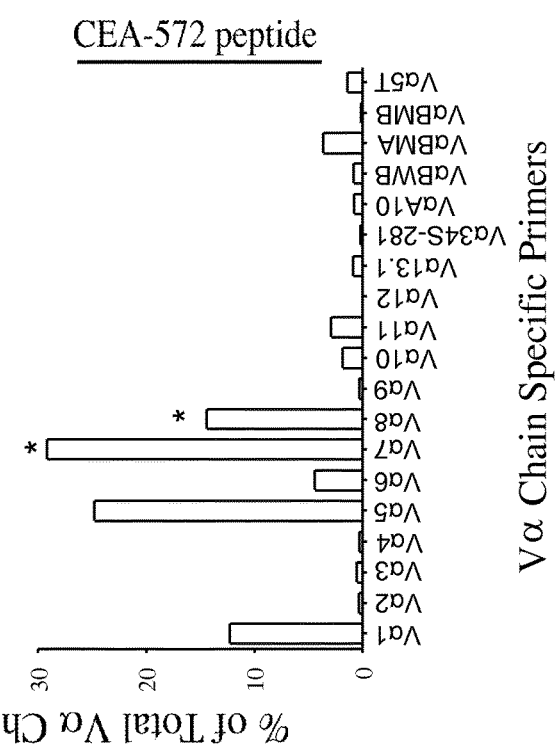

Vα TCR profiles from the 4 cell lines indicate that the T-cell populations have shared and distinct Vα TCR repertoires. Referring to FIG. 4, Vα TCR repertoires of rV/F-CEA/TRICOM T-cell lines (black bars) maintained in the presence of (FIG. 4A) CEA-526 peptide and (FIG. 4B) CEA-572 peptide are shown. FIG. 4 also shows Vα TCR repertoires of yeast-CEA T cell lines (white bars) maintained in the presence of (FIG. 4C) CEA-526 peptide and (FIG. 4D) CEA-572 peptide. Results are expressed as percentage of total Vα chain TCR repertoire. Astericks indicate 31 genes that are uniquely expressed in T cells from mice vaccinated with one vaccine compared to the other.

In T-cells from mice vaccinated stimulated with the CEA-526 epitope, the T-cells have shared expression of 16 of the 19 Vα genes and unique expression of 3 Vα genes (FIGS. 4A and C). In T-cells from mice vaccinated stimulated with the CEA-572 epitope, the T cells have shared expression of 15 of the 19 Vα genes and unique expression of 4 Vα genes (FIGS. 4B and D). Similar results were seen when Vβ TCR profiles were analyzed (data not shown). In addition, expression of selected Vβ TCR genes of the T-cell lines were confirmed by flow cytometry using commercially available monoclonal antibodies (data not shown). These data provide further evidence that the T-cell populations from mice vaccinated with either rV/F-CEA/TRICOM or yeast-CEA are both vector- and antigen-specific.

To characterize the functional differences between T-cells from either vector, the CEA-specific cytolytic activity of T-cells generated from rV/FCEA/TRICOM was compared to that generated from yeast-CEA vaccination. The purity of the T-cell line cultures was confirmed via cell surface staining with monoclonal antibodies to identify CD8, CD4, and NK cells followed by flow cytometry (data not shown). In addition, tetramer staining using MHC class I-peptide tetramers specific for CEA-526 or CEA-572 confirmed peptide specificity for the T-cell lines (data not shown).

Briefly, T cell lines generated from rV/F-CEA/TRICOM vaccination and specific for (FIG. 5A) CEA-526 peptide and (FIG. 5C) CEA-572 peptide were incubated with peptide-pulsed $^{111}$In-labeled EL-4 cell targets at the indicated ratios for 4 h. T-cell lines generated from yeast-CEA vaccination and specific for (FIG. 5B) CEA-526 peptide and (FIG. 5D) CEA-572 peptide were also incubated with $^{111}$In-labeled EL-4 cell targets at the indicated ratios for 4 h. Referring to FIG. 5, $^{111}$In-labeled EL-4 cells pulsed with CEA-572 and CEA-526 peptides are represented by solid squares connected by a solid line, and $^{111}$In-labeled EL-4 cells pulsed with VSVNP (negative control) are represented by open circles connected by a dotted line. To determine T-cell avidity, (FIG. 5B, inset) CEA-526-specific T-cell lines from rV/F-CEA/TRICOM (closed squares) and yeast-CEA (open circles) were incubated with $^{111}$In-labeled EL-4 cells in the presence of various concentrations of CEA-526 (or HIV-gag control) peptide ranging from 1 μM to 0 μM for 4 h. T-cell lines specific for CEA-572 epitope, generated from mice vaccinated with rV/F-CEA/TRICOM (FIG. 5E) or yeast-CEA (FIG. 5F), were also used in cytolytic T-cell assays with $^{111}$In-labeled LL2-CEA and normalized to LL2 (negative control) tumor targets at various ratios. Bars indicate standard error from triplicate wells.

FIGS. 5A and 5B show that a CEA-526 peptide-specific T-cell line generated from rV/F-CEA/TRICOM has higher lytic activity compared to a T-cell line generated from yeast-CEA vaccination. T-cell lines specific for the CEA-572 epitope both demonstrated similar levels of cytolytic activity (FIGS. 5C and 5D). FIG. 5B inset shows that the CEA-526-specific T-cell line generated from rV/F-CEA/TRICOM vaccination had a 23.3-fold higher avidity than the CEA-526-specific T-cell line generated from yeast-CEA vaccination.

The CEA-572-specific T-cell lines were also used in a CTL assay targeting $^{111}$In-labeled LL2-CEA cells. CEA-572-specific T cells from mice vaccinated with either rV/F-CEA/TRICOM or yeast-CEA were cultured for 20 weeks prior to this assay. Both T-cell lines lyse LL2-CEA targets and lysis decreases as the ratio of T-cells to effector cells (LL2-CEA targets) decreases (FIGS. 5E and 5F). These results indicate that both T-cell lines are capable of lysing CEA-expressing cells, although the T-cell line from mice vaccinated with yeast-CEA (FIG. 5F) had a higher level of activity compared to the T-cell line from mice vaccinated with rV/FCEA/TRICOM (FIG. 5E) when LL2-CEA cell lysis was normalized to that of LL2 cells.

To confirm that the cell lysis observed in FIGS. 5E and 5F was TCR-mediated and not due to NK cell activity, CTL experiments with blocking monoclonal antibodies specific for MHC class I molecules were performed with LL2-CEA tumor targets and normalized to LL2 target cells as a control, and showed that the presence of MHC class I blocking antibody abrogated cell lysis. The lack of NK cell-mediated lysis was further confirmed in a CTL using YAK1 targets, which found that the presence of MHC class blocking antibody abrogated YAK1 cell lysis by the various T-cell lines. Together, these results indicate that the lytic activity of T-cell lines created from different vectors targeting the same CEA-epitope is TCR-mediated and levels of cell lysis are similar when targeting peptide-pulsed target cells, although their ability to lyse CEA-expressing tumor targets differs. Additionally, the avidity of rV/F-CEA/TRICOM-induced T-cell lines may be higher than that of T-cell lines created from yeast-CEA vaccination. These results further characterize the T-cell populations from mice vaccinated with rV-CEA/TRICOM or yeast-CEA as platform-specific.

Example 6

The following example demonstrates that combining rV/F-CEA/TRICOM and yeast-CEA is an efficacious antitumor therapy in a murine orthotopic pulmonary metastasis model.

Studies were conducted to determine if concurrent administration of the two vaccines would generate antitumor activity superior to vaccination with either vaccine platform alone. Briefly, CEA-Tg mice were injected i.v. with LL2-CEA tumor cells. On day 4, mice were primed with rV/F-CEA/TRICOM (n=10), yeast-CEA (n=14), or rV/F-CEA/TRICOM and yeast-CEA (n=10); a control group (n=17) received no treatment. Mice were boosted every 7 days for the duration of the experiment. The rV/F-CEA/TRICOM group was boosted with rV/F-CEA/TRICOM. The yeast-CEA group was boosted with yeast-CEA only. The combination group was boosted with rV/F-CEA/TRICOM and yeast-CEA. For these studies, rV/F-CEA/TRICOM was injected s.c. on the dorsal right flank while 1 YU yeast-CEA was delivered s.c. to each inner leg and shoulder blade to target multiple draining lymph nodes. On day 45, mice were sacrificed and lungs were harvested, stained, and fixed. The data shown in FIG. 6 represent the number of lung metastases per mouse from two separate experiments (indicated by open vs. closed symbols). The bar indicates the average number of metastases per mouse p=0.015 comparing untreated mice with the rV/F-CEA/TRICOM and yeast-CEA combination group.

Untreated mice had an average of 10.84 tumors per mouse (+2.41). Mice vaccinated with rV/FCEA/TRICOM had an average of 7.50 metastases per mouse (+2.02), and mice vaccinated with yeast-CEA had an average of 9.71 metastases per mouse (+1.22). However, mice vaccinated with the combination of rV/F-CEA/TRICOM and yeast-CEA had 2.80 metastases per mouse (+0.77); this combination group was the only group with a significantly lower number of metastases compared to the untreated control (p=0.015). Also, the maximum number of metastases per mouse for the untreated, rV/F-CEA/TRICOM, and yeast-CEA groups was 36, 24, and 18, respectively, while the maximum number of metastases in the combination group was 7. Moreover, the log-rank test (mice bearing >9 pulmonary tumor nodules on day 45; assumed to have <1 week to live) showed statistical significance between untreated mice and the mice that received the combination of rV/F-CEA/TRICOM and yeast-CEA (p=0.0027). Also, there was statistical significance between mice treated with rV/F-CEA/TRICOM alone versus concurrent vaccination with rV/F-CEA/TRICOM and yeast-CEA (p=0.0293). In addition, there was statistical significance between mice treated with yeast-CEA alone versus concurrent vaccination with rV/F-CEA/TRICOM and yeast-CEA (p=0.0017). These results, taken together, indicate that concurrent administration of rV/F-CEA/TRICOM and yeast-CEA vaccines can increase antitumor efficacy.

As discussed above, published reports comparing vaccine platforms have historically concluded that one is more effective than the other at stimulating the immune system, and have thus recommended further development of the more effective platform for clinical studies (Riezebos-Brilman et al., *Gene Ther* 2007 December; 14(24):1695-704; and Casimiro et al., *J Virol* 2003 June; 77(11):6305-13). The results provided herein have demonstrated that the T-cell population elicited by each platform displayed unique and shared phenotypic and functional responses to different CEA epitopes. The results presented herein show for the first time that (a) 2 vaccine platforms targeting the same antigen induce distinct T-cell populations, (b) induction of these T-cell populations is both vector- and antigen-specific, and (c) the vaccines can be used concurrently in an antitumor model to improve antitumor efficacy.

While various embodiments of the present invention have been described in detail, it is apparent that modifications and adaptations of those embodiments will occur to those skilled in the art. It is to be expressly understood, however, that such modifications and adaptations are within the scope of the present invention, as set forth in the following claims.

What is claimed is:

1. A method to reduce tumor burden or inhibit tumor growth and/or to induce a therapeutic immune response against carcinoembryonic antigen (CEA) in an individual, comprising administering two immunotherapy compositions within one dosing of the individual in order to prime the immune system with each of the compositions, the two immunotherapy compositions comprising:
   a) a first immunotherapy composition comprising a recombinant vaccinia virus comprising nucleic acid sequences encoding costimulatory molecules B7-1, ICAM-1 and LFA-3, and nucleic acid sequences encoding CEA or an immunogenic domain thereof; and
   b) a second immunotherapy composition comprising a whole inactivated yeast that has recombinantly expressed, prior to administration, CEA or an immunogenic domain thereof;
   wherein the administration of the first and second immunotherapy compositions reduces tumor burden or inhibits tumor growth in the individual and/or induces a therapeutic immune response against CEA in the individual.

2. The method of claim 1, wherein the first and second immunotherapy compositions are administered to different sites in the individual.

3. The method of claim 1, further comprising boosting the individual with one or both of the immunotherapy compositions.

4. The method of claim 1, further comprising boosting the individual with a third immunotherapy composition comprising a recombinant virus comprising the virus genome or portions thereof that is different from the first immunotherapy composition.

5. The method of claim 1, wherein the CEA comprises a CAP1-6D epitope.

6. A kit comprising the following immunotherapy compositions:
   a. a first immunotherapy composition comprising a recombinant vaccinia virus comprising nucleic acid sequences encoding costimulatory molecules B7-1, ICAM-1 and LFA-3 and nucleic acid sequences encoding human carcinoembryonic antigen (CEA) or an immunogenic domain thereof; and a second immunotherapy composition comprising whole inactivated yeast that has recombinantly expressed human CEA or an immunogenic domain thereof.

7. The kit of claim 6, further comprising a third immunotherapy composition comprising a recombinant fowlpox virus comprising nucleic acid sequences encoding B7-1, ICAM-1 and LFA-3 or biologically active portions thereof, and a nucleic acid sequence encoding the at least one cancer antigen or immunogenic domain thereof.

8. The kit of claim 7, wherein the first, third, or both the first and third, immunotherapy composition further comprises granulocyte-macrophage colony-stimulating factor (GM-CSF).

9. The kit of claim 8, wherein the GM-CSF is provided by a recombinant fowlpox virus encoding GM-CSF.

10. The kit of claim 6, wherein the vaccinia virus in the first immunotherapy composition is from modified vaccinia Ankara (MVA) or vaccinia-Wyeth strain.

11. The kit of claim 6, wherein the whole inactivated yeast in the second immunotherapy composition is a whole, heat-killed yeast.

12. The kit of claim 6, wherein the whole inactivated yeast in the second immunotherapy composition is from *Saccharomyces*.

13. The kit of claim 6, wherein the cancer antigen is carcinoembryonic antigen (CEA).

14. The kit of claim 13, wherein the CEA comprises a CAP1-6D epitope.

15. The method of claim 1, further comprising, at least one week after the administration of the first and second immunotherapy compositions, administering to the individual:
   a. a third immunotherapy composition comprising a recombinant fowlpox virus comprising nucleic acid sequences encoding B7-1, ICAM-1 and LFA-3 or biologically active portions thereof, and a nucleic acid sequence encoding the at least one cancer antigen or immunogenic domain thereof; and
   b. the second immunotherapy composition comprising the whole inactivated yeast that has recombinantly expressed, prior to administration, the at least one cancer antigen or immunogenic domain thereof;
   wherein the second and third immunotherapy compositions are both administered to the individual within one dosing period.

16. The method of claim 15, wherein the first, third, or both the first and third, immunotherapy composition further comprises granulocyte-macrophage colony-stimulating factor (GM-CSF).

17. The method of claim 16, wherein the GM-CSF is provided by a recombinant fowlpox virus encoding GM-CSF.

18. The method of claim 1, wherein the individual is further treated with chemotherapy and/or with radiation therapy.

19. The method of claim 1, wherein the vaccinia virus in the first immunotherapy composition is from modified vaccinia Ankara (MVA) or vaccinia-Wyeth strain.

20. The method of claim 1, wherein the whole inactivated yeast in the second immunotherapy composition is a whole, heat-killed yeast.

21. The method of claim 1, wherein the whole inactivated yeast in the second immunotherapy composition is from *Saccharomyces*.

22. The method of claim 1, wherein the CEA is human CEA.

23. The method of claim 22, wherein the human CEA is full-length human CEA.

24. The method of claim 3, wherein boosting the individual is with both immunotherapy compositions.

25. A method to reduce tumor burden or inhibit tumor growth and/or to induce a therapeutic immune response against human carcinoembryonic antigen (CEA) in an individual, comprising:
  a. administering two immunotherapy compositions within one dosing of the individual in order to prime the immune system with each of the compositions, the two immunotherapy compositions comprising:
    (i) a first immunotherapy composition comprising rV/F-CEA/TRICOM; and
    (ii) a second immunotherapy composition comprising a whole inactivated yeast that has recombinantly expressed, prior to administration, human CEA; and
  b. administering boosters of the two immunotherapy compositions;
  wherein the administration of the first and second immunotherapy compositions reduces tumor burden or inhibits tumor growth in the individual and/or induces a therapeutic immune response against one or more cancer antigens in the individual.

* * * * *

SEQUENCE LISTING

<160> NUMBER OF SEQ ID NOS: 15

<210> SEQ ID NO 1
<211> LENGTH: 2124
<212> TYPE: DNA
<213> ORGANISM: Artificial
<220> FEATURE:
<223> OTHER INFORMATION: synthetic construct
<220> FEATURE:
<221> NAME/KEY: CDS
<222> LOCATION: (7)..(2109)

<400> SEQUENCE: 1

```
gaattc atg gag tct ccc tcg gcc cct ccc cac aga tgg tgc atc ccc        48
       Met Glu Ser Pro Ser Ala Pro Pro His Arg Trp Cys Ile Pro
       1               5                   10 tgg cag agg ctc ctg ctc aca gcc tca ctt cta acc ttc tgg aac ccg        96
Trp Gln Arg Leu Leu Leu Thr Ala Ser Leu Leu Thr Phe Trp Asn Pro
15                  20                  25                  30 ccc acc act gcc aag ctc act att gaa tcc acg ccg ttc aat gtc gca       144
Pro Thr Thr Ala Lys Leu Thr Ile Glu Ser Thr Pro Phe Asn Val Ala
                35                  40                  45 gag ggg aag gag gtg ctt cta ctt gtc cac aat ctg ccc cag cat ctt       192
Glu Gly Lys Glu Val Leu Leu Leu Val His Asn Leu Pro Gln His Leu
            50                  55                  60 ttt ggc tac agc tgg tac aaa ggt gaa aga gtg gat ggc aac cgt caa       240
Phe Gly Tyr Ser Trp Tyr Lys Gly Glu Arg Val Asp Gly Asn Arg Gln
65                  70                  75 att ata gga tat gta ata gga act caa caa gct acc cca ggg ccc gca       288
Ile Ile Gly Tyr Val Ile Gly Thr Gln Gln Ala Thr Pro Gly Pro Ala
            80                  85                  90 tac agt ggt cga gag ata ata tac ccc aat gca tcc ctg ctg atc cag       336
Tyr Ser Gly Arg Glu Ile Ile Tyr Pro Asn Ala Ser Leu Leu Ile Gln
95                  100                 105                 110 aac atc atc cag aat gac aca gga ttc tac acc cta cac gtc ata aag       384
Asn Ile Ile Gln Asn Asp Thr Gly Phe Tyr Thr Leu His Val Ile Lys
                115                 120                 125 tca gat ctt gtg aat gaa gaa gca act ggc cag ttc cgg gta tac ccg       432
Ser Asp Leu Val Asn Glu Glu Ala Thr Gly Gln Phe Arg Val Tyr Pro
            130                 135                 140 gag ctg ccc aag ccc tcc atc tcc agc aac aac tcc aaa ccc gtg gag       480
Glu Leu Pro Lys Pro Ser Ile Ser Ser Asn Asn Ser Lys Pro Val Glu
145                 150                 155 gac aag gat gct gtg gcc ttc acc tgt gaa cct gag act cag gac gca       528
Asp Lys Asp Ala Val Ala Phe Thr Cys Glu Pro Glu Thr Gln Asp Ala
            160                 165                 170 acc tac ctg tgg tgg gta aac aat cag agc ctc ccg gtc agt ccc agg       576
Thr Tyr Leu Trp Trp Val Asn Asn Gln Ser Leu Pro Val Ser Pro Arg
175                 180                 185                 190 ctg cag ctg tcc aat ggc aac agg acc ctc act cta ttc aat gtc aca       624
Leu Gln Leu Ser Asn Gly Asn Arg Thr Leu Thr Leu Phe Asn Val Thr
                195                 200                 205 aga aat gac aca gca agc tac aaa tgt gaa acc cag aac cca gtg agt       672
Arg Asn Asp Thr Ala Ser Tyr Lys Cys Glu Thr Gln Asn Pro Val Ser
            210                 215                 220 gcc agg cgc agt gat tca gtc atc ctg aat gtc ctc tat ggc ccg gat       720
Ala Arg Arg Ser Asp Ser Val Ile Leu Asn Val Leu Tyr Gly Pro Asp
            225                 230                 235 gcc ccc acc att tcc cct cta aac aca tct tac aga tca ggg gaa aat       768
Ala Pro Thr Ile Ser Pro Leu Asn Thr Ser Tyr Arg Ser Gly Glu Asn
240                 245                 250
```

```
ctg aac ctc tcc tgc cac gca gcc tct aac cca cct gca cag tac tct         816
Leu Asn Leu Ser Cys His Ala Ala Ser Asn Pro Pro Ala Gln Tyr Ser
255                 260                 265                 270 tgg ttt gtc aat ggg act ttc cag caa tcc acc caa gag ctc ttt atc         864
Trp Phe Val Asn Gly Thr Phe Gln Gln Ser Thr Gln Glu Leu Phe Ile
            275                 280                 285 ccc aac atc act gtg aat aat agt gga tcc tat acg tgc caa gcc cat         912
Pro Asn Ile Thr Val Asn Asn Ser Gly Ser Tyr Thr Cys Gln Ala His
                290                 295                 300 aac tca gac act ggc ctc aat agg acc aca gtc acg acg atc aca gtc         960
Asn Ser Asp Thr Gly Leu Asn Arg Thr Thr Val Thr Thr Ile Thr Val
                    305                 310                 315 tat gag cca ccc aaa ccc ttc atc acc agc aac aac tcc aac ccc gtg        1008
Tyr Glu Pro Pro Lys Pro Phe Ile Thr Ser Asn Asn Ser Asn Pro Val
320                 325                 330 gag gat gag gat gct gta gcc tta acc tgt gaa cct gag att cag aac        1056
Glu Asp Glu Asp Ala Val Ala Leu Thr Cys Glu Pro Glu Ile Gln Asn
335                 340                 345                 350 aca acc tac ctg tgg tgg gta aat aat cag agc ctc ccg gtc agt ccc        1104
Thr Thr Tyr Leu Trp Trp Val Asn Asn Gln Ser Leu Pro Val Ser Pro
                355                 360                 365 agg ctg cag ctg tcc aat gac aac agg acc ctc act cta ctc agt gtc        1152
Arg Leu Gln Leu Ser Asn Asp Asn Arg Thr Leu Thr Leu Leu Ser Val
            370                 375                 380 aca agg aat gat gta gga ccc tat gag tgt gga atc cag aac gaa tta        1200
Thr Arg Asn Asp Val Gly Pro Tyr Glu Cys Gly Ile Gln Asn Glu Leu
        385                 390                 395 agt gtt gac cac agc gac cca gtc atc ctg aat gtc ctc tat ggc cca        1248
Ser Val Asp His Ser Asp Pro Val Ile Leu Asn Val Leu Tyr Gly Pro
400                 405                 410 gac gac ccc acc att tcc ccc tca tac acc tat tac cgt cca ggg gtg        1296
Asp Asp Pro Thr Ile Ser Pro Ser Tyr Thr Tyr Tyr Arg Pro Gly Val
415                 420                 425                 430 aac ctc agc ctc tcc tgc cat gca gcc tct aac cca cct gca cag tat        1344
Asn Leu Ser Leu Ser Cys His Ala Ala Ser Asn Pro Pro Ala Gln Tyr
                435                 440                 445 tct tgg ctg att gat ggg aac atc cag caa cac aca caa gag ctc ttt        1392
Ser Trp Leu Ile Asp Gly Asn Ile Gln Gln His Thr Gln Glu Leu Phe
            450                 455                 460 atc tcc aac atc act gag aag aac agc gga ctc tat acc tgc cag gcc        1440
Ile Ser Asn Ile Thr Glu Lys Asn Ser Gly Leu Tyr Thr Cys Gln Ala
        465                 470                 475 aat aac tca gcc agt ggc cac agc agg act aca gtc aag aca atc aca        1488
Asn Asn Ser Ala Ser Gly His Ser Arg Thr Thr Val Lys Thr Ile Thr
480                 485                 490 gtc tct gcg gag ctg ccc aag ccc tcc atc tcc agc aac aac tcc aaa        1536
Val Ser Ala Glu Leu Pro Lys Pro Ser Ile Ser Ser Asn Asn Ser Lys
495                 500                 505                 510 ccc gtg gag gac aag gat gct gtg gcc ttc acc tgt gaa cct gag gct        1584
Pro Val Glu Asp Lys Asp Ala Val Ala Phe Thr Cys Glu Pro Glu Ala
                515                 520                 525 cag aac aca acc tac ctg tgg tgg gta aat ggt cag agc ctc cca gtc        1632
Gln Asn Thr Thr Tyr Leu Trp Trp Val Asn Gly Gln Ser Leu Pro Val
            530                 535                 540 agt ccc agg ctg cag ctg tcc aat ggc aac agg acc ctc act cta ttc        1680
Ser Pro Arg Leu Gln Leu Ser Asn Gly Asn Arg Thr Leu Thr Leu Phe
        545                 550                 555 aat gtc aca aga aat gac gca aga gcc tat gta tgt gga atc cag aac        1728
Asn Val Thr Arg Asn Asp Ala Arg Ala Tyr Val Cys Gly Ile Gln Asn
560                 565                 570
```

-continued

```
tca gtg agt gca aac cgc agt gac cca gtc acc ctg gat gtc ctc tat    1776
Ser Val Ser Ala Asn Arg Ser Asp Pro Val Thr Leu Asp Val Leu Tyr
575                 580                 585                 590 ggg ccg gac acc ccc atc att tcc ccc cca gac tcg tct tac ctt tcg    1824
Gly Pro Asp Thr Pro Ile Ile Ser Pro Pro Asp Ser Ser Tyr Leu Ser
                595                 600                 605 gga gcg gac ctc aac ctc tcc tgc cac tcg gcc tct aac cca tcc ccg    1872
Gly Ala Asp Leu Asn Leu Ser Cys His Ser Ala Ser Asn Pro Ser Pro
            610                 615                 620 cag tat tct tgg cgt atc aat ggg ata ccg cag caa cac aca caa gtt    1920
Gln Tyr Ser Trp Arg Ile Asn Gly Ile Pro Gln Gln His Thr Gln Val
        625                 630                 635 ctc ttt atc gcc aaa atc acg cca aat aat aac ggg acc tat gcc tgt    1968
Leu Phe Ile Ala Lys Ile Thr Pro Asn Asn Asn Gly Thr Tyr Ala Cys
640                 645                 650 ttt gtc tct aac ttg gct act ggc cgc aat aat tcc ata gtc aag agc    2016
Phe Val Ser Asn Leu Ala Thr Gly Arg Asn Asn Ser Ile Val Lys Ser
655                 660                 665                 670 atc aca gtc tct gca tct gga act tct cct ggt ctc tca gct ggg gcc    2064
Ile Thr Val Ser Ala Ser Gly Thr Ser Pro Gly Leu Ser Ala Gly Ala
                675                 680                 685 act gtc ggc atc atg att gga gtg ctg gtt ggg gtt gct ctg ata        2109
Thr Val Gly Ile Met Ile Gly Val Leu Val Gly Val Ala Leu Ile
                690                 695                 700 tagtttagcg gccgc                                                   2124
```

<210> SEQ ID NO 2
<211> LENGTH: 701
<212> TYPE: PRT
<213> ORGANISM: Artificial
<220> FEATURE:
<223> OTHER INFORMATION: Synthetic Construct

<400> SEQUENCE: 2

Met Glu Ser Pro Ser Ala Pro Pro His Arg Trp Cys Ile Pro Trp Gln
1               5                   10                  15

Arg Leu Leu Leu Thr Ala Ser Leu Leu Thr Phe Trp Asn Pro Pro Thr
            20                  25                  30

Thr Ala Lys Leu Thr Ile Glu Ser Thr Pro Phe Asn Val Ala Glu Gly
        35                  40                  45

Lys Glu Val Leu Leu Leu Val His Asn Leu Pro Gln His Leu Phe Gly
    50                  55                  60

Tyr Ser Trp Tyr Lys Gly Glu Arg Val Asp Gly Asn Arg Gln Ile Ile
65                  70                  75                  80

Gly Tyr Val Ile Gly Thr Gln Gln Ala Thr Pro Gly Pro Ala Tyr Ser
                85                  90                  95

Gly Arg Glu Ile Ile Tyr Pro Asn Ala Ser Leu Leu Ile Gln Asn Ile
            100                 105                 110

Ile Gln Asn Asp Thr Gly Phe Tyr Thr Leu His Val Ile Lys Ser Asp
        115                 120                 125

Leu Val Asn Glu Glu Ala Thr Gly Gln Phe Arg Val Tyr Pro Glu Leu
    130                 135                 140

Pro Lys Pro Ser Ile Ser Ser Asn Asn Ser Lys Pro Val Glu Asp Lys
145                 150                 155                 160

Asp Ala Val Ala Phe Thr Cys Glu Pro Glu Thr Gln Asp Ala Thr Tyr
                165                 170                 175

Leu Trp Trp Val Asn Asn Gln Ser Leu Pro Val Ser Pro Arg Leu Gln

-continued

```
                180                 185                 190
Leu Ser Asn Gly Asn Arg Thr Leu Thr Leu Phe Asn Val Thr Arg Asn
            195                 200                 205
Asp Thr Ala Ser Tyr Lys Cys Glu Thr Gln Asn Pro Val Ser Ala Arg
        210                 215                 220
Arg Ser Asp Ser Val Ile Leu Asn Val Leu Tyr Gly Pro Asp Ala Pro
225                 230                 235                 240
Thr Ile Ser Pro Leu Asn Thr Ser Tyr Arg Ser Gly Glu Asn Leu Asn
                245                 250                 255
Leu Ser Cys His Ala Ala Ser Asn Pro Pro Ala Gln Tyr Ser Trp Phe
            260                 265                 270
Val Asn Gly Thr Phe Gln Gln Ser Thr Gln Glu Leu Phe Ile Pro Asn
        275                 280                 285
Ile Thr Val Asn Asn Ser Gly Ser Tyr Thr Cys Gln Ala His Asn Ser
    290                 295                 300
Asp Thr Gly Leu Asn Arg Thr Thr Val Thr Thr Ile Thr Val Tyr Glu
305                 310                 315                 320
Pro Pro Lys Pro Phe Ile Thr Ser Asn Asn Ser Asn Pro Val Glu Asp
                325                 330                 335
Glu Asp Ala Val Ala Leu Thr Cys Glu Pro Glu Ile Gln Asn Thr Thr
            340                 345                 350
Tyr Leu Trp Trp Val Asn Asn Gln Ser Leu Pro Val Ser Pro Arg Leu
        355                 360                 365
Gln Leu Ser Asn Asp Asn Arg Thr Leu Thr Leu Leu Ser Val Thr Arg
    370                 375                 380
Asn Asp Val Gly Pro Tyr Glu Cys Gly Ile Gln Asn Glu Leu Ser Val
385                 390                 395                 400
Asp His Ser Asp Pro Val Ile Leu Asn Val Leu Tyr Gly Pro Asp Asp
                405                 410                 415
Pro Thr Ile Ser Pro Ser Tyr Thr Tyr Tyr Arg Pro Gly Val Asn Leu
            420                 425                 430
Ser Leu Ser Cys His Ala Ala Ser Asn Pro Pro Ala Gln Tyr Ser Trp
        435                 440                 445
Leu Ile Asp Gly Asn Ile Gln Gln His Thr Gln Glu Leu Phe Ile Ser
    450                 455                 460
Asn Ile Thr Glu Lys Asn Ser Gly Leu Tyr Thr Cys Gln Ala Asn Asn
465                 470                 475                 480
Ser Ala Ser Gly His Ser Arg Thr Thr Val Lys Thr Ile Thr Val Ser
                485                 490                 495
Ala Glu Leu Pro Lys Pro Ser Ile Ser Ser Asn Asn Ser Lys Pro Val
            500                 505                 510
Glu Asp Lys Asp Ala Val Ala Phe Thr Cys Glu Pro Glu Ala Gln Asn
        515                 520                 525
Thr Thr Tyr Leu Trp Trp Val Asn Gly Gln Ser Leu Pro Val Ser Pro
    530                 535                 540
Arg Leu Gln Leu Ser Asn Gly Asn Arg Thr Leu Thr Leu Phe Asn Val
545                 550                 555                 560
Thr Arg Asn Asp Ala Arg Ala Tyr Val Cys Gly Ile Gln Asn Ser Val
                565                 570                 575
Ser Ala Asn Arg Ser Asp Pro Val Thr Leu Asp Val Leu Tyr Gly Pro
            580                 585                 590
Asp Thr Pro Ile Ile Ser Pro Pro Asp Ser Ser Tyr Leu Ser Gly Ala
        595                 600                 605
```

```
Asp Leu Asn Leu Ser Cys His Ser Ala Ser Asn Pro Ser Pro Gln Tyr
    610                 615                 620

Ser Trp Arg Ile Asn Gly Ile Pro Gln Gln His Thr Gln Val Leu Phe
625                 630                 635                 640

Ile Ala Lys Ile Thr Pro Asn Asn Gly Thr Tyr Ala Cys Phe Val
                645                 650                 655

Ser Asn Leu Ala Thr Gly Arg Asn Asn Ser Ile Val Lys Ser Ile Thr
                660                 665                 670

Val Ser Ala Ser Gly Thr Ser Pro Gly Leu Ser Ala Gly Ala Thr Val
        675                 680                 685

Gly Ile Met Ile Gly Val Leu Val Gly Val Ala Leu Ile
    690                 695                 700

<210> SEQ ID NO 3
<211> LENGTH: 537
<212> TYPE: DNA
<213> ORGANISM: Artificial
<220> FEATURE:
<223> OTHER INFORMATION: synthetic construct
<220> FEATURE:
<221> NAME/KEY: CDS
<222> LOCATION: (1)..(534)

<400> SEQUENCE: 3 atg gtc ctc gac aca gca ggt ttg gag gag tac agt gca atg act gag      48
Met Val Leu Asp Thr Ala Gly Leu Glu Glu Tyr Ser Ala Met Thr Glu
1               5                  10                  15 tat aaa ctt gtg gtg gtt gga gct gtt ggc gta ggc aag agc gcc ttg      96
Tyr Lys Leu Val Val Val Gly Ala Val Gly Val Gly Lys Ser Ala Leu
                20                  25                  30 acg ata cag cta att cag aat cac ttt gtg gat gag tac gac cct acg    144
Thr Ile Gln Leu Ile Gln Asn His Phe Val Asp Glu Tyr Asp Pro Thr
            35                  40                  45 ata gag gac tcc tac agg aaa caa gta gta att gat gga gaa acc tgt    192
Ile Glu Asp Ser Tyr Arg Lys Gln Val Val Ile Asp Gly Glu Thr Cys
        50                  55                  60 ctc ttg gat att ctc gac aca gca ggt cga gag gag tac agt gca atg    240
Leu Leu Asp Ile Leu Asp Thr Ala Gly Arg Glu Glu Tyr Ser Ala Met
65                  70                  75                  80 agg gac cag tac atg aga act ggg gag ggc ttt ctt tgt gta ttt gcc    288
Arg Asp Gln Tyr Met Arg Thr Gly Glu Gly Phe Leu Cys Val Phe Ala
                85                  90                  95 ata aat aat act aaa tca ttt gaa gat att cac cat tat aga gaa caa    336
Ile Asn Asn Thr Lys Ser Phe Glu Asp Ile His His Tyr Arg Glu Gln
            100                 105                 110 att aaa aga gta aag gac tct gaa gat gtg cct atg gtc ctg gta ggg    384
Ile Lys Arg Val Lys Asp Ser Glu Asp Val Pro Met Val Leu Val Gly
        115                 120                 125 aat aag tgt gat ttg cct tct aga aca gta gac acg aaa cag gct cag    432
Asn Lys Cys Asp Leu Pro Ser Arg Thr Val Asp Thr Lys Gln Ala Gln
130                 135                 140 gag tta gca agg agt tac ggg att ccg ttc att gag acc tca gca aag    480
Glu Leu Ala Arg Ser Tyr Gly Ile Pro Phe Ile Glu Thr Ser Ala Lys
145                 150                 155                 160 aca aga cag ggt gtt gac gat gcc ttc tat aca tta gtc cga gaa att    528
Thr Arg Gln Gly Val Asp Asp Ala Phe Tyr Thr Leu Val Arg Glu Ile
                165                 170                 175 cga aaa tag                                                        537
Arg Lys
```

<210> SEQ ID NO 4
<211> LENGTH: 178
<212> TYPE: PRT
<213> ORGANISM: Artificial
<220> FEATURE:
<223> OTHER INFORMATION: Synthetic Construct

<400> SEQUENCE: 4

```
Met Val Leu Asp Thr Ala Gly Leu Glu Glu Tyr Ser Ala Met Thr Glu
1               5                   10                  15

Tyr Lys Leu Val Val Val Gly Ala Val Gly Val Gly Lys Ser Ala Leu
                20                  25                  30

Thr Ile Gln Leu Ile Gln Asn His Phe Val Asp Glu Tyr Asp Pro Thr
            35                  40                  45

Ile Glu Asp Ser Tyr Arg Lys Gln Val Val Ile Asp Gly Glu Thr Cys
        50                  55                  60

Leu Leu Asp Ile Leu Asp Thr Ala Gly Arg Glu Glu Tyr Ser Ala Met
65                  70                  75                  80

Arg Asp Gln Tyr Met Arg Thr Gly Glu Gly Phe Leu Cys Val Phe Ala
                85                  90                  95

Ile Asn Asn Thr Lys Ser Phe Glu Asp Ile His His Tyr Arg Glu Gln
            100                 105                 110

Ile Lys Arg Val Lys Asp Ser Glu Asp Val Pro Met Val Leu Val Gly
        115                 120                 125

Asn Lys Cys Asp Leu Pro Ser Arg Thr Val Asp Thr Lys Gln Ala Gln
130                 135                 140

Glu Leu Ala Arg Ser Tyr Gly Ile Pro Phe Ile Glu Thr Ser Ala Lys
145                 150                 155                 160

Thr Arg Gln Gly Val Asp Asp Ala Phe Tyr Thr Leu Val Arg Glu Ile
                165                 170                 175

Arg Lys
```

<210> SEQ ID NO 5
<211> LENGTH: 537
<212> TYPE: DNA
<213> ORGANISM: Artificial
<220> FEATURE:
<223> OTHER INFORMATION: Synthetic construct
<220> FEATURE:
<221> NAME/KEY: CDS
<222> LOCATION: (1)..(534)

<400> SEQUENCE: 5

```
atg gtc ctc gac aca gca ggt ttg gag gag tac agt gca atg act gag      48
Met Val Leu Asp Thr Ala Gly Leu Glu Glu Tyr Ser Ala Met Thr Glu
1               5                   10                  15 tat aaa ctt gtg gtg gtt gga gct tgt ggc gta ggc aag agc gcc ttg      96
Tyr Lys Leu Val Val Val Gly Ala Cys Gly Val Gly Lys Ser Ala Leu
                20                  25                  30 acg ata cag cta att cag aat cac ttt gtg gat gag tac gac cct acg     144
Thr Ile Gln Leu Ile Gln Asn His Phe Val Asp Glu Tyr Asp Pro Thr
            35                  40                  45 ata gag gac tcc tac agg aaa caa gta gta att gat gga gaa acc tgt     192
Ile Glu Asp Ser Tyr Arg Lys Gln Val Val Ile Asp Gly Glu Thr Cys
        50                  55                  60 ctc ttg gat att ctc gac aca gca ggt cga gag gag tac agt gca atg     240
Leu Leu Asp Ile Leu Asp Thr Ala Gly Arg Glu Glu Tyr Ser Ala Met
65                  70                  75                  80 agg gac cag tac atg aga act ggg gag ggc ttc ctt tgt gta ttt gcc     288
```

-continued

| | | | | | | | | | | | | |
|---|---|---|---|---|---|---|---|---|---|---|---|---|
| Arg | Asp | Gln | Tyr | Met | Arg | Thr | Gly | Glu | Gly | Phe | Leu | Cys | Val | Phe | Ala |
| | | | 85 | | | | | 90 | | | | | 95 | | |

| ata | aat | aat | act | aaa | tca | ttt | gaa | gat | att | cac | cat | tat | aga | gaa | caa | 336 |
|---|---|---|---|---|---|---|---|---|---|---|---|---|---|---|---|---|
| Ile | Asn | Asn | Thr | Lys | Ser | Phe | Glu | Asp | Ile | His | His | Tyr | Arg | Glu | Gln | |
| | | | 100 | | | | | 105 | | | | | 110 | | | |

| att | aaa | aga | gta | aag | gac | tct | gaa | gat | gtg | cct | atg | gtc | ctg | gta | ggg | 384 |
|---|---|---|---|---|---|---|---|---|---|---|---|---|---|---|---|---|
| Ile | Lys | Arg | Val | Lys | Asp | Ser | Glu | Asp | Val | Pro | Met | Val | Leu | Val | Gly | |
| | | | 115 | | | | | 120 | | | | | 125 | | | |

| aat | aag | tgt | gat | ttg | cct | tct | aga | aca | gta | gac | acg | aaa | cag | gct | cag | 432 |
|---|---|---|---|---|---|---|---|---|---|---|---|---|---|---|---|---|
| Asn | Lys | Cys | Asp | Leu | Pro | Ser | Arg | Thr | Val | Asp | Thr | Lys | Gln | Ala | Gln | |
| | | | 130 | | | | | 135 | | | | | 140 | | | |

| gag | tta | gca | agg | agt | tac | ggg | att | ccg | ttc | att | gag | acc | tca | gca | aag | 480 |
|---|---|---|---|---|---|---|---|---|---|---|---|---|---|---|---|---|
| Glu | Leu | Ala | Arg | Ser | Tyr | Gly | Ile | Pro | Phe | Ile | Glu | Thr | Ser | Ala | Lys | |
| 145 | | | | | 150 | | | | | 155 | | | | | 160 | |

| aca | aga | cag | ggt | gtt | gac | gat | gcc | ttc | tat | aca | tta | gtc | cga | gaa | att | 528 |
|---|---|---|---|---|---|---|---|---|---|---|---|---|---|---|---|---|
| Thr | Arg | Gln | Gly | Val | Asp | Asp | Ala | Phe | Tyr | Thr | Leu | Val | Arg | Glu | Ile | |
| | | | | 165 | | | | | 170 | | | | | 175 | | |

| cga | aaa | tag | | | | | | | | | | | | | | 537 |
|---|---|---|---|---|---|---|---|---|---|---|---|---|---|---|---|---|
| Arg | Lys | | | | | | | | | | | | | | | |

<210> SEQ ID NO 6
<211> LENGTH: 178
<212> TYPE: PRT
<213> ORGANISM: Artificial
<220> FEATURE:
<223> OTHER INFORMATION: Synthetic Construct

<400> SEQUENCE: 6

| Met | Val | Leu | Asp | Thr | Ala | Gly | Leu | Glu | Glu | Tyr | Ser | Ala | Met | Thr | Glu |
|---|---|---|---|---|---|---|---|---|---|---|---|---|---|---|---|
| 1 | | | | 5 | | | | | 10 | | | | | 15 | |

| Tyr | Lys | Leu | Val | Val | Val | Gly | Ala | Cys | Gly | Val | Gly | Lys | Ser | Ala | Leu |
|---|---|---|---|---|---|---|---|---|---|---|---|---|---|---|---|
| | | | 20 | | | | | 25 | | | | | 30 | | |

| Thr | Ile | Gln | Leu | Ile | Gln | Asn | His | Phe | Val | Asp | Glu | Tyr | Asp | Pro | Thr |
|---|---|---|---|---|---|---|---|---|---|---|---|---|---|---|---|
| | | | 35 | | | | | 40 | | | | | 45 | | |

| Ile | Glu | Asp | Ser | Tyr | Arg | Lys | Gln | Val | Val | Ile | Asp | Gly | Glu | Thr | Cys |
|---|---|---|---|---|---|---|---|---|---|---|---|---|---|---|---|
| | 50 | | | | | 55 | | | | | 60 | | | | |

| Leu | Leu | Asp | Ile | Leu | Asp | Thr | Ala | Gly | Arg | Glu | Glu | Tyr | Ser | Ala | Met |
|---|---|---|---|---|---|---|---|---|---|---|---|---|---|---|---|
| 65 | | | | | 70 | | | | | 75 | | | | | 80 |

| Arg | Asp | Gln | Tyr | Met | Arg | Thr | Gly | Glu | Gly | Phe | Leu | Cys | Val | Phe | Ala |
|---|---|---|---|---|---|---|---|---|---|---|---|---|---|---|---|
| | | | | 85 | | | | | 90 | | | | | 95 | |

| Ile | Asn | Asn | Thr | Lys | Ser | Phe | Glu | Asp | Ile | His | His | Tyr | Arg | Glu | Gln |
|---|---|---|---|---|---|---|---|---|---|---|---|---|---|---|---|
| | | | 100 | | | | | 105 | | | | | 110 | | |

| Ile | Lys | Arg | Val | Lys | Asp | Ser | Glu | Asp | Val | Pro | Met | Val | Leu | Val | Gly |
|---|---|---|---|---|---|---|---|---|---|---|---|---|---|---|---|
| | | | 115 | | | | | 120 | | | | | 125 | | |

| Asn | Lys | Cys | Asp | Leu | Pro | Ser | Arg | Thr | Val | Asp | Thr | Lys | Gln | Ala | Gln |
|---|---|---|---|---|---|---|---|---|---|---|---|---|---|---|---|
| | | | 130 | | | | | 135 | | | | | 140 | | |

| Glu | Leu | Ala | Arg | Ser | Tyr | Gly | Ile | Pro | Phe | Ile | Glu | Thr | Ser | Ala | Lys |
|---|---|---|---|---|---|---|---|---|---|---|---|---|---|---|---|
| 145 | | | | | 150 | | | | | 155 | | | | | 160 |

| Thr | Arg | Gln | Gly | Val | Asp | Asp | Ala | Phe | Tyr | Thr | Leu | Val | Arg | Glu | Ile |
|---|---|---|---|---|---|---|---|---|---|---|---|---|---|---|---|
| | | | | 165 | | | | | 170 | | | | | 175 | |

Arg Lys

<210> SEQ ID NO 7
<211> LENGTH: 537
<212> TYPE: DNA
<213> ORGANISM: Artificial
<220> FEATURE:
<223> OTHER INFORMATION: Synthetic construct
<220> FEATURE:

-continued

<221> NAME/KEY: CDS
<222> LOCATION: (1)..(534)

<400> SEQUENCE: 7

```
atg gtc ctc gac aca gca ggt ttg gag gag tac agt gca atg act gag     48
Met Val Leu Asp Thr Ala Gly Leu Glu Glu Tyr Ser Ala Met Thr Glu
1               5                   10                  15 tat aaa ctt gtg gtg gtt gga gct gat ggc gta ggc aag agc gcc ttg     96
Tyr Lys Leu Val Val Val Gly Ala Asp Gly Val Gly Lys Ser Ala Leu
                20                  25                  30 acg ata cag cta att cag aat cac ttt gtg gat gag tac gac cct acg    144
Thr Ile Gln Leu Ile Gln Asn His Phe Val Asp Glu Tyr Asp Pro Thr
            35                  40                  45 ata gag gac tcc tac agg aaa caa gta gta att gat gga gaa acc tgt    192
Ile Glu Asp Ser Tyr Arg Lys Gln Val Val Ile Asp Gly Glu Thr Cys
        50                  55                  60 ctc ttg gat att ctc gac aca gca ggt cga gag gag tac agt gca atg    240
Leu Leu Asp Ile Leu Asp Thr Ala Gly Arg Glu Glu Tyr Ser Ala Met
65                  70                  75                  80 agg gac cag tac atg aga act ggg gag ggc ttt ctt tgt gta ttt gcc    288
Arg Asp Gln Tyr Met Arg Thr Gly Glu Gly Phe Leu Cys Val Phe Ala
                85                  90                  95 ata aat aat act aaa tca ttt gaa gat att cac cat tat aga gaa caa    336
Ile Asn Asn Thr Lys Ser Phe Glu Asp Ile His His Tyr Arg Glu Gln
            100                 105                 110 att aaa aga gta aag gac tct gaa gat gtg cct atg gtc ctg gta ggg    384
Ile Lys Arg Val Lys Asp Ser Glu Asp Val Pro Met Val Leu Val Gly
        115                 120                 125 aat aag tgt gat ttg cct tct aga aca gta gac acg aaa cag gct cag    432
Asn Lys Cys Asp Leu Pro Ser Arg Thr Val Asp Thr Lys Gln Ala Gln
130                 135                 140 gag tta gca agg agt tac ggg att ccg ttc att gag acc tca gca aag    480
Glu Leu Ala Arg Ser Tyr Gly Ile Pro Phe Ile Glu Thr Ser Ala Lys
145                 150                 155                 160 aca aga cag ggt gtt gac gat gcc ttc tat aca tta gtc cga gaa att    528
Thr Arg Gln Gly Val Asp Asp Ala Phe Tyr Thr Leu Val Arg Glu Ile
                165                 170                 175 cga aaa tag                                                        537
Arg Lys
```

<210> SEQ ID NO 8
<211> LENGTH: 178
<212> TYPE: PRT
<213> ORGANISM: Artificial
<220> FEATURE:
<223> OTHER INFORMATION: Synthetic Construct

<400> SEQUENCE: 8

```
Met Val Leu Asp Thr Ala Gly Leu Glu Glu Tyr Ser Ala Met Thr Glu
1               5                   10                  15

Tyr Lys Leu Val Val Val Gly Ala Asp Gly Val Gly Lys Ser Ala Leu
                20                  25                  30

Thr Ile Gln Leu Ile Gln Asn His Phe Val Asp Glu Tyr Asp Pro Thr
            35                  40                  45

Ile Glu Asp Ser Tyr Arg Lys Gln Val Val Ile Asp Gly Glu Thr Cys
        50                  55                  60

Leu Leu Asp Ile Leu Asp Thr Ala Gly Arg Glu Glu Tyr Ser Ala Met
65                  70                  75                  80

Arg Asp Gln Tyr Met Arg Thr Gly Glu Gly Phe Leu Cys Val Phe Ala
                85                  90                  95
```

```
Ile Asn Asn Thr Lys Ser Phe Glu Asp Ile His His Tyr Arg Glu Gln
            100                 105                 110

Ile Lys Arg Val Lys Asp Ser Glu Asp Val Pro Met Val Leu Val Gly
            115                 120                 125

Asn Lys Cys Asp Leu Pro Ser Arg Thr Val Asp Thr Lys Gln Ala Gln
130                 135                 140

Glu Leu Ala Arg Ser Tyr Gly Ile Pro Phe Ile Glu Thr Ser Ala Lys
145                 150                 155                 160

Thr Arg Gln Gly Val Asp Asp Ala Phe Tyr Thr Leu Val Arg Glu Ile
                165                 170                 175

Arg Lys

<210> SEQ ID NO 9
<211> LENGTH: 537
<212> TYPE: DNA
<213> ORGANISM: Artificial
<220> FEATURE:
<223> OTHER INFORMATION: Synthetic construct
<220> FEATURE:
<221> NAME/KEY: CDS
<222> LOCATION: (1)..(534)

<400> SEQUENCE: 9 atg gtc ctc gac aca gca ggt ttg gag gag tac agt gca atg act gag     48
Met Val Leu Asp Thr Ala Gly Leu Glu Glu Tyr Ser Ala Met Thr Glu
1               5                   10                  15 tat aaa ctt gtg gtg gtt gga gct cgt ggc gta ggc aag agc gcc ttg     96
Tyr Lys Leu Val Val Val Gly Ala Arg Gly Val Gly Lys Ser Ala Leu
                20                  25                  30 acg ata cag cta att cag aat cac ttt gtg gat gag tac gac cct acg    144
Thr Ile Gln Leu Ile Gln Asn His Phe Val Asp Glu Tyr Asp Pro Thr
            35                  40                  45 ata gag gac tcc tac agg aaa caa gta gta att gat gga gaa acc tgt    192
Ile Glu Asp Ser Tyr Arg Lys Gln Val Val Ile Asp Gly Glu Thr Cys
        50                  55                  60 ctc ttg gat att ctc gac aca gca ggt cac gag gag tac agt gca atg    240
Leu Leu Asp Ile Leu Asp Thr Ala Gly His Glu Glu Tyr Ser Ala Met
65                  70                  75                  80 agg gac cag tac atg aga act ggg gag ggc ttt ctt tgt gta ttt gcc    288
Arg Asp Gln Tyr Met Arg Thr Gly Glu Gly Phe Leu Cys Val Phe Ala
                85                  90                  95 ata aat aat act aaa tca ttt gaa gat att cac cat tat aga gaa caa    336
Ile Asn Asn Thr Lys Ser Phe Glu Asp Ile His His Tyr Arg Glu Gln
            100                 105                 110 att aaa aga gta aag gac tct gaa gat gtg cct atg gtc ctg gta ggg    384
Ile Lys Arg Val Lys Asp Ser Glu Asp Val Pro Met Val Leu Val Gly
        115                 120                 125 aat aag tgt gat ttg cct tct aga aca gta gac acg aaa cag gct cag    432
Asn Lys Cys Asp Leu Pro Ser Arg Thr Val Asp Thr Lys Gln Ala Gln
130                 135                 140 gag tta gca agg agt tac ggg att ccg ttc att gag acc tca gca aag    480
Glu Leu Ala Arg Ser Tyr Gly Ile Pro Phe Ile Glu Thr Ser Ala Lys
145                 150                 155                 160 aca aga cag ggt gtt gac gat gcc ttc tat aca tta gtc cga gaa att    528
Thr Arg Gln Gly Val Asp Asp Ala Phe Tyr Thr Leu Val Arg Glu Ile
                165                 170                 175 cga aaa tag                                                        537
Arg Lys
```

```
<210> SEQ ID NO 10
<211> LENGTH: 178
<212> TYPE: PRT
<213> ORGANISM: Artificial
<220> FEATURE:
<223> OTHER INFORMATION: Synthetic Construct

<400> SEQUENCE: 10

Met Val Leu Asp Thr Ala Gly Leu Glu Glu Tyr Ser Ala Met Thr Glu
1               5                   10                  15

Tyr Lys Leu Val Val Gly Ala Arg Gly Val Gly Lys Ser Ala Leu
                20                  25                  30

Thr Ile Gln Leu Ile Gln Asn His Phe Val Asp Glu Tyr Asp Pro Thr
            35                  40                  45

Ile Glu Asp Ser Tyr Arg Lys Gln Val Val Ile Asp Gly Glu Thr Cys
50                  55                  60

Leu Leu Asp Ile Leu Asp Thr Ala Gly His Glu Glu Tyr Ser Ala Met
65                  70                  75                  80

Arg Asp Gln Tyr Met Arg Thr Gly Glu Gly Phe Leu Cys Val Phe Ala
                85                  90                  95

Ile Asn Asn Thr Lys Ser Phe Glu Asp Ile His His Tyr Arg Glu Gln
            100                 105                 110

Ile Lys Arg Val Lys Asp Ser Glu Asp Val Pro Met Val Leu Val Gly
        115                 120                 125

Asn Lys Cys Asp Leu Pro Ser Arg Thr Val Asp Thr Lys Gln Ala Gln
130                 135                 140

Glu Leu Ala Arg Ser Tyr Gly Ile Pro Phe Ile Glu Thr Ser Ala Lys
145                 150                 155                 160

Thr Arg Gln Gly Val Asp Asp Ala Phe Tyr Thr Leu Val Arg Glu Ile
                165                 170                 175

Arg Lys

<210> SEQ ID NO 11
<211> LENGTH: 8
<212> TYPE: PRT
<213> ORGANISM: Artificial
<220> FEATURE:
<223> OTHER INFORMATION: synthetic peptide

<400> SEQUENCE: 11

Gly Ile Gln Asn Ser Val Ser Ala
1               5

<210> SEQ ID NO 12
<211> LENGTH: 8
<212> TYPE: PRT
<213> ORGANISM: Artificial
<220> FEATURE:
<223> OTHER INFORMATION: synthetic peptide

<400> SEQUENCE: 12

Glu Ala Gln Asn Thr Thr Tyr Leu
1               5

<210> SEQ ID NO 13
<211> LENGTH: 9
<212> TYPE: PRT
<213> ORGANISM: Artificial
<220> FEATURE:
<223> OTHER INFORMATION: synthetic peptide

<400> SEQUENCE: 13
```

```
Ser Gln Val Thr Asn Pro Ala Asn Ile
1               5
```

```
<210> SEQ ID NO 14
<211> LENGTH: 2518
<212> TYPE: DNA
<213> ORGANISM: Homo sapiens
<220> FEATURE:
<221> NAME/KEY: CDS
<222> LOCATION: (494)..(1801)

<400> SEQUENCE: 14
```

| | |
|---|---|
| tttgcttttg cttatttccg tccatttccc tctctgcgcg cggaccttcc ttttccagat | 60 |
| ggtgagagcc gcgggacac ccgacgccgg ggcaggctga tccacgatcc tgggtgtgcg | 120 |
| taacgccgcc tggggctccg tgggcgaggg acgtgtgggg acaggtgcac cggaaactgc | 180 |
| cagactggag agttgaggca tcggaggcgc gagaacagca ctactactgc ggcgagacga | 240 |
| gcgcggcgca tcccaaagcc cggccaaatg cgctcgtccc tgggagggga gggaggcgcg | 300 |
| cctggagcgg ggacagtctt ggtccgcgcc ctcctcccgg gtctgtgccg ggacccggga | 360 |
| cccgggagcc gtcgcaggtc tcggtccaag gggcccctttt tctcggaagg gcggcggcca | 420 |
| agagcaggga aggtggatct caggtagcga gtctgggctt cggggacggc ggggagggga | 480 |

```
gccggacggg agg atg agc tcc cct ggc acc gag agc gcg gga aag agc      529
             Met Ser Ser Pro Gly Thr Glu Ser Ala Gly Lys Ser
                 1               5                  10 ctg cag tac cga gtg gac cac ctg ctg agc gcc gtg gag aat gag ctg    577
Leu Gln Tyr Arg Val Asp His Leu Leu Ser Ala Val Glu Asn Glu Leu
         15                  20                  25 cag gcg ggc agc gag aag ggc gac ccc aca gag cgc gaa ctg cgc gtg    625
Gln Ala Gly Ser Glu Lys Gly Asp Pro Thr Glu Arg Glu Leu Arg Val
 30                  35                  40 ggc ctg gag gag agc gag ctg tgg ctg cgc ttc aag gag ctc acc aat    673
Gly Leu Glu Glu Ser Glu Leu Trp Leu Arg Phe Lys Glu Leu Thr Asn
45                  50                  55                  60 gag atg atc gtg acc aag aac ggc agg agg atg ttt ccg gtg ctg aag    721
Glu Met Ile Val Thr Lys Asn Gly Arg Arg Met Phe Pro Val Leu Lys
                 65                  70                  75 gtg aac gtg tct ggc ctg gac ccc aac gcc atg tac tcc ttc ctg ctg    769
Val Asn Val Ser Gly Leu Asp Pro Asn Ala Met Tyr Ser Phe Leu Leu
             80                  85                  90 gac ttc gtg gcg gcg gac aac cac cgc tgg aag tac gtg aac ggg gaa    817
Asp Phe Val Ala Ala Asp Asn His Arg Trp Lys Tyr Val Asn Gly Glu
         95                 100                 105 tgg gtg ccg ggg ggc aag ccg gag ccg cag gcg ccc agc tgc gtc tac    865
Trp Val Pro Gly Gly Lys Pro Glu Pro Gln Ala Pro Ser Cys Val Tyr
    110                 115                 120 atc cac ccc gac tcg ccc aac ttc ggg gcc cac tgg atg aag gct ccc    913
Ile His Pro Asp Ser Pro Asn Phe Gly Ala His Trp Met Lys Ala Pro
125                 130                 135                 140 gtc tcc ttc agc aaa gtc aag ctc acc aac aag ctc aac gga ggg ggc    961
Val Ser Phe Ser Lys Val Lys Leu Thr Asn Lys Leu Asn Gly Gly Gly
                145                 150                 155 cag atc atg ctg aac tcc ttg cat aag tat gag cct cga atc cac ata   1009
Gln Ile Met Leu Asn Ser Leu His Lys Tyr Glu Pro Arg Ile His Ile
            160                 165                 170 gtg aga gtt ggg ggt cca cag cgc atg atc acc agc cac tgc ttc cct   1057
Val Arg Val Gly Gly Pro Gln Arg Met Ile Thr Ser His Cys Phe Pro
        175                 180                 185
```

```
gag acc cag ttc ata gcg gtg act gct tat cag aac gag gag atc aca    1105
Glu Thr Gln Phe Ile Ala Val Thr Ala Tyr Gln Asn Glu Glu Ile Thr
190                 195                 200 gct ctt aaa att aag tac aat cca ttt gca aaa gct ttc ctt gat gca    1153
Ala Leu Lys Ile Lys Tyr Asn Pro Phe Ala Lys Ala Phe Leu Asp Ala
205                 210                 215                 220 aag gaa aga agt gat cac aaa gag atg atg gag gaa ccc gga gac agc    1201
Lys Glu Arg Ser Asp His Lys Glu Met Met Glu Glu Pro Gly Asp Ser
                225                 230                 235 cag caa cct ggg tac tcc caa tgg ggg tgg ctt ctt cct gga acc agc    1249
Gln Gln Pro Gly Tyr Ser Gln Trp Gly Trp Leu Leu Pro Gly Thr Ser
            240                 245                 250 acc ctg tgt cca cct gca aat cct cat cct cag ttt gga ggt gcc ctc    1297
Thr Leu Cys Pro Pro Ala Asn Pro His Pro Gln Phe Gly Gly Ala Leu
        255                 260                 265 tcc ctc ccc tcc acg cac agc tgt gac agg tac cca acc ctg agg agc    1345
Ser Leu Pro Ser Thr His Ser Cys Asp Arg Tyr Pro Thr Leu Arg Ser
    270                 275                 280 cac cgg tcc tca ccc tac ccc agc ccc tat gct cat cgg aac aat tct    1393
His Arg Ser Ser Pro Tyr Pro Ser Pro Tyr Ala His Arg Asn Asn Ser
285                 290                 295                 300 cca acc tat tct gac aac tca cct gca tgt tta tcc atg ctg caa tcc    1441
Pro Thr Tyr Ser Asp Asn Ser Pro Ala Cys Leu Ser Met Leu Gln Ser
                305                 310                 315 cat gac aat tgg tcc agc ctt gga atg cct gcc cat ccc agc atg ctc    1489
His Asp Asn Trp Ser Ser Leu Gly Met Pro Ala His Pro Ser Met Leu
            320                 325                 330 ccc gtg agc cac aat gcc agc cca cct acc agc tcc agt cag tac ccc    1537
Pro Val Ser His Asn Ala Ser Pro Pro Thr Ser Ser Ser Gln Tyr Pro
        335                 340                 345 agc ctg tgg tct gtg agc aac ggc gcc gtc acc ccg ggc tcc cag gca    1585
Ser Leu Trp Ser Val Ser Asn Gly Ala Val Thr Pro Gly Ser Gln Ala
    350                 355                 360 gca gcc gtg tcc aac ggg ctg ggg gcc cag ttc ttc cgg ggc tcc ccc    1633
Ala Ala Val Ser Asn Gly Leu Gly Ala Gln Phe Phe Arg Gly Ser Pro
365                 370                 375                 380 gcg cac tac aca ccc ctc acc cat ccg gtc tcg gcg ccc tct tcc tcg    1681
Ala His Tyr Thr Pro Leu Thr His Pro Val Ser Ala Pro Ser Ser Ser
                385                 390                 395 gga tcc cca ctg tac gaa ggg gcg gcc gcg gcc aca gac atc gtg gac    1729
Gly Ser Pro Leu Tyr Glu Gly Ala Ala Ala Ala Thr Asp Ile Val Asp
            400                 405                 410 agc cag tac gac gcc gca gcc caa ggc cgc ctc ata gcc tca tgg aca    1777
Ser Gln Tyr Asp Ala Ala Ala Gln Gly Arg Leu Ile Ala Ser Trp Thr
        415                 420                 425 cct gtg tcg cca cct tcc atg tga agcagcaagg cccaggtccc gaaagatgca   1831
Pro Val Ser Pro Pro Ser Met
    430                 435 gtgactttt  tcgtggcag  ccagtggtga  ctggattgac  ctactaggta  cccagtggca  1891
gtctcaggtt aagaaggaaa tgcagcctca gtaacttcct tttcaaagca gtggaggagc   1951
acacggcacc tttccccaga gccccagcat cccttgctca cacctgcagt agcggtgctg   2011
tcccaggtgg cttacagatg aacccaactg tggagatgat gcagttggcc caacctcact   2071
gacggtgaaa aaatgtttgc cagggtccag aaacttttt  tggtttattt ctcatacagt   2131
gtattggcaa ctttggcaca ccagaatttg taaactccac cagtcctact ttagtgagat   2191
aaaaagcaca ctcttaatct tcttccttgt gctttcaag tagttagagt tgagctgtta    2251
aggacagaat aaaatcatag ttgaggacag caggttttag ttgaattgaa aatttgactg   2311
```

```
ctctgccccc tagaatgtgt gtattttaag catatgtagc taatctcttg tgttgttaaa    2371
ctataactgt ttcatatttt tcttttgaca aagtagccaa agacaatcag cagaaagcat    2431
tttctgcaaa ataaacgcaa tatgcaaaat gtgattcgtc cagttattag tgaagcccct    2491
ccttttgtga gtatttactg tttattg                                        2518
```

<210> SEQ ID NO 15
<211> LENGTH: 435
<212> TYPE: PRT
<213> ORGANISM: Homo sapiens

<400> SEQUENCE: 15

```
Met Ser Ser Pro Gly Thr Glu Ser Ala Gly Lys Ser Leu Gln Tyr Arg
1               5                   10                  15

Val Asp His Leu Leu Ser Ala Val Glu Asn Glu Leu Gln Ala Gly Ser
            20                  25                  30

Glu Lys Gly Asp Pro Thr Glu Arg Glu Leu Arg Val Gly Leu Glu Glu
        35                  40                  45

Ser Glu Leu Trp Leu Arg Phe Lys Glu Leu Thr Asn Glu Met Ile Val
    50                  55                  60

Thr Lys Asn Gly Arg Arg Met Phe Pro Val Leu Lys Val Asn Val Ser
65                  70                  75                  80

Gly Leu Asp Pro Asn Ala Met Tyr Ser Phe Leu Leu Asp Phe Val Ala
                85                  90                  95

Ala Asp Asn His Arg Trp Lys Tyr Val Asn Gly Glu Trp Val Pro Gly
            100                 105                 110

Gly Lys Pro Glu Pro Gln Ala Pro Ser Cys Val Tyr Ile His Pro Asp
        115                 120                 125

Ser Pro Asn Phe Gly Ala His Trp Met Lys Ala Pro Val Ser Phe Ser
    130                 135                 140

Lys Val Lys Leu Thr Asn Lys Leu Asn Gly Gly Gly Gln Ile Met Leu
145                 150                 155                 160

Asn Ser Leu His Lys Tyr Glu Pro Arg Ile His Ile Val Arg Val Gly
                165                 170                 175

Gly Pro Gln Arg Met Ile Thr Ser His Cys Phe Pro Glu Thr Gln Phe
            180                 185                 190

Ile Ala Val Thr Ala Tyr Gln Asn Glu Glu Ile Thr Ala Leu Lys Ile
        195                 200                 205

Lys Tyr Asn Pro Phe Ala Lys Ala Phe Leu Asp Ala Lys Glu Arg Ser
    210                 215                 220

Asp His Lys Glu Met Met Glu Glu Pro Gly Asp Ser Gln Gln Pro Gly
225                 230                 235                 240

Tyr Ser Gln Trp Gly Trp Leu Leu Pro Gly Thr Ser Thr Leu Cys Pro
                245                 250                 255

Pro Ala Asn Pro His Pro Gln Phe Gly Gly Ala Leu Ser Leu Pro Ser
            260                 265                 270

Thr His Ser Cys Asp Arg Tyr Pro Thr Leu Arg Ser His Arg Ser Ser
        275                 280                 285

Pro Tyr Pro Ser Pro Tyr Ala His Arg Asn Asn Ser Pro Thr Tyr Ser
    290                 295                 300

Asp Asn Ser Pro Ala Cys Leu Ser Met Leu Gln Ser His Asp Asn Trp
305                 310                 315                 320

Ser Ser Leu Gly Met Pro Ala His Pro Ser Met Leu Pro Val Ser His
                325                 330                 335
```

```
Asn Ala Ser Pro Pro Thr Ser Ser Ser Gln Tyr Pro Ser Leu Trp Ser
            340             345             350

Val Ser Asn Gly Ala Val Thr Pro Gly Ser Gln Ala Ala Ala Val Ser
        355             360             365

Asn Gly Leu Gly Ala Gln Phe Phe Arg Gly Ser Pro Ala His Tyr Thr
    370             375             380

Pro Leu Thr His Pro Val Ser Ala Pro Ser Ser Ser Gly Ser Pro Leu
385             390             395             400

Tyr Glu Gly Ala Ala Ala Ala Thr Asp Ile Val Asp Ser Gln Tyr Asp
                405             410             415

Ala Ala Ala Gln Gly Arg Leu Ile Ala Ser Trp Thr Pro Val Ser Pro
            420             425             430

Pro Ser Met
        435
```